(12) United States Patent
Munro et al.

(10) Patent No.: US 9,346,832 B2
(45) Date of Patent: May 24, 2016

(54) GOLD COMPLEXES FOR USE IN THE TREATMENT OF CANCER

(75) Inventors: Orde Quentin Munro, Pietermaritzburg (ZA); Kate Julie Akerman, Pietermaritzburg (ZA); Piers Akerman, Pietermaritzburg (ZA)

(73) Assignee: University of Kwazulu-Natal, Westville (ZA)

( * ) Notice: Subject to any disclaimer, the term of this patent is extended or adjusted under 35 U.S.C. 154(b) by 208 days.

(21) Appl. No.: 13/704,894

(22) PCT Filed: Jun. 14, 2011

(86) PCT No.: PCT/IB2011/052572
§ 371 (c)(1),
(2), (4) Date: Dec. 17, 2012

(87) PCT Pub. No.: WO2011/158176
PCT Pub. Date: Dec. 22, 2011

(65) Prior Publication Data
US 2013/0090472 A1     Apr. 11, 2013

(30) Foreign Application Priority Data

Jun. 17, 2010   (ZA) .................. 2010/04299

(51) Int. Cl.
| | |
|---|---|
| *C07F 1/12* | (2006.01) |
| *A61K 31/28* | (2006.01) |
| *C01G 7/00* | (2006.01) |
| *C07C 209/16* | (2006.01) |
| *C07C 213/02* | (2006.01) |
| *C07D 401/12* | (2006.01) |
| *C07D 487/22* | (2006.01) |
| *C07C 209/68* | (2006.01) |
| *C07C 209/86* | (2006.01) |
| *C07C 213/06* | (2006.01) |
| *C07D 207/335* | (2006.01) |

(52) U.S. Cl.
CPC ... *C07F 1/12* (2013.01); *C01G 7/00* (2013.01); *C07C 209/16* (2013.01); *C07C 209/68* (2013.01); *C07C 209/86* (2013.01); *C07C 213/02* (2013.01); *C07C 213/06* (2013.01); *C07D 207/335* (2013.01); *C07D 401/12* (2013.01); *C07D 487/22* (2013.01)

(58) Field of Classification Search
CPC ..... C07F 1/12; C07D 207/335; C07C 209/68; C07C 209/86; C07C 213/06
USPC ........... 556/110; 548/109, 402, 518; 544/225; 514/495
See application file for complete search history.

(56) References Cited

U.S. PATENT DOCUMENTS 5,688,487 A * 11/1997 Linder et al. .................. 424/1.65
2013/0259903 A1 * 10/2013 Mortenson et al. ........... 424/400

FOREIGN PATENT DOCUMENTS

WO   WO 2004/024146 A1   3/2004

OTHER PUBLICATIONS

International Search Report for PCT/IB2011/052572 dated Mar. 1, 2012.
Ott I.: "On the medicinal chemsity of gold complexes as anticancer drugs", Coordination Chemistry Reviews, vol. 253, No. 11-12, Jun. 2009, pp. 1670-1681.
Sun R. W.-Y. et al.: "The anti-cancer properties of gold(III) compounds with dianionic porphyrin and tetradentate ligands", Coordination Chemistry Review, vol. 253, No. 11-12, Jun. 2009, pp. 1682-1691.

* cited by examiner

*Primary Examiner* — Porfirio Nazario Gonzalez
(74) *Attorney, Agent, or Firm* — McCarter & English, LLP; Jill Ann Mello; Emily Dertz

(57) ABSTRACT

The invention provides compounds of the Formula (I), in which W is independently selected from $W^1$, $W^2$, $W^3$, $W^4$, $W^5$, -continued

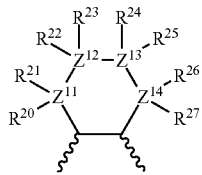
W⁴

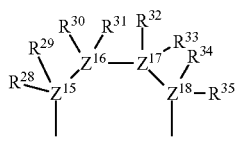
W⁵ or W represents a pair of substituents independently selected from H, alkyl, aryl or amide in which the amide is optionally part of a linking chain, and the $Z^n$—$Z^{n'}$ bonds (n=4-17; n'=n+1) are optionally of any whole or partial bond order, Y is $Y^1$

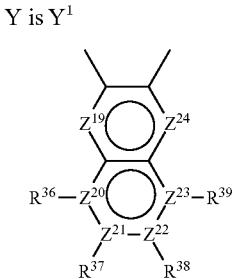
$Y^1$ or Y represents a pair of substituents independently selected from H, $C_1$-$C_6$ alkyl, $Z^5$ or $Z^6$ aryl, or Y is optionally a bridging structure that may comprise one or more $C_1$-$C_6$ amide, $C_1$-$C_6$ ether, or $C_1$-$C_6$ ester groups, R—$R^{39}$ are independently selected from no substituent, a lone pair of electrons, H, halogen, $C_5$-$C_6$ aryl, $C_1$-$C_{12}$ alkyl, amine, $C_1$-$C_6$ alkylamine, $C_1$-$C_6$ amide, nitro, cyano, carboxyl, $C_1$-$C_6$ ester, phosphane, thiol, $C_1$-$C_6$ thioether, $OR^{40}$, and suitable pairs of adjacent R groups (R—$R^{39}$) may optionally together form part of a $C_5$ or $C_6$ aryl ring, a $Z^5$ or $Z^6$ ring, $R^{40}$ is independently selected from H, $C_1$-$C_6$ alkyl, $Z^5$ or $Z^6$ aryl, $C_1$-$C_6$ ester, poly(—$C_2$O—), amine, and $C_1$-$C_6$ alkylamine, Z—$Z^{24}$ are independently selected from C, N, P, O, and S, and $X^-$ is a pharmaceutically acceptable anion, for the treatment of cancer.

21 Claims, 15 Drawing Sheets

(A)

(B)

(C)

(D)

(E)

(F)

GOLD COMPLEXES FOR USE IN THE TREATMENT OF CANCER

RELATED APPLICATIONS

This application is a 35 U.S.C. §371 national stage filing of International Application No. PCT/IB2011/052572, filed on Jun. 14, 2011 and claims the benefit of South African Patent Application No. 2010/04299, filed on Jun. 17, 2010. The entire contents of each of the foregoing applications are incorporated herein by reference.

THIS INVENTION relates to novel chemotherapeutic agents. It relates in particular to novel bis(pyrrolide-imine) and bis(imidazolato-imine) gold(III) Schiff base complexes as chemotherapeutic agents.

GENERAL BACKGROUND

The use of metal complexes in medicine can be traced back to 3500 BC and due to its particular physical and chemical properties gold has always been one of the many metals in use[1,2] Despite its wide use most of the gold based drugs have not been designed specifically for their function, and their mode of action is often unknown[2] The use of gold(0) is limited and is mostly used as a non-irritating food decoration and additive[1] Most of the gold-based drugs employ gold(I) and gold(III).[1]

The use of gold(I) based drugs has until recently been the main focus of medicinal research.[3,4] Their usefulness has mostly been in the treatment of rheumatoid arthritis, but testing against different cancer cell lines has been reported.[3] Gold(I) is a soft $d^{10}$ metal ion. The most common coordination geometry for gold(I) complexes is linear, with the molecules usually consisting of a central gold(I) ion coordinated by either phosphorous or sulfur donor ligands.[4,5] Au(I) complexes undergo *facile* ligand exchange in aqueous solutions, with the rate of ligand exchange increasing in the order $R_3P<RS^-<X^-$. The lability of the ligands contributes to both the therapeutic activity of Au(I) antiarthritic compounds and the side effects observed with these drugs.[4] One of the most well known of the gold(I) drugs is Auranofin (FIG. 1) which is widely used in the treatment of rheumatoid arthritis.

Auranofin and its many derivatives have also become the focus of research into gold(I) based anti-cancer agents. Several complexes have been found to exhibit cytotoxicity greater than that of cisplatin against melanoma and leukemia cancer cell lines in particular.[5] The in vitro test results of many gold(I) chelates against various human cancer cell lines have been promising.[4,5]

However, many of these complexes have never entered into clinical trials, since they have been associated with cardiotoxicity in preclinical trials.[2] Due to this cardiotoxicity of gold(I) chelates, gold(III) has become the focus of research into gold based chemotherapeutic agents.[5,6]

One of the first metal based drugs that was used in the treatment of cancer was cisplatin.[6,7] Cisplatin is still widely used today in the treatment of several types of tumors, particularly testicular cancer. Its use is, however, hindered by some clinical problems such as a severe toxicity towards non-cancerous tissue and the frequent occurrence of initial and acquired resistance to the treatment.[6] The most concerning adverse side effect is nephrotoxicity correlated to platinum binding and inactivation of renal thiol-containing enzymes.[6] These drawbacks to the success of cisplatin in anticancer chemotherapy has raised great interest in the study of metal complexes to be used as antitumor agents, instigating the ongoing investigation of alternative metal-based drugs.

The allure of gold(III) as an anti-tumor agent is that it has a $d^8$ electron configuration, with vacant $d(x^2-y^2)$ orbitals, and therefore adopts a rigorously square planar coordination geometry. Gold(III) is therefore isostructural and isoelectronic to platinum(II).[8] Despite the similarity to platinum(II) literature relating to the use of gold(III) as a chemotherapeutic agent is scarce.[6] The rarity of data on gold(III) complexes probably derives from their high redox potential and relatively poor stability, which make their use rather problematic under physiological conditions.[5,6] The gold(III) ion can be readily reduced to the more stable gold(I) ion or even metallic gold(0) under the in vivo reducing conditions, characteristic of the mammalian environment.[5] The coordination of a ligand, which is a strong σ-donor and π-acceptor ligand that can stabilize the gold(III) ion under physiological conditions is therefore critical if gold(III) is to be used in the treatment of cancer.[5,9]

Scheme 2

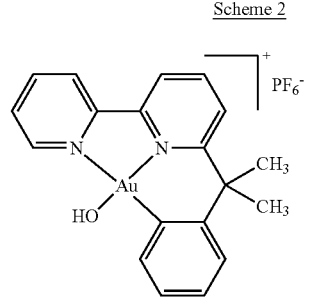

[Au(bipy-H)(OH)][PF$_6$]

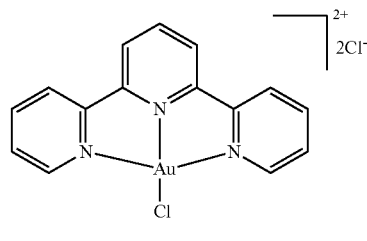

[Au(terpy)Cl]Cl$_2$

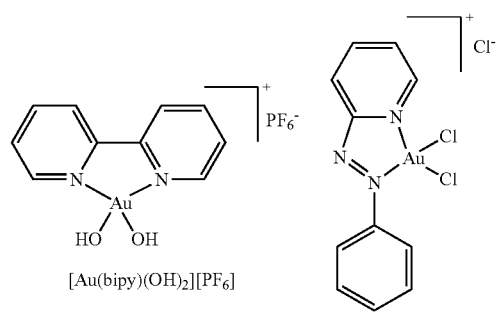

[Au(bipy)(OH)$_2$][PF$_6$]          [Au(azpy)Cl$_2$]Cl

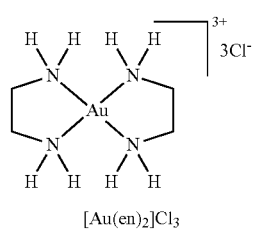

[Au(en)$_2$]Cl$_3$

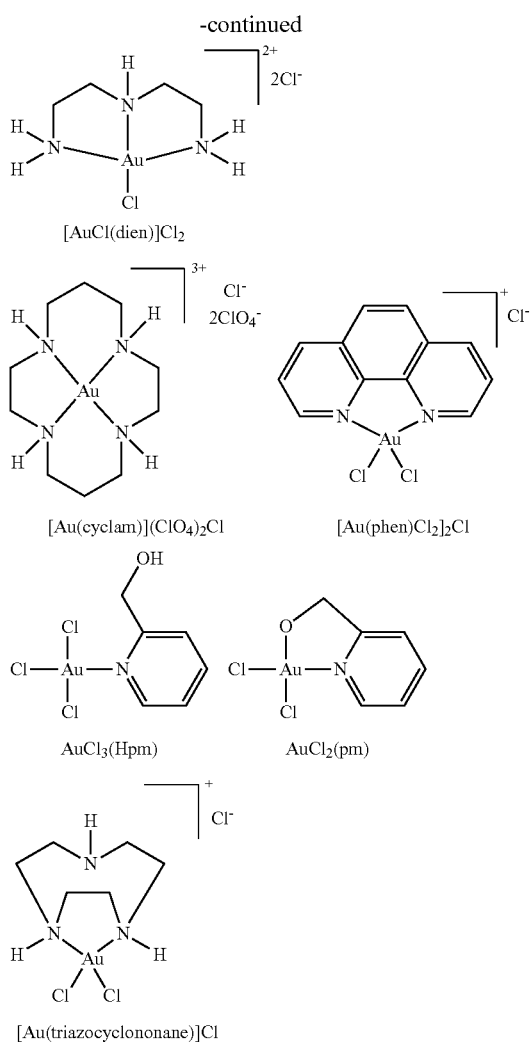

Gold(III) complexes with Au—N bonds that have been tested for cytotoxicity against human cancer cell lines.[10]

There are currently no commercially available gold(III) compounds being used as chemotherapeutic agents. There are, however, many gold(III) complexes that have shown very promising in vitro and in vivo activity against many different human cancer cell lines.[10] The structures of a range of gold (III) chelates, which have Au—N bonds, that have been tested for cytotoxicity are shown in Scheme 2.

The two pyridyl gold(III) species, [AuCl$_3$(Hpm)] and [AuCl$_2$(pm)] (Scheme 2) have good cytotoxicity towards a range of human cancer cell lines, particularly human ovarian cancer cell lines. The results of these tests although promising were comparable to the screening results of NaAuCl$_4$ which is their parent compound.[10] The other drawback of these compounds is that although stable in organic solutions, they are susceptible to reduction in aqueous buffer media, which limits their practical usefulness.[10,11] The bipyridine type complexes, [Au(bipy)(OH)$_2$][PF$_6$] and [Au(bipy-H)(OH)][PF$_6$] were, on the other hand, found to be stable in aqueous buffer media. Unfortunately they were found to interact with calf thymus DNA only weakly. Despite this weak interaction with calf thymus DNA, both bipyridyl gold(III) complexes show IC$_{50}$ values falling into the micromolar range against an ovarian carcinoma cell line. [Au(bipy-H)(OH)][PF$_6$] is the most active of the two compounds. The results of the tests against other ovarian cancer cell lines as well as leukemia cell lines were less encouraging.[9]

The gold(III) complexes with multidentate N-donor ligands; [Au(phen)Cl$_2$]Cl, [Au(terpy)Cl]Cl$_2$, [AuCl(dien)]Cl$_2$, [Au(cyclam)](ClO$_4$)$_2$Cl and [Au(en)$_2$]Cl$_2$, showed reasonable stability in physiological buffer solutions at 37° C. These gold(III) complexes have been greatly stabilized by the chelation of the gold(III) ion to polyamine ligands. This stabilization was evidenced by measurements of the reduction potentials of the complexes.[8,10] The stabilization was less evident for the less basic phenanthrene and terpyridine ligands.[8] With the exception of the complex [Au(cyclam)](ClO$_4$)$_2$Cl, all complexes exhibited good cytotoxicity against the human ovarian cancer cell line A2780. These complexes also exhibited good cytotoxicity towards the cisplatin-resistant A2780 ovarian cancer cell line; this suggests that gold (III) compounds might overcome the phenomenon of drug resistance.[8,10] The free ligands that were coordinated to a gold(III) ion to give the complexes were also screened against the same cancer cell lines to ensure that the cytotoxicity was a result of the presence of the gold(III) ion. These test results showed that the free ethylenediamine ligand was devoid of any activity. The potency of free phenanthrene and terpyridine, on the other hand, was comparable to that of the respective gold(III) complexes making the screening results of these chelates difficult to interpret. The study did, however, prove that the cytotoxicity of [Au(en)$_2$]Cl$_2$ was a direct consequence of the presence of the gold(III) ion.[10]

The complex [Au(azpy)Cl$_2$]Cl, which contains a bidentate N-donor ligand, exhibited promising cytotoxic activity in cisplatin-sensitive and cisplatin-resistant ovarian carcinoma and leukemia cancer cell lines. Interestingly, solutions of [Au(azpy)Cl$_2$]Cl underwent a cyclization reaction under physiological conditions leading to the formation of a tricyclic cationic organic compound, which also exhibited good cytotoxic activity.[10,12]

The gold(III) dithiocarbamate complexes, are examples of gold(III) chelates with Au—S bond which are bound to ligands through a sulfur atom. Examples of dithiocarbamate complexes that have been screened against various cancer cell lines are shown below in Scheme 3.

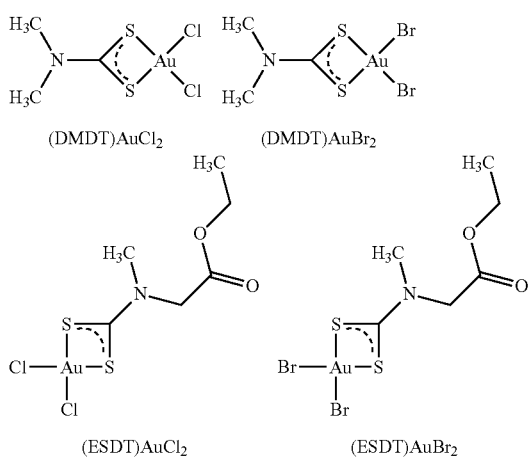

Gold(III) chelates with sulfur-bound ligands.

The Gold(III) dithiocarbamate complexes that have been screened against various human cancer cell lines exhibited greater cytotoxic effects compared to cisplatin. The complexes were also bioactive against drug resistant cancer cell lines and induced apoptosis.[6,7] The compounds have proven to be stabile under physiological conditions and readily bind to calf thymus DNA, inhibiting both DNA and RNA synthesis. Experiments on red blood cells indicated that haemolytic properties might contribute significantly to the bioactivity of the agents. The complexes triggered cancer cell death via apoptotic and non-apoptotic pathways and affected mitochondrial functions.[6,7,10] The free ligand ESDT (Scheme 3) did not exhibit proteosome inhibitory activity and the parent gold salts KAuCl$_4$ and KAuBr$_4$ also showed weaker inhibitory activities than (ESDT)AuBr$_2$.

Although the in vitro anti-cancer activity of gold(III) compounds has been documented for more than three decades, very few demonstrate promising in vivo anti-cancer activities. Among the gold(III) compounds in the literature that have undergone in vivo testing are the gold(III) dithiocarbamate compounds, which inhibited approximately 50% growth of breast cancer cells a month after the first dose of the compound.[13]

DETAILED BACKGROUND RELATING TO THE INVENTION

The gold(III) chelates of this invention have tetradentate dianion ligands. More specifically they are N$_2$N'$_2$ tetradentate ligands and therefore are closely related to the highly cytotoxic gold(III) tetraarylporphyrins. The advantage of tetradentate ligands is that they are better able to stabilize the gold(III) cation against reduction under physiological conditions and are therefore potentially more useful as drugs.[5,9] Coordination of a tetradentate dianionic ligand to gold(III) gives a mono-cationic gold(III) compound having a planar geometry. These mono-cationic complexes have a similar overall structure to lipophilic organic cations, which have proven to be effective chemotherapeutic agents.[13] The structures of a selection of known gold(III) chelates with tetradentate, dianionic ligands[13] are set out in Scheme 4.

Scheme 4

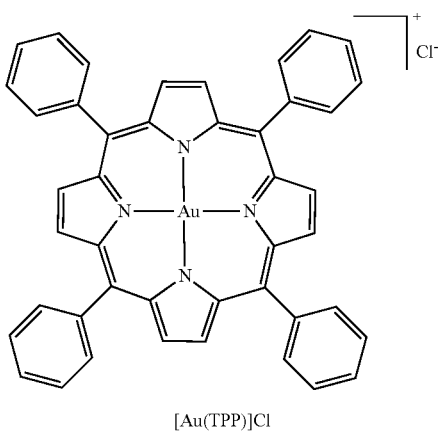

[Au(TPP)]Cl

-continued

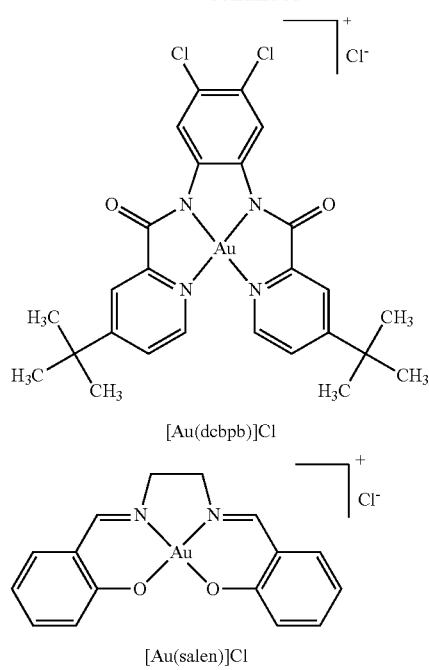

[Au(dcbpb)]Cl

[Au(salen)]Cl

The structures of a selection of gold(III) chelates with tetradentate, dianionic ligands.[13]

The gold(III) porphyrins have proven to be stable under physiological conditions. The complexes [Au(dcbpb)]Cl and [Au(salen)]Cl, on the other hand, show signs of slow decomposition under similar conditions.[13] [Au(TPP)]Cl has displayed promising anticancer activities toward a panel of human cancer cell lines including nasopharyngeal carcinoma, promyelocytic leukaemia, hepatocellular carcinoma, cervical epithelioid carcinoma, and oral epidermoid carcinoma.[13] The IC$_{50}$ values of [Au(TPP)]Cl ranged between 0.11 and 0.73 μM. These IC$_{50}$ values show that [Au(TPP)]Cl is several hundred times more cytotoxic than cisplatin. This compound also shows significant cytotoxicity against KB-3-1 and its multi-drug resistant (KB-V1) variant. The latter possesses a high level of membrane P-glycoproteins, which exclude drugs such as vinblastine and doxorubicin.[13] To investigate the cytotoxic effect of [Au(TPP)]Cl on non-cancerous cells, the cytotoxicity toward peripheral blood mononuclear cells (PBMCs) from healthy individuals and CCD-19Lu cells, which is a fibroblast cell line derived from normal lung tissue, were examined. Results by MTT assay revealed that [Au(TPP)]Cl exhibits at least ten-fold higher cytotoxicity to cancer cells than non-cancerous cells.[13] The presence of gold(III) ions has been proven to be critical for the observed in vitro chemotherapeutic properties. This conclusion is based on the inactivity of [Zn$^{II}$(TPP)]. The zinc(II) analogue of [Au(TPP)]Cl exhibits an IC$_{50}$ value greater than 50 μM. The gold(III) ion is unstable under physiological conditions as it undergoes reduction to colloidal gold. The porphyrin ligand is, however able to stabilize the gold(III) ion and it is hypothesized that [Au(TPP)]$^+$ acts as a stable lipophilic planar cation for binding to bio-molecular target(s) through non-covalent interactions.[13]

The cytotoxic properties of the gold(III) salen Schiff base complexes and the bis(pyridyl)carboxamide gold(III) complexes have also been evaluated.[13] These compounds have been shown to exhibit a cytotoxicity comparable to that of cisplatin with a IC$_{50}$ values in the range of 10-30 μM.

There are two different pathways via which a compound can cause cell death, these are apoptosis and necrosis. Apoptosis is characterized by an ordered series of biochemical and biophysical reactions that are regulated by various genes, this is in contrast to necrosis which is premature cell death. While apoptosis often provides beneficial effects to the organism, necrosis is almost always detrimental, and can be fatal. Apoptosis does not trigger inflammatory tissue reactions, and thus is advantageous for cytotoxic chemotherapeutic agents to be able to induce apoptotic cell death as opposed to necrosis. The compound [Au(TPP)]Cl induced cytotoxicity in NPC cells via an apoptotic pathway.[13] By means of confocal imaging, typical apoptotic morphological changes were detected, including the formation of apoptotic bodies, chromatin condensation and DNA fragmentation. The induced apoptosis was also confirmed by the oligonucleosomic degradation of cellular DNA, as this type of chromatin degradation is characteristic of apoptosis. These experiments confirm that [Au(TPP)]Cl induces apoptotic cell death in NPC cells as opposed to necrosis.[13] The dithiocarbamate gold(III) complexes were also found to cause apoptosis as opposed to necrosis[6,7] this would suggest that gold(III) chelates could potentially favour an apoptotic pathway as opposed to a necrotic pathway. This would make them more attractive chemotherapeutic agents.

Tetradentate Schiff base ligands comprising two pyrrole groups bridged by a synthetically variable di(azomethine) unit have been known for several decades.[14] However, studies of both the free base ligands as well as their metal chelates are quite limited.[14] Coordination of this class of ligands to a metal cation usually occurs with the concomitant deprotonation of the pyrrole NH groups, this means that they are $N_2N'_2$ tetradentate, dianionic ligands. The ligands have been previously bound to Ru(II), Pd(II), Ni(II), Co(III), Mn(II), Cu(II), Sm(II), Pt(II) and Fe(III).[15-23] Chelation of the former by the dianionic ligand will result in a neutral metal chelate, with the exception of Co(III) and Fe(III), which will give a monocationic complex. These metal chelates have been used as hydrogenation catalysts when coordinated to Pd(II)[16] as well as high efficiency red electrophosphorescence materials when chelated to Pt(II).[22] The complexes also show a similar coordination geometry, regardless of the electronic configuration of the metal ion. The metal ions exhibiting a nominally square planar coordination geometry, regardless of whether the bis(imine) linkage is aromatic or a straight or substituted alkyl group. The bridging does, however, affect the extent to which the metal ion is distorted from the optimum square planar geometry. Short bridges, of two carbons in length, whether aromatic or alkyl result in a smaller bite angle of the ligand. This small bite angle manifests itself as an acute $N_{imine}$-M-$N_{imine}$ bond angle.[16,23] The longer three carbon bridge allows for a larger bite angle and the $N_{imine}$-M-$N_{imine}$ bond angle therefore tends towards a right angle.[16]

The free base bis(pyrrole-imine) compounds have been shown to exhibit fascinating supramolecular structures both with aromatic[24] and alkyl[14] bridges. The pyrrole N—H and imine type nitrogen atoms form a highly predictable hydrogen bonding motif. The compounds with aromatic bridges have even been used to form distinct nanostructures, with the effect of isomeric molecules being examined in an attempt to try and further understand the self assembly of organic molecules into distinct nanostructures.[24]

The Invention

The present invention provides new classes of gold(III) bis(pyrrolide-imine) and bis(imidazolato-imine) compounds. Several of these compounds have been shown to be cytotoxic towards a wide range of human cancer cell lines having an activity similar to, or better than, cisplatin which is currently the industry standard. The most active compound has been proven in vitro to be a poison of topoisomerase II at low concentrations ($EC_{50}$=0.5 µM) and a catalytic inhibitor of the enzyme at higher concentrations (50 µM).

An extensive search of the literature as well as the Cambridge Structural Database (CSD) has confirmed that the gold(III) chelates of the invention are new. Neither the structures nor the syntheses of the bis(pyrrolide-imine) and bis(imidazolato-imine) gold(III) Schiff base complexes of the invention have been reported and, accordingly, there has been no report of the use of the gold(III) chelates of the invention as cytotoxic agents for the treatment of cancer.

According to a first aspect of the invention, there is provided a compound selected from compounds of the Formula (I),

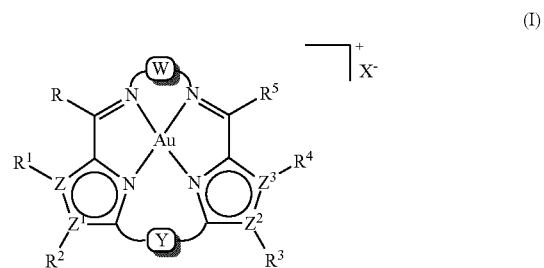

in which
W is independently selected from $W^1$, $W^2$, $W^3$, $W^4$, $W^5$,

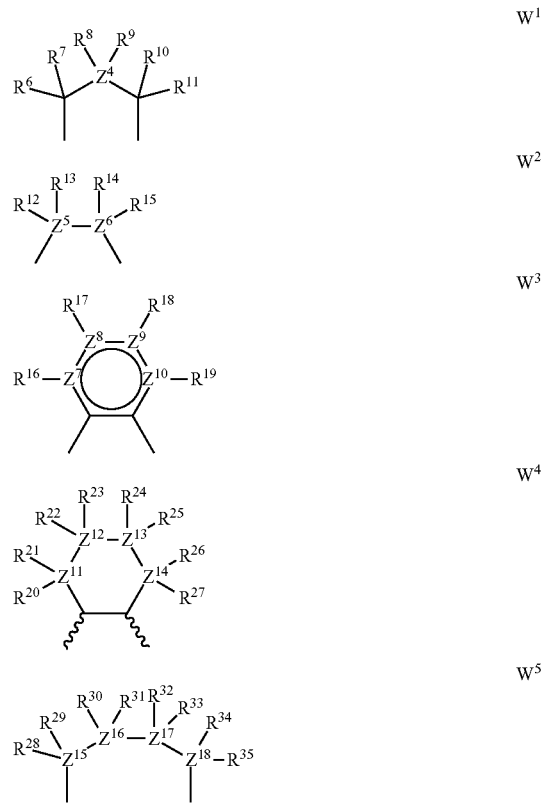

or W represents a pair of substituents independently selected from H, $C_1$-$C_6$ alkyl, $Z^5$ or $Z^6$ aryl or $C_1$-$C_6$ amide in which the amide is optionally part of a linking chain, and the $Z^n$—$Z^{n'}$ bonds (n=4-17; n'=n+1) are optionally of any whole or partial bond order,
Y is $Y^1$

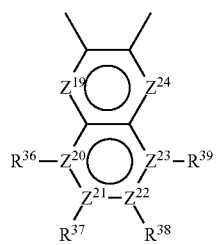

or Y represents a pair of substituents independently selected from H, $C_1$-$C_6$ alkyl, $Z^5$ or $Z^6$ aryl, or Y is optionally a bridging structure that may comprise one or more $C_1$-$C_6$ amide, $C_1$-$C_6$ ether, or $C_1$-$C_6$ ester groups, R—$R^{39}$ are independently selected from no substituent, a lone pair of electrons, H, halogen, $C_5$-$C_6$ aryl, $C_1$-$C_{12}$ alkyl, amine, $C_1$-$C_6$ alkylamine, $C_1$-$C_6$ amide, nitro, cyano, carboxyl, $C_1$-$C_6$ ester, phosphane, thiol, $C_1$-$C_6$ thioether, $OR^{40}$, and suitable pairs of adjacent R groups (R—$R^{39}$) may optionally together form part of a $C_5$ or $C_6$ aryl ring, a $Z^5$ or $Z^6$ ring, $R^{40}$ is independently selected from H, $C_1$-$C_6$ alkyl, $Z^5$ or $Z^6$ aryl, $C_1$-$C_6$ ester, poly(—$C_2$O—), amine, and $C_1$-$C_6$ alkylamine, Z—$Z^{24}$ are independently selected from C, N, P, O, and S, and $X^-$ is a pharmaceutically acceptable anion.

The anion $X^-$ may be selected from halide, hexafluorophosphate, nitrate, and triflate.

Examples of representative structurally characterized and tested compounds of the invention are the following compounds.

Compound 1.1a (MA_AuPr) in which chelate substituents R—$R^5$ are H, Z—$Z^3$ are C, the bridge W is —$CH_2CH_2CH_2$—, Y is 2H, and the anion X is $Cl^-$.

Compound 1.1b (MA_AuDM) in which chelate substituents R—$R^5$ are H, Z—$Z^3$ are C, the bridge W is —$CH_2C(CH_3)_2CH_2$—, Y is 2H, and the anion X is $Cl^-$.

Compound 1.1c (MA_AuOH) in which chelate substituents R—$R^5$ are H, Z—$Z^3$ are C, the bridge W is —$CH_2CH(OH)CH_2$—, Y is 2H, and the anion X is $Cl^-$.

Compound $1.1Y^1a$ (KA_AumacroPr) in which chelate substituents R—$R^5$ are H, Z—$Z^3$ are C, the bridge W is —$CH_2CH_2CH_2$—, Y is $Y^1$, where $R^{46}$-$R^{49}$ are H, $Z^{29}$ and $Z^{34}$ are N, $Z^{30}$-$Z^{33}$ are C, and the anion X is $PF_6^-$.

Compound $1.1Y^1b$ (KA_AumacroDM) in which chelate substituents R—$R^5$ are H, Z—$Z^3$ are C, the bridge W is —$CH_2C(CH_3)_2CH_2$—, Y is $Y^1$, where $R^{46}$-$R^{49}$ are H, $Z^{29}$ and $Z^{34}$ are N, $Z^{30}$-$Z^{33}$ are C, and the anion X is $PF_6^-$.

Compound $1.5Y^1a$ (KA_AumacroBu) in which chelate substituents R—$R^5$ are H, Z—$Z^3$ are C, the bridge W is —$CH_2CH_2CH_2CH_2$—, Y is $Y^1$, where $R^{46}$-$R^{49}$ are H, $Z^{29}$ and $Z^{34}$ are N, $Z^{30}$-$Z^{33}$ are C, and the anion X is $PF_6^-$.

Compound 1.1f (KA_AuMeImPr) in which chelate substituents R and $R^5$ are H, $R^1$ and $R^4$ are $CH_3$, $R^2$ and $R^3$ are lone pairs of electrons, Z and $Z^3$ are C, $Z^1$ and $Z^2$ are N, the bridge W is —$CH_2CH_2CH_2$—, Y is 2H, and the anion X is $PF_6^-$.

Compound 1.1g (KA_AuMeImDM) in which chelate substituents R and $R^5$ are H, $R^1$ and $R^4$ are $CH_3$, $R^2$ and $R^3$ are lone pairs of electrons, Z and $Z^3$ are C, $Z^1$ and $Z^2$ are N, the bridge W is —$CH_2C(CH_3)CH_2$—, Y is 2H, and the anion X is $PF_6^-$ FIGS. 2, 3 and 4 show, by way of illustration of the parent derivatives of each new class of gold(III) chelates, partially labeled thermal ellipsoid diagrams of the X-ray crystal structures of MA_AuPr (compound 1.1a), KA_AumacroPr (compound $1.1Y^1a$), and KA_AuMeImPr (compound 1.1f), respectively.

The single crystal X-ray structural data for compounds 1.1a, 1.1f, and $1.1Y^1a$ are summarized in Table 1. Other crystallographically characterized complexes of the invention are summarized in Table 2.

TABLE 1

Crystal data and structure refinement details for MA_AuPr (1.1a), KA_AumacroPr ($1.1Y^1a$), and KA_AuMeImPr (1.1f).

| Compound | MA_AuPr | KA_AumacroPr | KA_AuMeImPr |
|---|---|---|---|
| Formula | $C_{13}H_{14}AuClN_4$ | $C_{21}H_{16}AuN_6F_6P$ | $C_{13}H_{16}AuF_6N_6P$ |
| Cell setting | Triclinic | Monoclinic | Monoclinic |
| Space group | P-1 | P2/c | Cc |
| Formula weight | 458.70 | 694.33 | 598.25 |
| a/Å, b/Å, c/Å | 7.5888(4), 9.4183(3), 10.5118(4) | 16.473(5), 6.980(5), 18.804(5) | 16.348(5), 12.015(5), 9.488(5) |
| α/°, β/°, γ/° | 68.707(4), 72.787(4), 72.194(4) | 90, 105.675(5), 90 | 90, 106.865(5), 90 |
| T/K | 140(2) | 173(2) | 295(2) |
| Z | 2 | 4 | 4 |
| V/Å³ | 651.86(5) | 2081.7(17) | 1783.5(13) |
| Density (g cm⁻³) | 2.337 | 2.2155 | 2.228 |
| μ, (mm⁻¹) | 11.479 | 7.220 | 8.410 |
| Crystal Dimensions (mm³) | 0.10 × 0.10 × 0.10 | 0.50 × 0.02 × 0.01 | 0.45 × 0.25 × 0.15 |
| Radiation λ (Å) | 0.71073 | 0.71073 | 0.71073 |
| Total Data Collected | 10737 | 14581 | 6002 |
| Unique Data | 4510 [R(int)] = 0.0173 | 4010 [R(int)] = 0.060 | 2635 [R(int)] = 0.032 |
| Refinement Method | Full-matrix least-squares on $F^2$ | Full-matrix least-squares on $F^2$ | Full-matrix least-squares on $F^2$ |
| Goodness-of-fit on $F^2$ | 1.032 | 0.940 | 1.020 |
| Final R indices [I > 2sigma(I)] | $R_1$ = 0.0165 $wR_2$ = 0.0403 | $R_1$ = 0.0320 $wR_2$ = 0.0703 | $R_1$ = 0.0271 $wR_2$ = 0.0660 |
| Final R indices [all data] | $R_1$ = 0.0189 $wR_2$ = 0.0406 | $R_1$ = 0.0452 $wR_2$ = 0.0733 | $R_1$ = 0.0288 $wR_2$ = 0.0655 |
| Largest diff. peak/hole | 1.697/−1.902 | 2.282/−1.453 | 0.134/−1.296 |

It is noteworthy that other anions may be used to crystallize the cations of this invention. For example, we have recently acquired X-ray data for the triflate salt of KA_aumacroDM ($C_{24}H_{20}AuF_3N_6O_3S$, monoclinic space group Cc, a=17.092(5) Å, b=25.520(5) Å, c=13.625(5) Å, α=90°, β=119.057(5°), γ=90°, V=5195(3) Å³, Z=8, T=−153(2° C.).

The Applicant has found that MA_AuPr (1.1a), by way of example, has several advantages over currently available inorganic chemotherapeutic agents in clinical use. Firstly, the synthesis of the ligands belonging to the 1.1a-1.1f series of compounds is a simple one-pot reaction, requiring minimal purification. Chelation of the ligand to gold(III) is simple and gives a clean easily re-crystallized product. Derivatization of the parent ligand was found to be possible and different derivatives showed varying activity, suggesting that there is a structure/activity relationship between the different derivatives. In vitro testing showed that the chelate 1.1a was more effective than cisplatin against ca. 25% of the 60 human cancer cell lines against which it was tested. The in vitro mechanism of action of the drug has been established and is highly specific. This indicates that the activity of the drug can be carefully controlled.

According to a second aspect of the invention, there is provided a compound selected from compounds of the Formula (I),

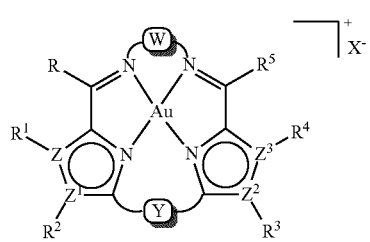

in which

W is independently selected from $W^1$, $W^2$, $W^3$, $W^4$, $W^5$,

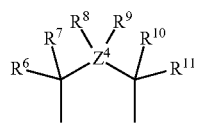

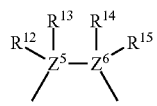

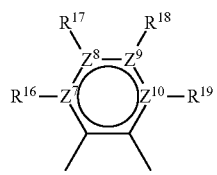

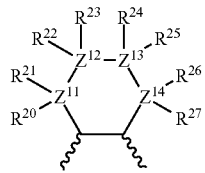

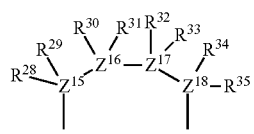

or W represents a pair of substituents independently selected from H, $C_1$-$C_6$ alkyl, $Z^5$ or $Z^6$ aryl or $C_1$-$C_6$ amide in which the amide is optionally part of a linking chain, and the $Z^n$—$Z^{n'}$ bonds (n=4-17; n'=n+1) are optionally of any whole or partial bond order, Y is $Y^1$

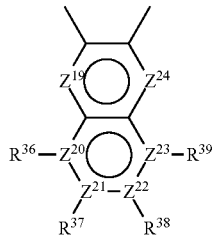

or Y represents a pair of substituents independently selected from H, $C_1$-$C_6$ alkyl, $Z^5$ or $Z^6$ aryl, or Y is optionally a bridging structure that may comprise one or more $C_1$-$C_6$ amide, $C_1$-$C_6$ ether, or $C_1$-$C_6$ ester groups, R—$R^{39}$ are independently selected from no substituent, a lone pair of electrons, H, halogen, $C_5$-$C_6$ aryl, $C_1$-$C_{12}$ alkyl, amine, $C_1$-$C_6$ alkylamine, $C_1$-$C_6$ amide, nitro, cyano, carboxyl, $C_1$-$C_6$ ester, phosphane, thiol, $C_1$-$C_6$ thioether, $OR^{40}$, and suitable pairs of adjacent R groups (R—$R^{39}$) may optionally together form part of a $C_5$ or $C_6$ aryl ring, a $Z^5$ or $Z^6$ ring, $R^{40}$ is independently selected from H, $C_1$-$C_6$ alkyl, $Z^5$ or $Z^6$ aryl, $C_1$-$C_6$ ester, poly(—$C_2O$—), amine, and $C_1$-$C_6$ alkylamine, Z—$Z^{24}$ are independently selected from C, N, P, O, and S, and $X^-$ is a pharmaceutically acceptable anion for the treatment of cancer.

The anion $X^-$ may be selected from halide, hexafluorophosphate, nitrate, and triflate.

According to a third aspect of the invention, there is provided a pharmaceutical composition, the composition including at least one compound selected from compounds of the Formula (I),

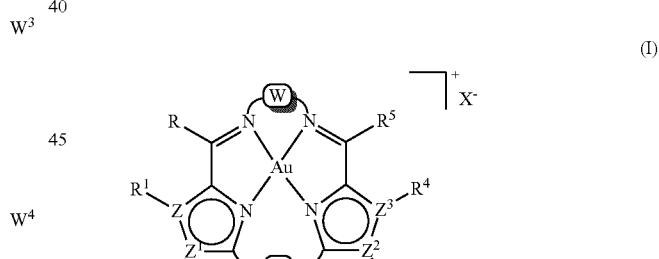

in which

W is independently selected from $W^1$, $W^2$, $W^3$, $W^4$, $W^5$,

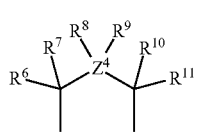

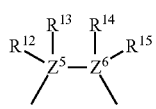

-continued

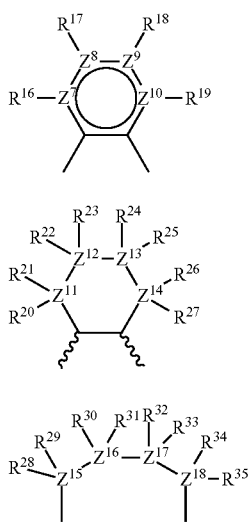

W³

W⁴

W⁵ or W represents a pair of substituents independently selected from H, $C_1$-$C_6$ alkyl, $Z^5$ or $Z^6$ aryl or $C_1$-$C_6$ amide in which the amide is optionally part of a linking chain, and the $Z^n$—$Z^{n'}$ bonds (n=4-17; n'=n+1) are optionally of any whole or partial bond order, Y is $Y^1$

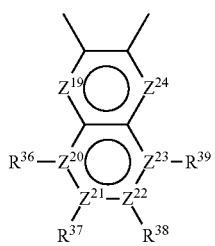

Y¹ or Y represents a pair of substituents independently selected from H, $C_1$-$C_6$ alkyl, $Z^5$ or $Z^6$ aryl, or Y is optionally a bridging structure that may comprise one or more $C_1$-$C_6$ amide, $C_1$-$C_6$ ether, or $C_1$-$C_6$ ester groups, R—$R^{39}$ are independently selected from no substituent, a lone pair of electrons, H, halogen, $C_5$-$C_6$ aryl, $C_1$-$C_{12}$ alkyl, amine, $C_1$-$C_6$ alkylamine, $C_1$-$C_6$ amide, nitro, cyano, carboxyl, $C_1$-$C_6$ ester, phosphane, thiol, $C_1$-$C_6$ thioether, $OR^{40}$, and suitable pairs of adjacent R groups (R—$R^{39}$) may optionally together form part of a $C_5$ or $C_6$ aryl ring, a $Z^5$ or $Z^6$ ring, $R^{40}$ is independently selected from H, $C_1$-$C_6$ alkyl, $Z^5$ or $Z^6$ aryl, $C_1$-$C_6$ ester, poly(—$C_2O$—), amine, and $C_1$-$C_6$ alkylamine, Z—$Z^{24}$ are independently selected from C, N, P, O, and S, and $X^-$ is a pharmaceutically acceptable anion.

The anion $X^-$ may be selected from halide, hexafluorophosphate, nitrate, and triflate.

The pharmaceutical composition may be for use in the treatment of cancer.

According to a fourth aspect of the invention, there is provided a method of treating cancer, the method including the step of administering, to a subject in need of treatment, a pharmaceutically effective amount of at least one compound selected from compounds of Formula (I),

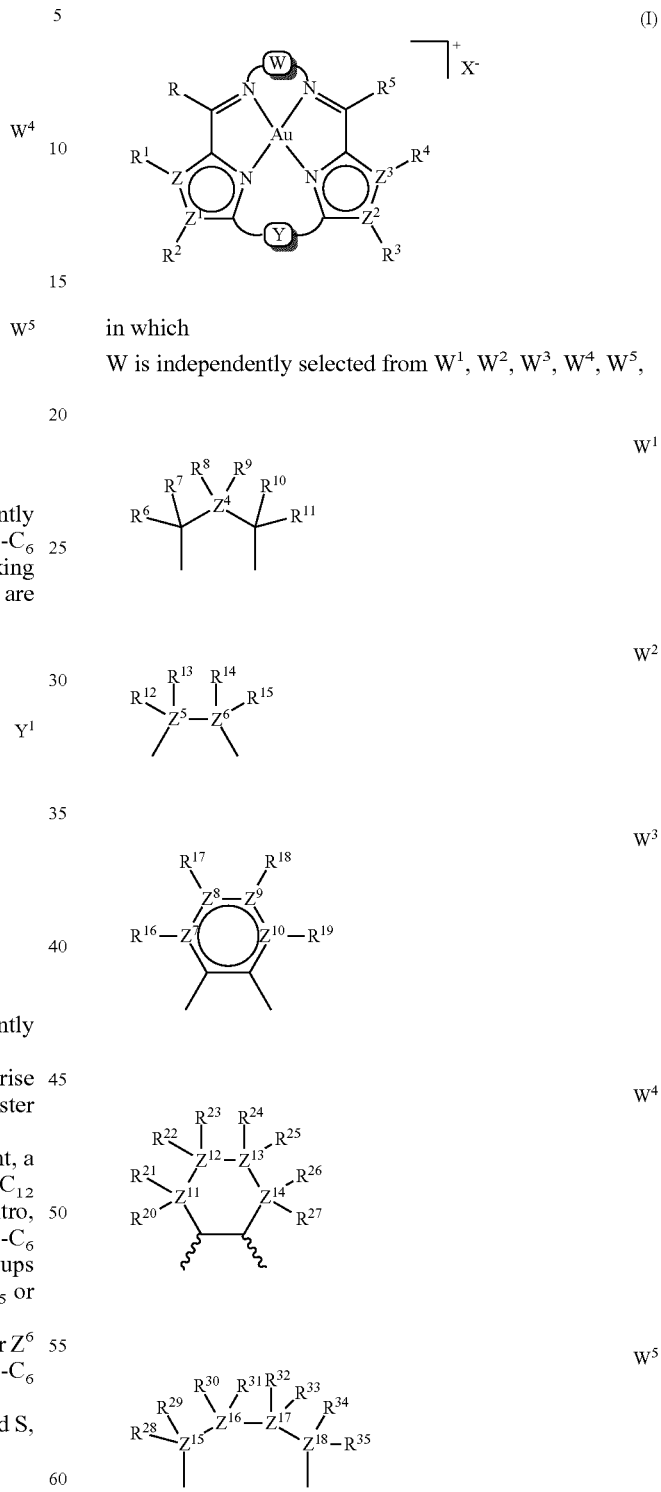

in which

W is independently selected from $W^1$, $W^2$, $W^3$, $W^4$, $W^5$, or W represents a pair of substituents independently selected from H, $C_1$-$C_6$ alkyl, $Z^5$ or $Z^6$ aryl or $C_1$-$C_6$ amide in which the amide is optionally part of a linking chain, and the $Z^n$—$Z^{n'}$ bonds (n=4-17; n'=n+1) are optionally of any whole or partial bond order, Y is $Y^1$

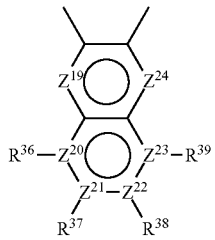

$Y^1$ or Y represents a pair of substituents independently selected from H, $C_1$-$C_6$ alkyl, $Z^5$ or $Z^6$ aryl, or Y is optionally a bridging structure that may comprise one or more $C_1$-$C_6$ amide, $C_1$-$C_6$ ether, or $C_1$-$C_6$ ester groups, R—$R^{39}$ are independently selected from no substituent, a lone pair of electrons, H, halogen, $C_5$-$C_6$ aryl, $C_1$-$C_{12}$ alkyl, amine, $C_1$-$C_6$ alkylamine, $C_1$-$C_6$ amide, nitro, cyano, carboxyl, $C_1$-$C_6$ ester, phosphane, thiol, $C_1$-$C_6$ thioether, $OR^{40}$, and suitable pairs of adjacent R groups (R—$R^{39}$) may optionally together form part of a $C_5$ or $C_6$ aryl ring, a $Z^5$ or $Z^6$ ring, $R^{40}$ is independently selected from H, $C_1$-$C_6$ alkyl, $Z^5$ or $Z^6$ aryl, $C_1$-$C_6$ ester, poly(—$C_2O$—), amine, and $C_1$-$C_6$ alkylamine, Z—$Z^{24}$ are independently selected from C, N, P, O, and S, and $X^-$ is a pharmaceutically acceptable anion.

The anion $X^-$ may be selected from halide, hexafluorophosphate, nitrate, and triflate.

According to a fifth aspect of the invention, there is provided the use of a compound selected from compounds of Formula (I) has hereinbefore described in the manufacture of a medicament for the treatment of cancer.

The invention described thus provides a new class of gold (III) bis(pyrrolide-imine) and bis(imidazolato-imine) Schiff base complexes for use as novel anticancer chemotherapeutic agents. These complexes consist of a central gold(III) ion chelated by a $N_2N'_2$ tetradentate bis(N-heterocycle-imine) type ligand. Upon coordination of the gold(III) ion, the two pyrrole-type nitrogen atoms (N—H groups) are deprotonated, giving the ligand an overall charge of −2. The metal ion complex therefore has an overall charge of +1; hence the chelates are associated with an anion. The complexes were designed to be predominantly planar which allows the gold (III) chelates to intercalate between DNA base pairs. The overall charge on the cation allows for favorable electrostatic interactions with the negatively charged phosphate backbone of the DNA double helix. The molecular target for the gold (III) complexes is thus DNA (and possibly also related nucleotides). Once the drug has intercalated genomic DNA in cells, it prevents DNA transcription (and thus cell growth), separation of daughter chromatids during mitosis (and thus cell division), and/or maintenance of the DNA duplex by interfering specifically with the normal functioning of either of the essential enzymes topoisomerase I or topoisomerase II. Compound 1.1a, for example, acts as a topoisomerase II poison at low concentrations and an inhibitor of the enzyme at high concentrations (topoisomerase II is critical for cell replication, being responsible for the decatenation of daughter chromatids during mitosis). Compound 1.1$Y^1$a (KA_Aumac- roPr), on the other hand, acts as a catalytic inhibitor of both topoisomerase I and topoisomerase II.

The gold(III) chelates of the invention are novel in design and structure and their mode of synthesis is novel. The complexes are readily crystallized, easily purified, and have been fully characterized. The complexes exhibit a highly specific mode of action (all of the compounds target topoisomerase II and some also target topoisomerase I). The most active compound shows good activity (mean $GI_{50}$=7 µM; mean $IC_{50}$=20 µM) against multiple cancer cell lines over the full NCI-60 screen. The mechanism of action has been proven to be dependent on the presence of the gold(III) ion since the metal-free complexes are inactive.

In preferred embodiments of the invention, Y may represent two hydrogen atoms or Y. For example, Y may be $Y^1$, and $Z^{19}$ and $Z^{24}$ may be N. In another preferred embodiment $Z^{20}$-$Z^{23}$ may be C.

The groups R—$R^5$ may be selected from H, $C_1$-$C_3$ alkyl, O—$C_1$-$C_3$ alkyl, hydroxyl and halogen. In particular the $C_1$-$C_3$ alkyl group may be a methyl group, the O—$C_1$-$C_3$ alkyl group may be an O-ethyl group and the halogen may be chlorine.

In other preferred embodiments W may be selected from $W^1$, $W^2$, $W^3$ or $W^4$. The groups $R^6$-$R^{27}$ may then be selected from H, $C_1$-$C_3$ alkyl, O—$C_1$-$C_3$ alkyl and halogen. The $C_1$-$C_3$ alkyl group may be a methyl group, the O—$C_1$-$C_3$ alkyl may be an O-ethyl group and the halogen may be chlorine.

More preferred compounds are compounds selected from:
2,2'-{propane-1,3-diylbis[nitrilo(E)methylylidene]}bis(pyrrol-1-ido)gold(III) chloride,
2,2'-{(2,2-dimethylpropane-1,3-diyl)bis[nitrilo(E)methylylidene]}bis(pyrrol-1-ido)gold(III) chloride,
2,2'-{(2-hydroxypropane-1,3-diyl)bis[nitrilo(E)methylylidene]}bis(pyrrol-1-ido)gold(III) hexafluorophosphate (V),
2,2'-{(2-ethoxypropane-1,3-diyl)bis[nitrilo(E)methylylidene]}bis(pyrrol-1-ido)gold(III) hexafluorophosphate (V),
2,2'-{(2-chloropropane-1,3-diyl)bis[nitrilo(E)methylylidene]}bis(pyrrol-1-ido)gold(III) hexafluorophosphate (V),
2,2'-{ethane-1,2-diylbis[nitrilo(E)methylylidene]}bis(pyrrol-1-ido)gold(III) hexafluorophosphate(V),
2,2'-{(2S)-propane-1,2-diylbis[nitrilo(E)methylylidene]}bis(pyrrol-1-ido)gold(III) hexafluorophosphate(V),
2,2'-{(1R,2R)-cyclohexane-1,2-diylbis[nitrilo(E)methylylidene]}bis(pyrrol-1-ido)gold(III) hexafluorophosphate (V),
2,2'-{(1S,2S)-cyclohexane-1,2-diylbis[nitrilo(E)methylylidene]}bis(pyrrol-1-ido)gold(III) hexafluorophosphate (V),
2,2'-{cyclohexane-1,2-diylbis[nitrilo(E)methylylidene]}bis(pyrrol-1-ido)gold(III) hexafluorophosphate(V)
2,2'-{(4-methylbenzene-1,2-diyl)bis[nitrilo(E)methylylidene]}bis(pyrrol-1-ido)gold(III) nitrate(V),
4,4'-{propane-1,3-diyl)bis[nitrilo(E)methylylidene]}bis(5-methylimidazol-1-ide)gold(III) hexafluorophosphate(V),
4,4'-{(2,2-dimethylpropane-1,3-diyl)bis[nitrilo(E)methylylidene]}bis(5-methylimidazol-1-ide)gold(III) hexafluorophosphate(V),
{12,13-dihydro-14H-6,9:17,20-diepimino[1,6]diazacyclo-heptadecino[12,13-β]quinoxalinato}gold(III) hexafluorophosphate(V),
{12,14-dihydro-13,13-dimethyl-6,9:17,20-diepimino[1,6]diazacyclo-heptadecino[12,13-β]quinoxalinato}gold(III) hexafluorophosphate(V), {12,13,14,15-tetrahydro-6,9:18,21-diepimino[1,6]diazacy-cloctadecino[12,13-b]quinoxalinato}gold(III) hexafluorophosphate(V), and {13-chloro-12,14-dihydro-6,9:17,20-diepimino[1,6]diaza-cyclo-heptadecino[12,13-β]quinoxalinato}gold(III) hexafluorophosphate(V).

The invention extends further to a pharmaceutical composition comprising at least one compound as hereinbefore described.

The invention extends to a method of preparing a compound of Formula (I), which includes the steps of condensing a diamine of the general formula A

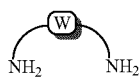

A simultaneously or consecutively with a carbonyl compound selected from compounds of the general formula B, C and D

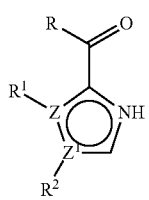

B

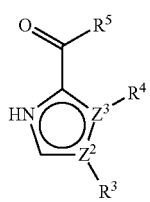

C

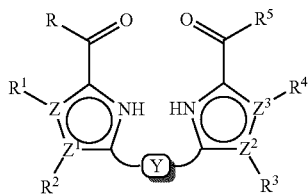

D to produce a diimine Schiff base of the general formula E or F

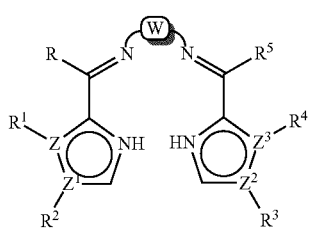

E

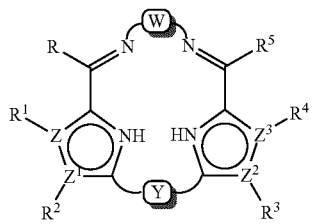

F and reacting the diimine of general formula E or F with a tetraalkylammonium tetrahaloaurate(III) to produce the gold (III) compound of the general Formula (I) in which W, Y, R, Z and X are as hereinbefore described.

The invention extends further to a method of preparing a compound of general Formula (I), which includes the step of reacting a carbonyl compound of the general formula D

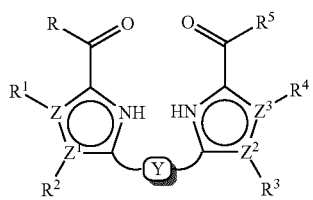

D with a tetraalkylammonium tetrahaloaurate(III) and a diamine to produce the compound of general Formula (I) in which W, Y, R, Z and X are as hereinbefore described. The tetraalkylammonium tetrahaloaurate(III) may be tetrabutylammonium tetrachloroaurate(III). The butyl group may be a t-butyl group.

The method may include reacting the diamine with the tetraalkylammonium tetrahaloaurate (III) in the presence of a salt selected from halides, hexafluorophosphates, nitrates, and triflates to produce the corresponding compound of Formula (I) in which X⁻ is the corresponding anion. In particular, the salt may be a tetraalkylammonium hexafluorophosphate such as tetra-t-butylammonium hexafluorophosphate.

Where the compound of Formula (I) is a chloride the method may include the further step of reacting the compound of Formula (I) in which X⁻ is chloride with a salt selected from halides other than chloride, hexafluorophosphates, nitrates, and triflates to produce a compound of Formula (I) in which X⁻ is the anion of the said salt.

The invention extends to a method of preparing a 2-substituted 1,3-diamine intermediate of the general formula A¹

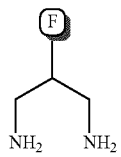

A¹ or its dihydrochloride salt, in which F is selected from F¹ or halogen,

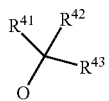

in which
R$^{41}$-R$^{43}$ are independently selected, H, halogen, Z$^5$ or Z$^6$ aryl, C$_1$-C$_{12}$ alkyl, C$_1$-C$_6$ alkylamine, C$_1$-C$_6$ amide, carboxyl, C$_1$-C$_6$ ester or OR$^{40}$,
R$^{40}$ is as hereinbefore described, or
suitable pairs of adjacent R groups (R$^{41}$-R$^{43}$) optionally together form part of a C$_5$ or C$_6$ aryl ring, or
F is R$^{44}$, and
R$^{44}$ is independently selected from H, C$_1$-C$_6$ alkyl, Z$^5$ or Z$^6$ aryl, C$_1$-C$_6$ ester, poly(—C$_2$O—), amine, C$_1$-C$_6$ alkylamine, and C$_1$-C$_6$ amide or a Z$^5$ or Z$^6$ ring, and Z$^5$ and Z$^6$ are as hereinbefore described,
the method including the steps of converting the hydroxyl group of 2,2,12,12-t-methyl-3,11-dioxo-4,10-dioxa-5,9-diazatridecan-7-ol to the group F.

The invention extends to bis(pyrrole-imine) ligands selected from:
2-ethoxy-N,N-bis[(E)-1H-pyrrol-2-ylmethylidene]propane-1,3-diamine, and
2-chloro-N,N-bis[(E)-1H-pyrrol-2-ylmethylidene]propane-1,3-diamine.

The invention extends further to a method for the preparation of tetrabutylammonium tetrachloroaurate, [Bu$_4$N][AuCl$_4$], the method including the step of extracting [Bu$_4$N][AuCl$_4$] from a mixture using an organic solvent-extraction purification step to produce an acid-free, crystalline [Bu$_4$N][AuCl$_4$]. The method may include reacting an aqueous solution of H[AuCl$_4$] and [Bu$_4$N][HSO$_4$] to produce the mixture and extracting the [Bu$_4$N][AuCl$_4$] from the mixture with the organic solvent.

The invention is now illustrated, by way of example, with reference to the following examples.

FIG. 1 is a structural representation of Auranofin.

FIG. 2 is a partially labeled thermal ellipsoid diagram of the X-ray crystal structure of MA_AuPr. Ellipsoids are rendered as 50% probability surfaces; H atoms are of an arbitrary radius.

FIG. 3 is a partially labeled thermal ellipsoid diagram of the X-ray crystal structure of KA_AumacroPr. Ellipsoids are rendered as 50% probability surfaces; H atoms are of an arbitrary radius.

FIG. 4 is a partially labeled thermal ellipsoid diagram of the X-ray crystal structure of A_AuMelmPr. Ellipsoids are rendered as 30% probability surfaces; H atoms are of an arbitrary radius.

Figure 17:
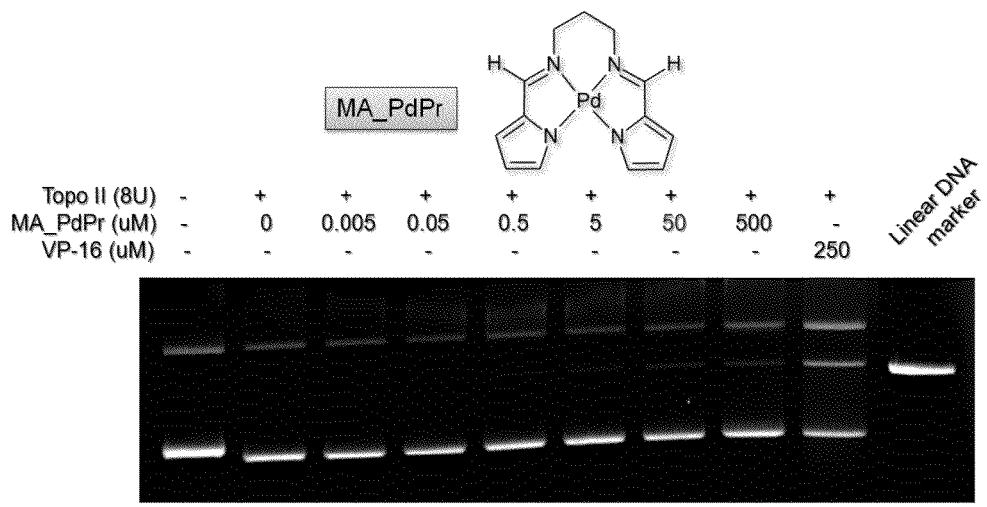

FIG. 17 is a photograph of an EB gel showing the diminished activity of MA_PdPr (the Pd$^{2+}$ analogue of MA_AuPr) against topoisomerase II compared to the chemotherapeutic agent VP-16 (etoposide), which is specifically a topoisomerase II poison. There is evidence of DNA-cleavage induction in the presence of topoisomerase II at 50 μM concentration (a 100-fold weaker effect than the gold(III) complex).

Figure 18:
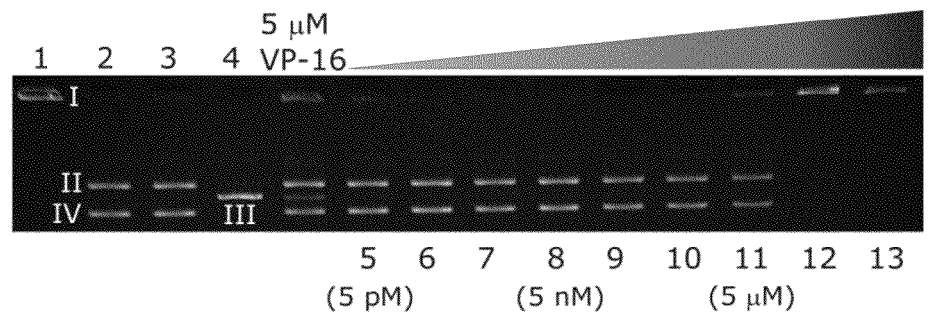
Figure 18:
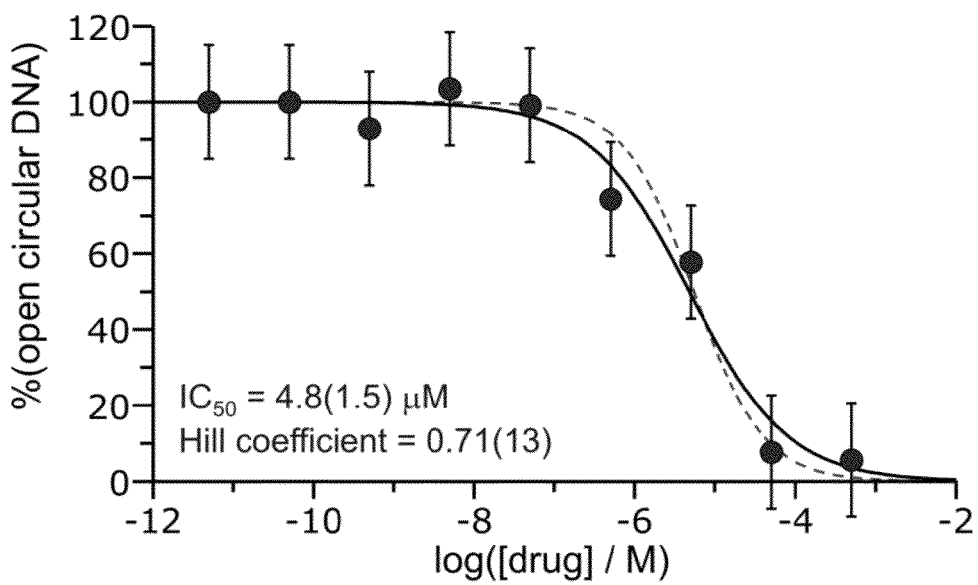

FIG. 18 is a photograph of an agarose gel electrophoresis topoisomerase II (topo II) DNA cleavage assay (66 ng kinetoplast DNA, 4 U topo II) as a function of the concentration of KA_AumacroPr (complex 1.1Y$^1$a) (top) and a graph of a standard dose-response function fit of the experimental titration data (top gel) with (solid line) and without (dashed line) a Hill coefficient. The maximum ESD from triplicate measurements is shown (15%). Lanes 1-4 of the gel contain catenated DNA (no topo II), decatenated DNA (topo II present), decatenated DNA (solvent control), and linear DNA, respectively. The lane marked VP-16 contained DNA, topo II, and etoposide (VP-16). Band labels: I, catenated DNA; II, open-circular (OC) DNA; III, linear DNA; IV, closed-covalently circular (CCC) DNA. Lanes 5-13 included compound 1.1Y$^1$a from 5 nM to 500 nM in 10-fold concentration increments, respectively.

Figure 19:
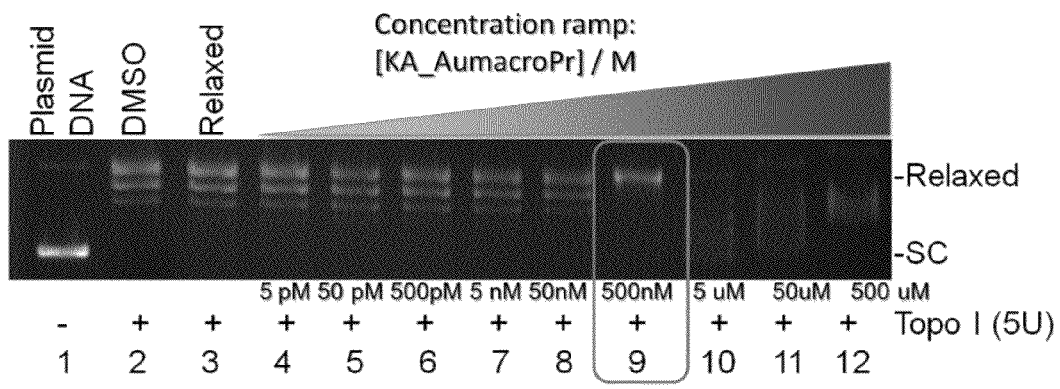

FIG. 19 is a photograph of a gel showing the inhibition of human topoisomerase I by KA_AumacroPr as determined by supercoiled plasmid DNA relaxation assay (agarose gel electrophoresis).

Lanes 2-12 have 5U of topoisomerase I. The enzyme fully relaxes supercoiled (SC) DNA in lanes 3-8 for KA_AumacroPr concentrations ranging from 0-50 nM. At concentrations from 500 nM-500 μM, topoisomerase I exhibits abnormal and incomplete substrate relaxation.

Figure 20:
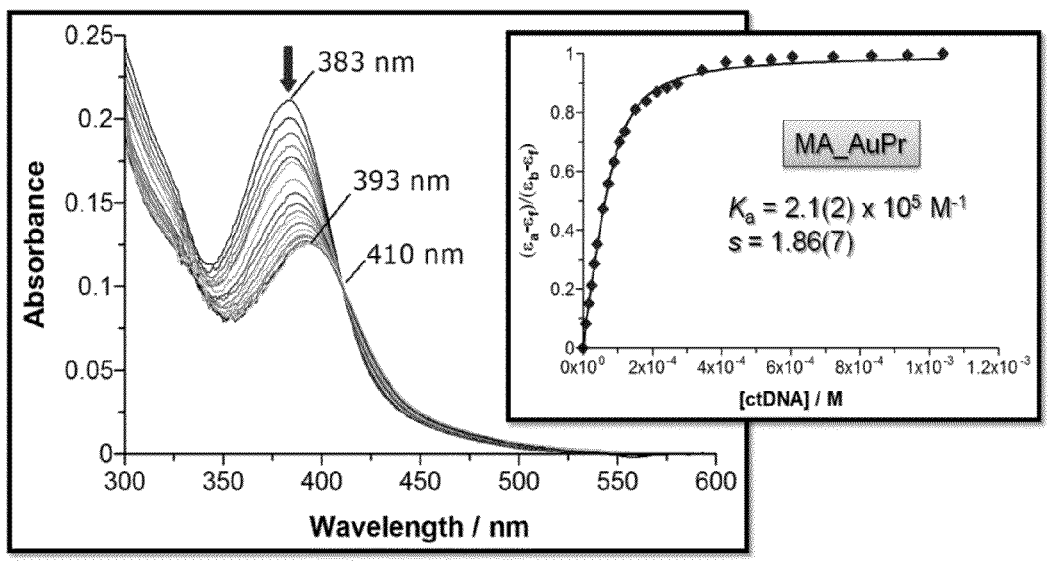

FIG. 20 is a graph of the titration of MA_AuPr (1.1a) with calf-thymus DNA in aqueous pH 7 phosphate buffer at 37° C. The data indicate that compound 1.1a is a DNA intercalator.

Figure 21:
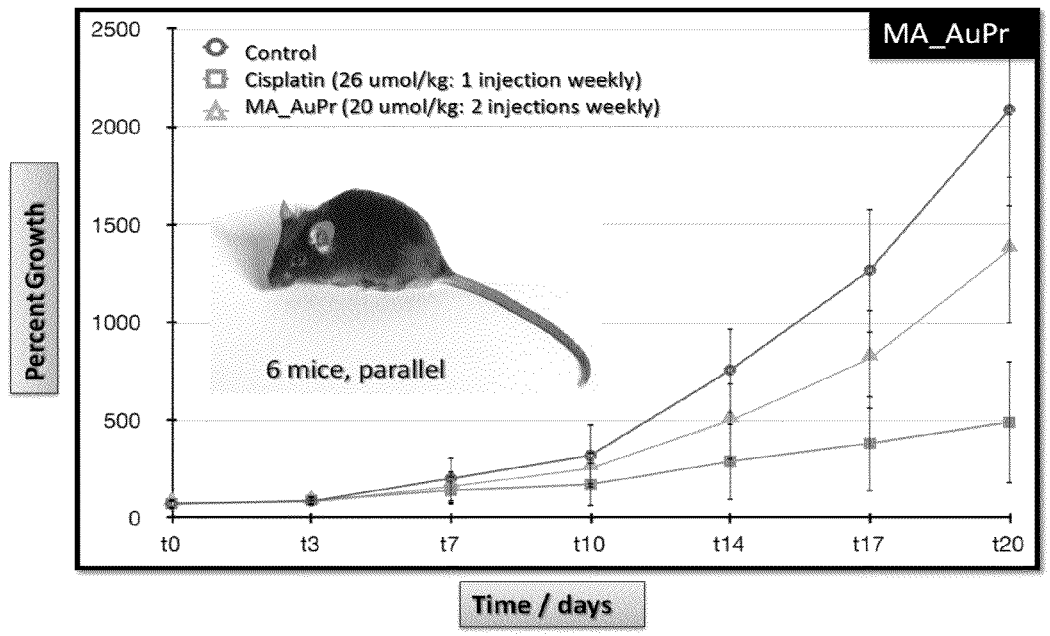

FIG. 21 is a graph of 3LL tumor growth in black mice (mean data for 6 subjects) as a function of time and type of anticancer drug. MA_AuPr was administered at a dose of 20 µmol/kg twice weekly and cisplatin at a dose of 26 µmol/kg once weekly. Untreated mice were the control.

Figure 22:
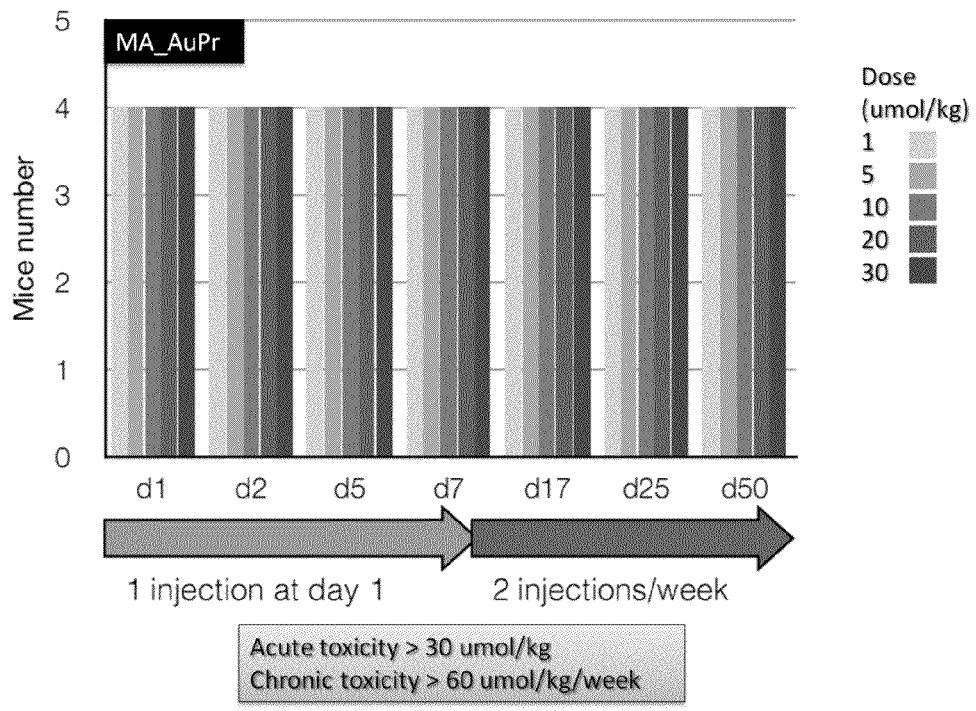

FIG. 22 is a plot showing the mouse survival data as a function of metallodrug dose for MA_AuPr. The graph plots the survival of five groups of four mice on drug concentrations ranging from 1 to 30 µmol/kg for the displayed injection protocols.

Figure 23:
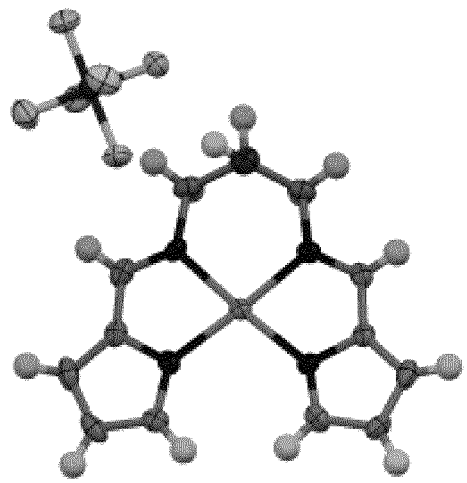
Figure 23:
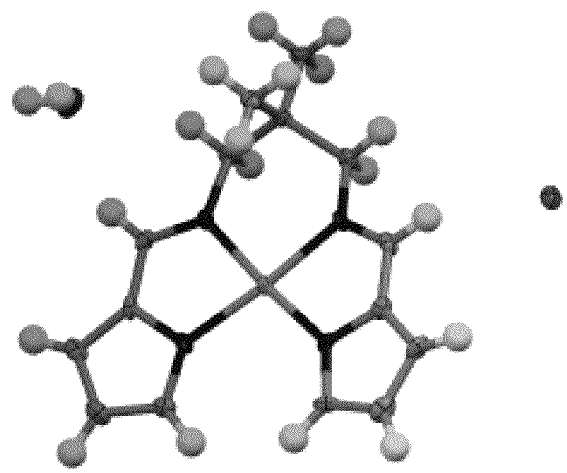

FIG. 23 is a picture of the crystal structures of (A) $C_{13}H_{14}AuF_6N_4OP$ and (B) $C_{15}H_{19}AuClN_4O_{0.5}$.

Figure 24:
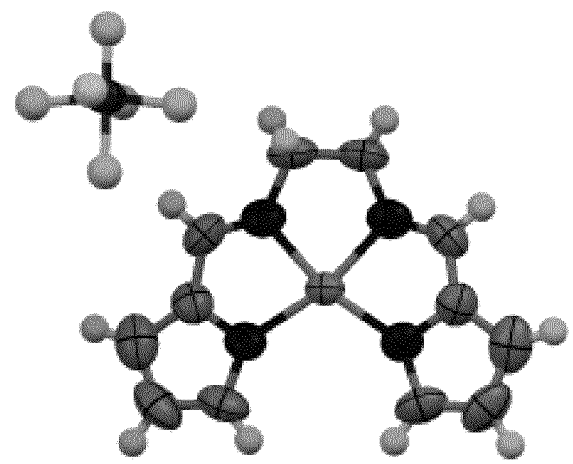
Figure 24:
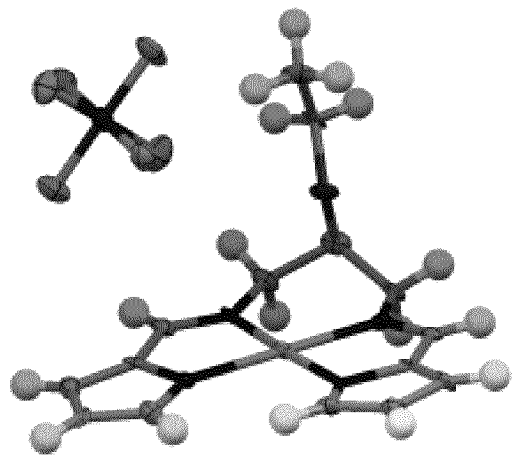

FIG. 24 is a picture of the crystal structures of (C) $C_{12}H_{12}AuF_6N_4P$ and (D) $C_{15}H_{17}AuF_6N_4OP$.

Figure 25:
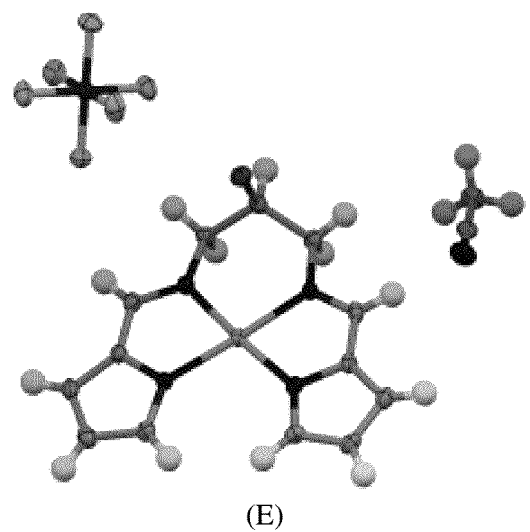
Figure 25:
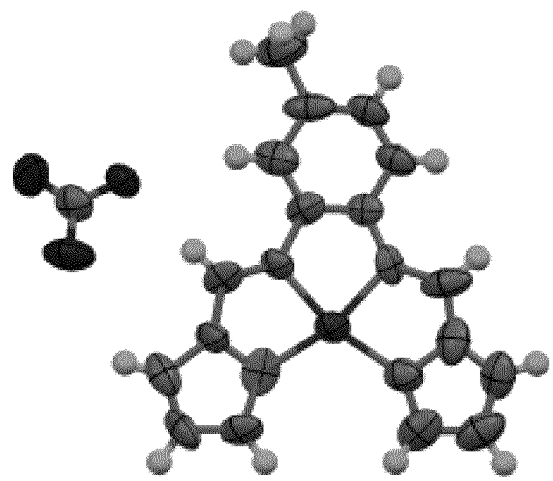

FIG. 25 is a picture of the crystal structures of (E) $C_{15}H_{16}AuClF_6N_5P$, and (F) $C_{17}H_{14}AuF_6N_5O$.

EXAMPLE 1

In Vitro Anti-Cancer Tests

The gold(III) complexes of this invention were screened by the National Cancer Institute (NCI, USA) against their panel of 60 different human cancer cell lines. These screens initially entail a one-dose test for the compound at a high concentration (10 µM; e.g. FIGS. 5, 6 and 7). Compounds with a good cytotoxicity profile in the one-dose screen are then subjected to a five-dose screen for the full panel of sixty human cancer cell lines (the so-called 5-dose NCI-60 screen). In the full five-dose screen, the compound concentration is varied in five doses from $10^{-8}$ M to $10^{-4}$ M in order to establish a dose-response function of percentage cell growth versus the concentration of the test agent. The latter data permits determination of several key parameters indicative of a compound's cytotoxicity, namely, the $GI_{50}$, $IC_{50}$, and $LC_{50}$ values for the test agent (these are the concentrations at which 50% growth inhibition, total growth inhibition, and 50% cell death occur, respectively). These data from 5-dose NCI-60 screens are summarized in Scheme 7 for selected chelates of this invention (by way of illustration). Similar data will shortly be available for compounds $1.1Y^1b$ and $1.5Y^1a$ as these derivatives are in 5-dose screens currently at the NCI.

Figure 1:
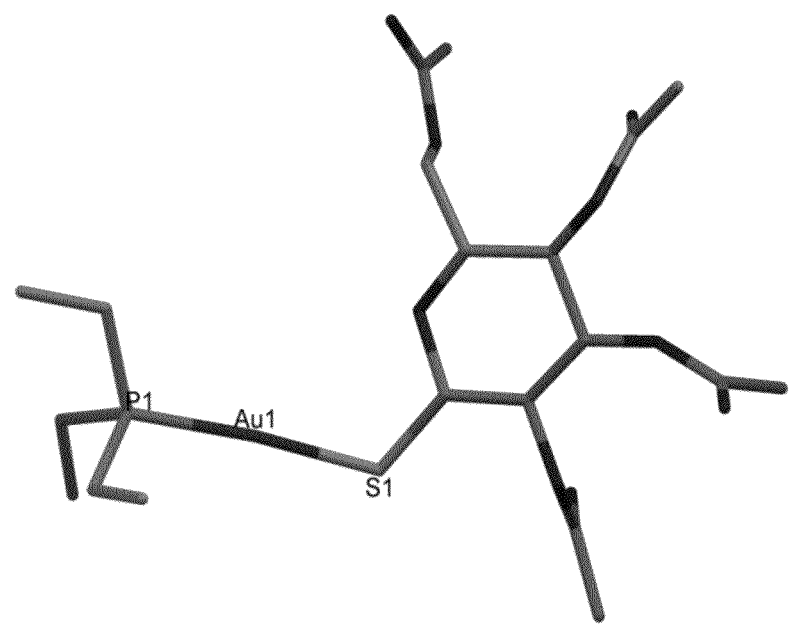
Figure 2:
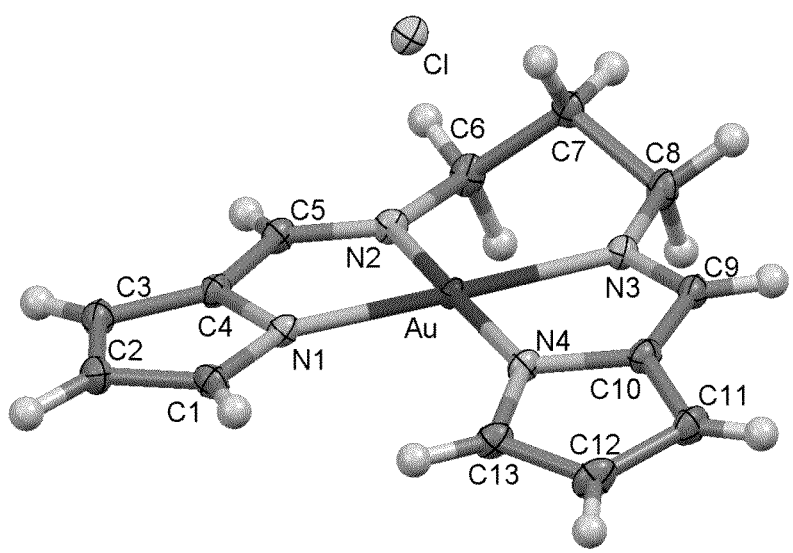
Figure 3:
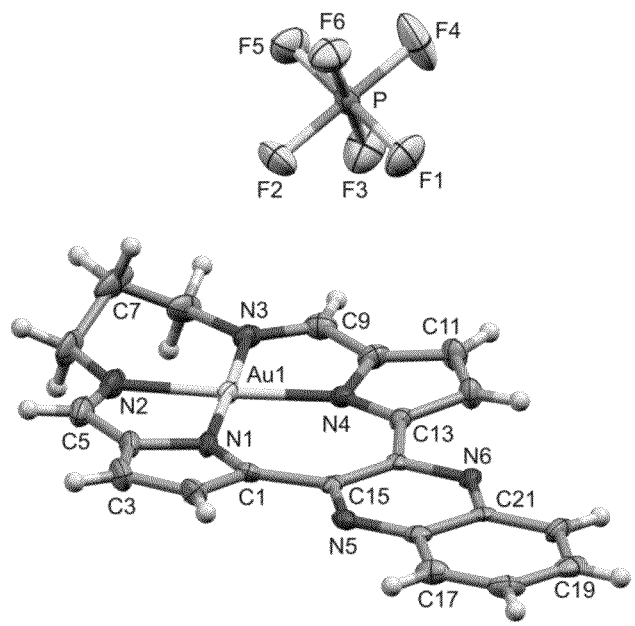
Figure 4:
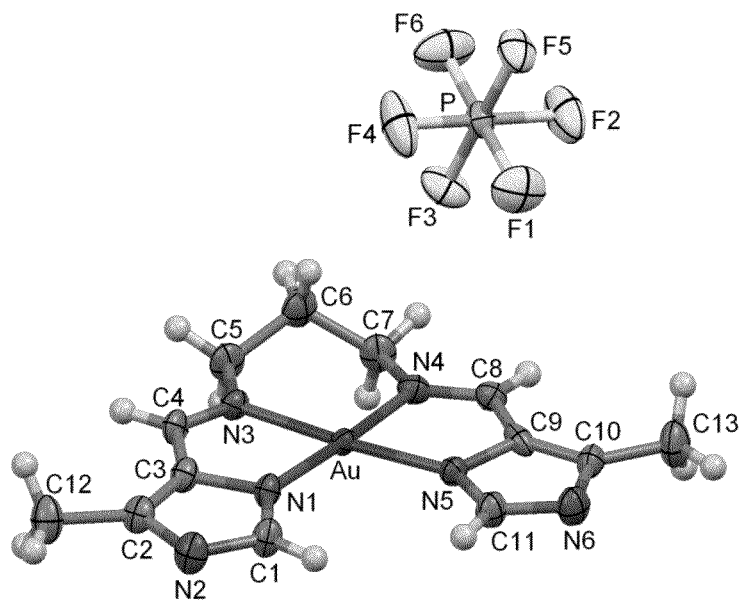
Figure 5:
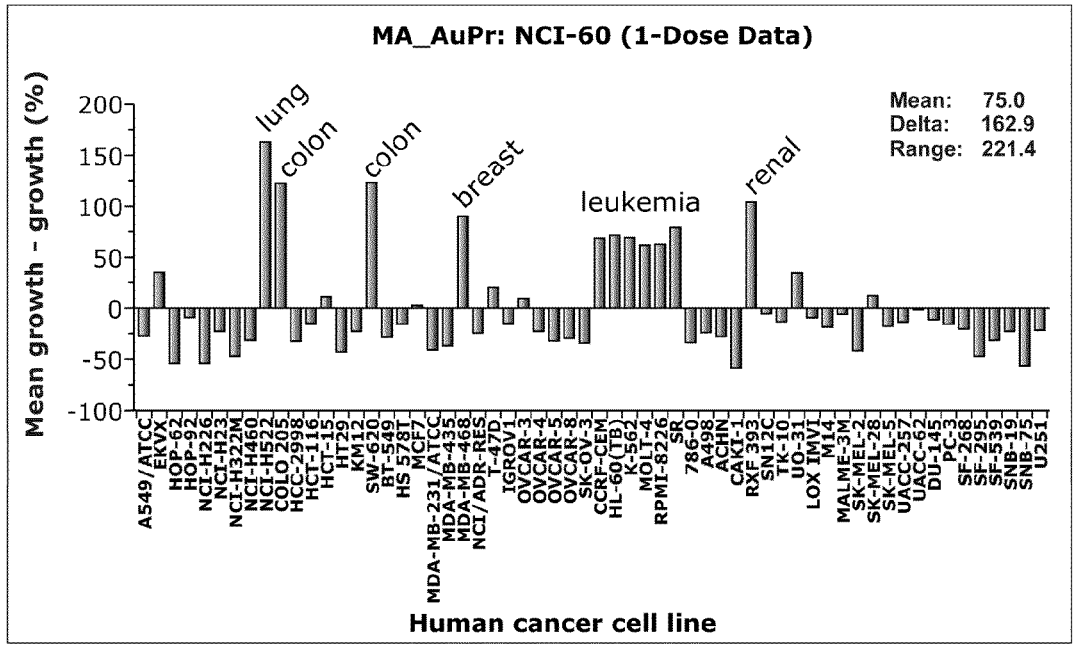
FIG. 5 is a chart of the single-dose screening results for MA_AuPr over 60 human cancer cell lines. A negative growth percent is favorable and shows up as a positive bar on the graph.
Figure 6:
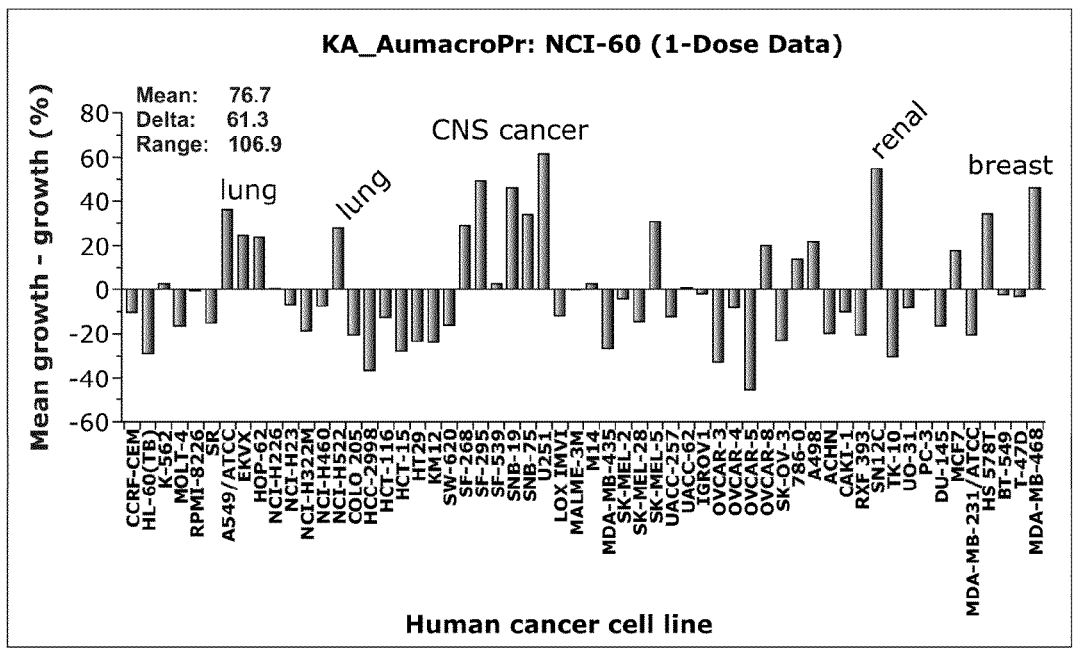
FIG. 6 is a chart of the single-dose screening results for KA_AumacroPr over 60 human cancer cell lines. A negative growth percent is favorable and shows up as a positive bar on the graph.
Figure 7:
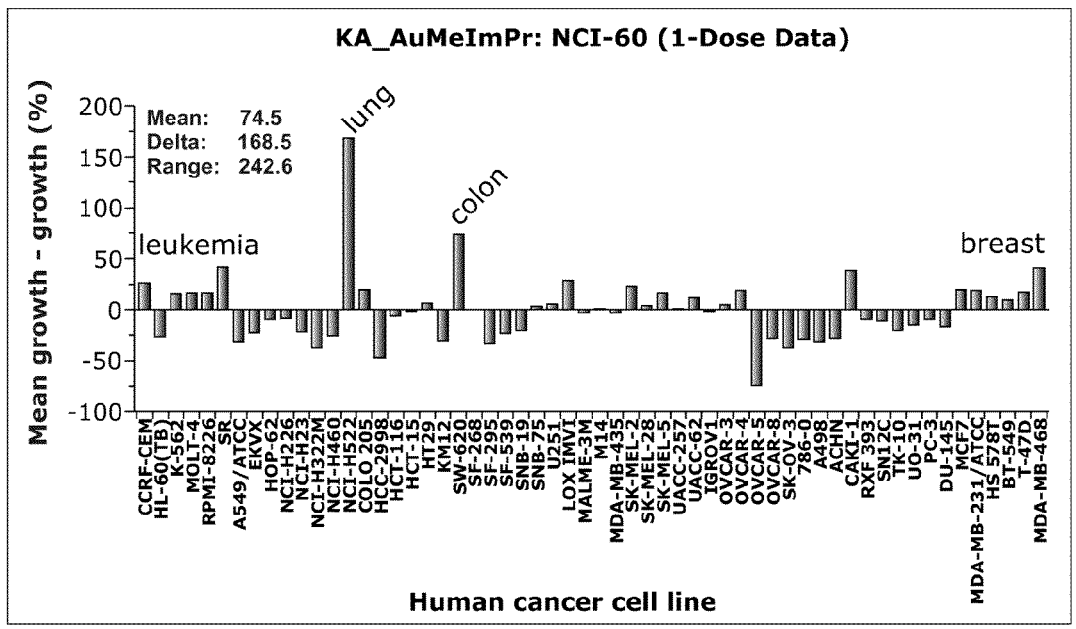
FIG. 7 is a chart of the single-dose screening results for KA_AuMelmPr over 60 human cancer cell lines. A negative growth percent is favorable and shows up as a positive bar on the graph.

The results of one-dose NCI-60 screens are noteworthy and merit some discussion as they quickly indicate activity profiles, cell-line specificity, and general cytotoxicity for the test agents across multiple human cancer cell lines. FIGS. 5, 6, and 7 set out the one-dose screening results for MA_AuPr (FIG. 5), KA_AumacroPr (FIG. 6), and KA_AuMelmPr (FIG. 7) obtained by the NCI. These three compounds are the parent derivatives that are representative of the three new types of gold(III) Schiff base chelate relevant to this invention. All other compounds synthesized as part of this invention have been similarly analyzed.

The preliminary cell screening data indicated that the three classes of compounds are inherently more toxic towards some cancer cell lines than others. This suggests that the compounds of the invention are not merely general poisons, but in fact agents with some tumor specificity and specific cellular mechanisms of action. From FIGS. 5, 6 and 7, leukemia, breast, and colon cancer cell lines are inherently more susceptible to the cytotoxic action of MA_AuPr. Breast and leukemia cell lines were, as a group, the most sensitive to KA_AuMelmPr while the macrocyclic derivative KA_AumacroPr showed good cytotoxicity for the majority of the cell lines constituting the groups: (i) non-small lung cancer, (ii) central nervous system cancer, (iii) renal carcinoma, and (iv) breast cancer.

Figure 8:
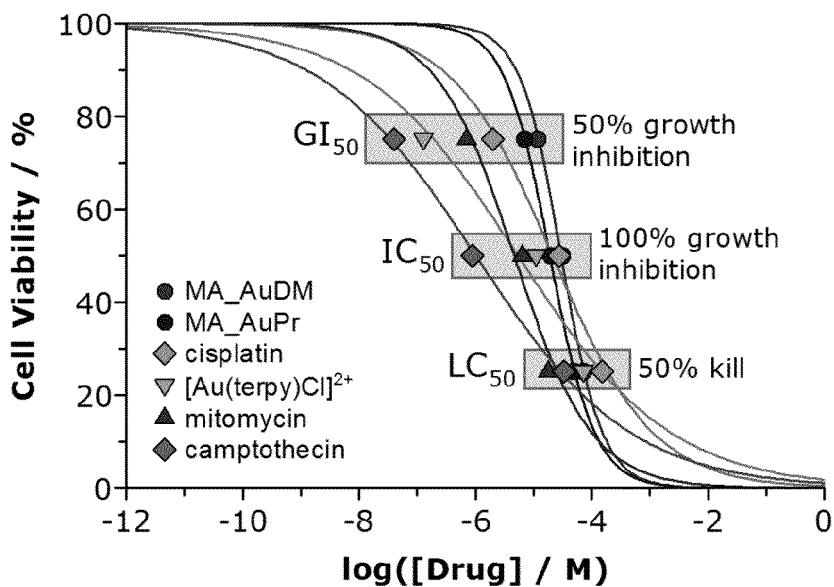
FIG. 8 is a graph of the dose-response curves for three commercial anticancer drugs (cisplatin, mitomycin, camptothecin) and three Au(III) chelates. The more abrupt the curve, the harder the dose-response function.
Figure 9:
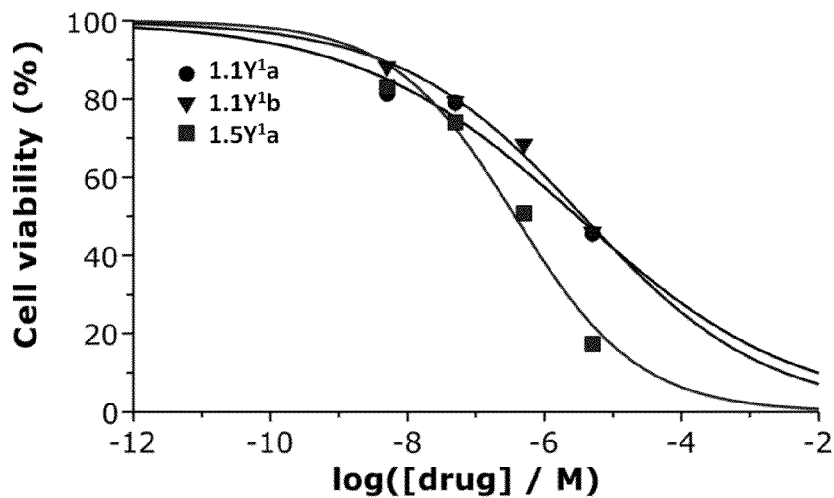
FIG. 9 is a graph of the dose-response curves (HeLa cells, pH 7.0, 37° C.) for three macrocyclic Au(III) chelates. IC$_{50}$ values for the complexes against HeLa cells obtained from the least squares data fits (graph) are given in the 3$^{rd}$ column of the table.

Complexes 1.1a, 1.1b, and $1.1Y^1b$ were selected by the NCI for a five-dose screen against the full panel of 60 different human cancer cell lines to establish $IC_{50}$ values and other parameters. Complex 1.1c (with a hydroxyl group in the propyl bridge, MA_AuOH) was not sufficiently active in cell cultures to warrant a five-dose screen. The Applicant is of the opinion that cancer cells may have an active defense mechanism against 1.1c, e.g., an efflux pump or derivatization to an inactive form. The hydroxyl group is clearly implicated in the inactivity of the compound because 1.1a which lacks the hydroxyl group is highly active. A summary of the average cytotoxicity data over 60 human cancer cell lines for 1.1a-1.1c and comparison with selected commercial and patented cytotoxic agents is shown in Scheme 7. Dose-response curves for three commercial anticancer drugs (cisplatin, mitomycin, camptothecin) and three Au(III) chelates are shown in FIG. 8. The more abrupt the curve, the harder the dose-response function. FIG. 9 shows dose-response curves obtained with HeLa cells incubated with the macrocyclic gold(III) complexes $1.1Y^1a$, $1.1Y^1b$, and $1.5Y^1a$ at 37° C. The data indicate that the complex with the butyl chain as the bridging group W (complex $1.5Y^1a$) has very good cytotoxicity with a sub-micromolar $IC_{50}$ value of 370 nM; complexes $1.1Y^1a$ and $1.1Y^1b$ were also cytotoxic and had $IC_{50}$ values of ca. 3 µM.

Scheme 7
Summary of the average cytotoxicity data over 60
human cancer cell lines for 1.1a-c and comparison with
selected commercial and patented cytotoxic agents

| Drug | $GI_{50}$ (µM) | TGI or $IC_{50}$ (µM) | $LC_{50}$ (µM) |
|---|---|---|---|
| MA_AuOH (*) | >100 | >100 | >100 |
| MA_AuDM (*) | 12 | 31 | 72 |
| MA_AuPr (*) | 7(1) | 20(3) | 49(5) |
| cis-[PtCl$_2$(NH$_3$)$_2$] | 2 | 27 | >100 |
| (Au$^{III}$(terpy)Cl]Cl$_2$ | 0.13 | 11 | 73 |
| Mitomycin | 0.71 | 6.5 | 18 |
| Camptothecin | 0.04 | 0.89 | 33 |

(*): This work.

The mean cytotoxicity data summarized in Scheme 7 were compiled over 60 human cancer cell lines from the NCI database. The experimental parameters $GI_{50}$, $IC_{50}$, and $LC_{50}$, are mean concentrations at which 50% growth inhibition, 100% (total) growth inhibition, and 50% cell death occur, respectively. The data show that MA_AuPr is somewhat more cytotoxic than cisplatin and carboplatin when comparing the $IC_{50}$ and $LC_{50}$ values. The dose-response curves for the bis (pyrrolide-imine) chelates of the invention are steeper, or harder, than those of all the compounds compared in Scheme 7. Of the other drugs shown, only mitomycin (a powerful organic DNA alkylating and cross-linking agent) exhibits a comparably steep mean dose-response function.

The important features to note from the data in Scheme 7 and FIGS. 8 and 9 are the following: (i) MA_AuPr has a lower $LC_{50}$ value than the other Pt(II) and Au(III) compounds and a comparable $LC_{50}$ value to camptothecin (a potent topoisomerase I poison). (ii) MA_AuPr has a better $IC_{50}$ value than cisplatin and carboplatin. The hard dose-response function of MA_AuPr means that the therapeutic dose in vitro has a narrow window. Thus, 50% growth inhibition, on average, requires a relatively high concentration of the compound (7 µM). However, only a 7-fold increase in concentration to 49 µM effects a 50% cell kill (again on average, and over the full 60 cell lines). In contrast, a potent drug such as camptothecin requires an 825-fold increase in concentration (from 40 nM to 33 µM) to achieve the same effect.

The three Au(III) macrocycles developed and tested to date (FIG. 9) exhibit the best cytotoxicity of all the compounds examined (at least in the HeLa cell line) with softer dose-response profiles more akin to commercial natural product drugs like camptothecin. In particular, the $GI_{50}$ values for the three compounds $1.1Y^1a$, $1.1Y^1b$, and $1.5Y^1a$ are all around 100 nM. Complex $1.5Y^1a$ has a particularly attractive dose-response profile that is better than that of camptothecin (FIG. 8) because the $LC_{50}$ value is <10 µM (i.e. about one-third of camptothecin's $LC_{50}$ value).

Further, the in vitro data suggest that if general and organ-specific toxicity of MA_AuPr is not high in an animal model, i.e., micromolar concentrations of the compound are well-tolerated in vivo, then this new class of Au(III) compounds has a fundamental activity profile unlike any other compounds currently in use or in trials. Most importantly, this new class of compounds might be useful for completely clearing stubborn tumours or cisplatin-resistant tumours (complex $1.5Y^1a$ is clearly an extremely promising candidate for such a role). Small structural changes to the basic ligand structure (compare MA_AuPr with MA_AuDM and MA_AuOH) clearly dramatically alter the mean cytotoxicity profile of the compound. This suggests a strong link between structure and activity and that the synthesis and screening of other derivatives of the basic bis(pyrrolide-imine) chelate system are likely to enhance the cytotoxicity of the lead compound and afford $GI_{50}$ and $IC_{50}$ values in the same range as commercially viable drugs such as mitomycin or camptothecin.

Figure 10:
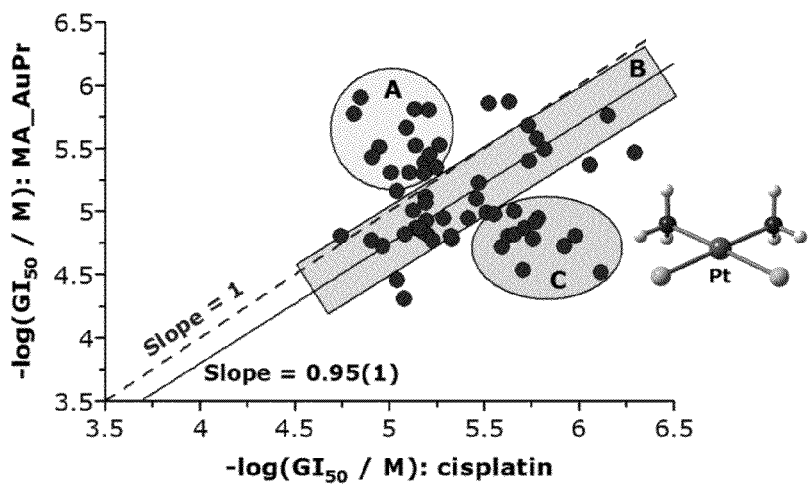
FIG. 10 is a plot of –log(GI$_{50}$/M) for MA_AuPr versus the equivalent data for cisplatin.

FIG. 10 shows a plot of $-\log(GI_{50}/M)$ for MA_AuPr versus the equivalent data for cisplatin.

The plot in FIG. 10 shows that, on average, the chelate MA_AuPr exhibits 95% of the growth inhibition activity of cisplatin. The region marked A on the plot accounts for ca. 25% of the cancer cell lines tested and confirms that a sizeable fraction of cancer cell lines are either equivalently susceptible or significantly more susceptible to MA_AuPr than to cisplatin. The complex MA_AuDM shows a similar activity profile to that of MA_AuPr (with 91% of the activity of cisplatin on average and around 12% of the cell lines being more susceptible to this Au(III) drug than to cisplatin). These data demonstrate that the new class of bis(pyrrolide-imine) Au(III) chelates of the invention should compete favorably with cisplatin or, in fact, be better for around 25% of human cancers. We have yet to test the Au(III) macrocycles $1.1Y^1a$, $1.1Y^1b$, and $1.5Y^1a$ in the full 5-dose NCI-60 screens. However, complex $1.1Y^1b$ has just entered this phase of the screening process and is expected to perform better than MA_AuPr if its performance in the HeLa cell line is an indicator of its more general cytotoxicity.

Figure 11:
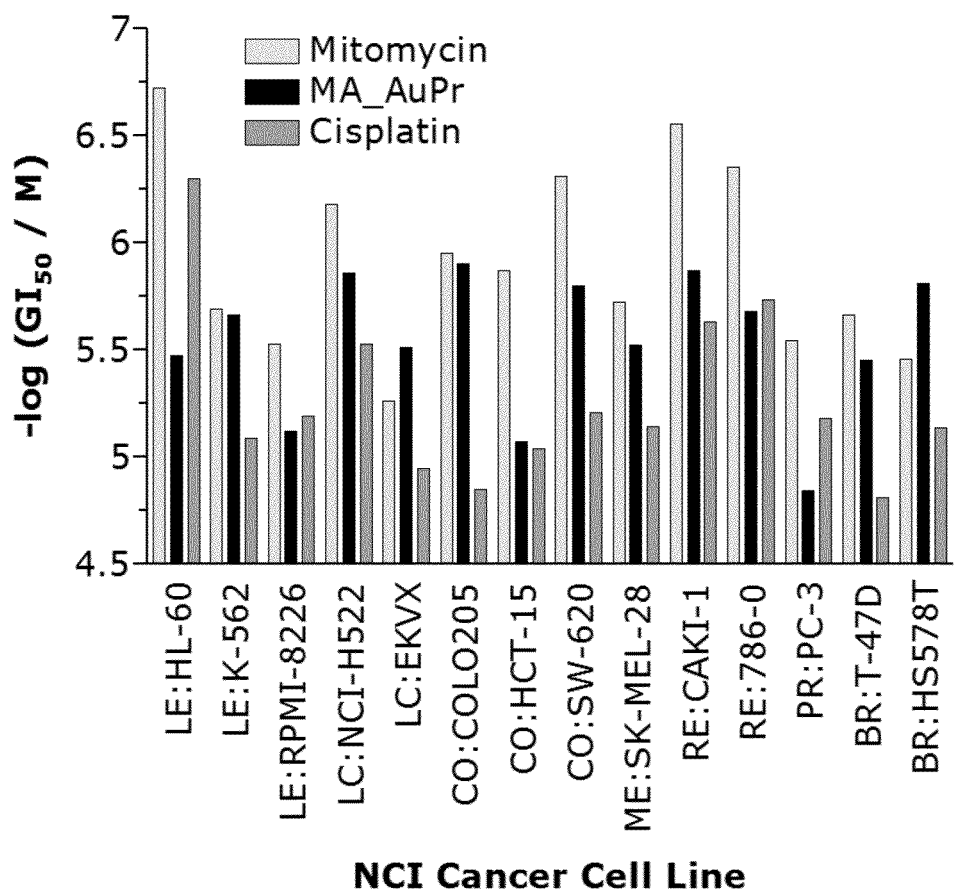
FIG. 11 is a chart of the comparison of –log(GI$_{50}$) values for MA_AuPr with commercially available anticancer drugs for selected human cancer cell lines.

FIG. 11 shows a comparison of $-\log(GI_{50})$ values for MA_AuPr (the best performing open-chelate Au(III) complex of this invention) with two comparable commercially available anticancer drugs (cisplatin and mitomycin) for selected human cancer cell lines (LE, leukemia; LC, lung cancer; CO, colo-rectal cancer; RE, renal carcinoma; PR, prostate cancer; BR, breast cancer).

Figure 12:
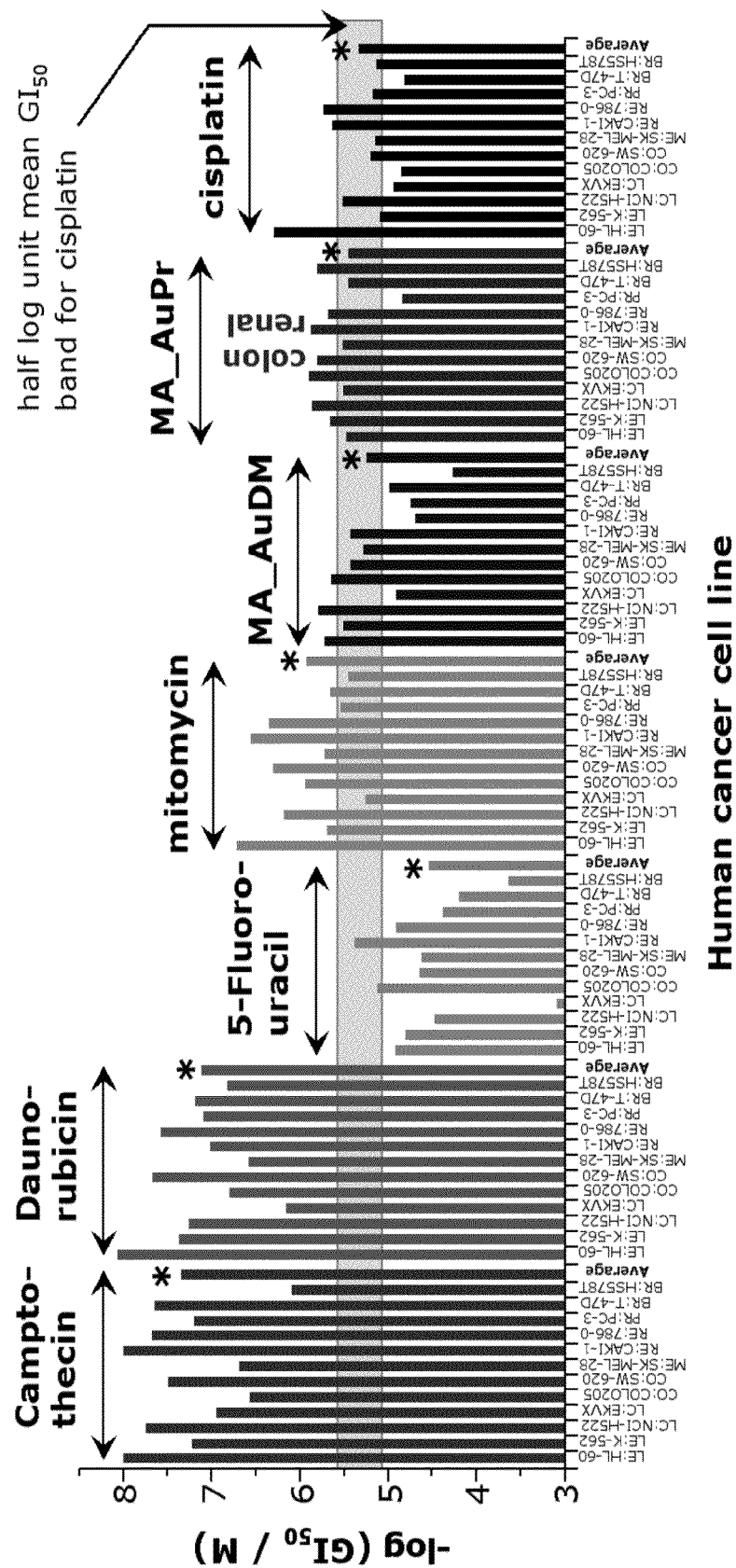
FIG. 12 is a chart of the comparison of –log(GI$_{50}$) values for MA_AuPr and MA_AuDM with commercially available anticancer drugs for selected human cancer cell lines.

FIG. 12 compares the performance (specifically as the drug concentration at which 50% growth inhibition is observed) of two open-chelate gold(III) complexes of the invention with existing commercial anti-cancer drugs for selected human cancer cell lines. The average $-\log(GI_{50})$ values for all of the drugs over the cancer cell lines plotted are marked with an asterisk.

FIGS. 11 and 12 show the following. Firstly MA_AuPr is more active than MA_AuDM and cisplatin for the cancer cell lines plotted. MA_AuPr also performs similarly to mitomycin for several important cancers (renal carcinoma and colon cancer) and is better than cisplatin, on average, for the selected leukemia, colon, and renal cancer cell lines. MA_AuPr is also significantly more active than 5-fluorouracil and carmustine [mean $-\log(GI_{50})$=4.20, data not shown]. MA_AuPr is less active than the topoisomerase poisons camptothecin (topo I) and daunorubicin (topo II). This is consistent with the fact that the compound is a dual-mode catalytic inhibitor and poison of topoisomerase II and has a slightly different mode of action with the enzyme. It is noteworthy that potent topoisomerase poisons are acutely toxic with some severe side-effects. This is often problematic because the damage caused to healthy cell DNA by these drugs is mutagenic and has been shown to result in the initiation of secondary cancer post-treatment (i.e. genotoxicity). The current strategy employed by oncologists is therefore to administer a potent topoisomerase poison (camptothecin or daunorubicin) and an independent topoisomerase catalytic inhibitor to diminish the damage caused by these highly cytotoxic topoisomerase poisons. There is thus an advantage to having a less cytotoxic dual-mode drug like MA_AuPr with a better balance between general and specific cytotoxicity. Indeed, this is why cisplatin, oxaliplatin, and carboplatin are widely used in first-line chemotherapy to treat the majority of human cancers (all are notably less genotoxic and less cytotoxic than duanorubicin).

The in vitro cytotoxicities of the two non-macrocyclic gold (III) chelates of the invention shown in FIGS. 11 and 12 are clearly comparable to or better than that of cisplatin. Inherent specificity for renal, colon, and some leukemia cell lines has also been observed. It is an advantage of the invention that gold is cheaper than platinum and this would confer a competitive edge to the compounds of the invention.

Mechanism of Action

From the data presented above, it is clear that the compound MA_AuPr is an effective cytotoxic agent that is suitably active against multiple human cancer cell lines. Identification of the cellular target of the compound and elucidation of its biological mechanism of action are critical to the optimization of lead compounds into successful chemotherapeutic agents. There are three key parameters which define the cytotoxic activity of a compound against a given cancer cell line, namely its $GI_{50}$, $IC_{50}$, and $LC_{50}$ values (see FIG. 8). One drug tested over 60 cancer cell lines affords 180 experimental data that may be compared with the same parameters for all other compounds similarly tested against the NCI's panel of 60 human cancer cell lines. Only hierarchical cluster analysis offers a tractable statistical approach to establish functional relationships between drugs with a large data set. There are various ways in which to effect hierarchical cluster analysis of a large data set. Irrespective of the method chosen, one expects to delineate which drugs exhibit similar activity profiles over the full 60 cell line panel. Compounds most similar in behavior will converge in the statistical analysis to form a tight group or cluster. If a test agent has an unknown mechanism of action and is found to cluster or fall within a group of compounds whose mechanism of action has been previously and independently determined, then one can conclude, with reasonably high certainty, that the test agent is active against the same cellular target as the majority of the compounds within a particular cluster.

Figure 13:
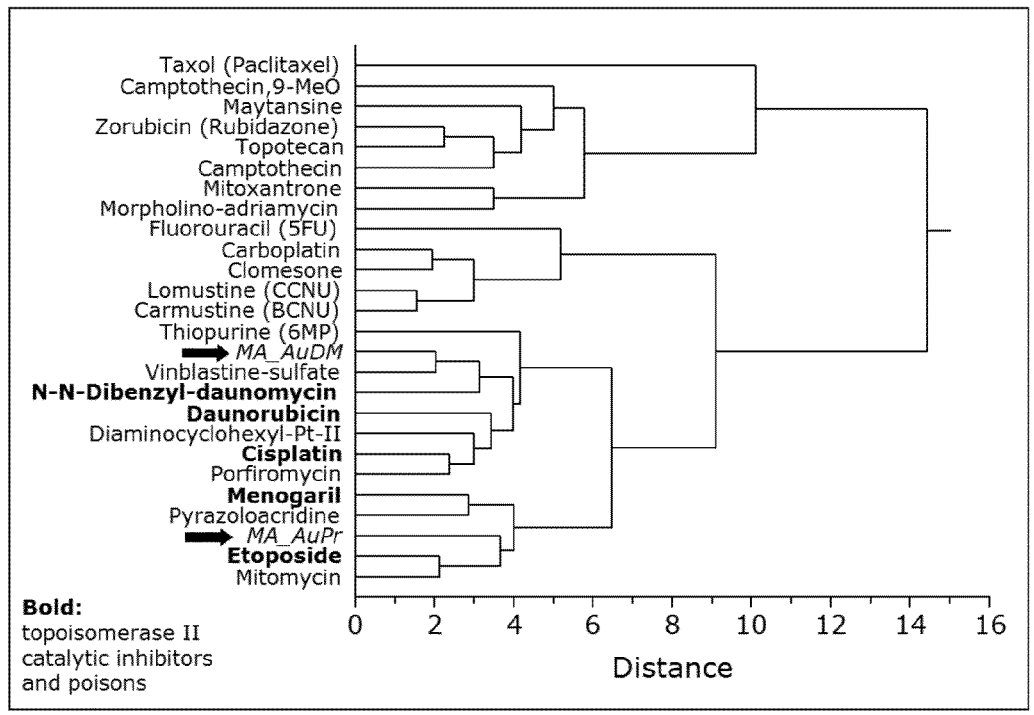
FIG. 13 is a chart of the comparison of the activity profiles of commercial drugs with a known mechanism of action and the two Au(III) chelates MA_AuPr and MA_AuDM. (Group average method, Minkowski distance.)

FIG. 13 shows a dendrogram obtained via hierarchical cluster analysis of the $GI_{50}$, $IC_{50}$, and $LC_{50}$ values for a range of commercial anti-cancer drugs with known mechanisms of action. The Au(III) compounds of the invention were included in the analysis and are highlighted in red. It is clear from the clusters shown that the activity of MA_AuPr correlates best with that of etoposide, one of the most widely used topoisomerase II poisons. The compound also appears on a branch with a direct, though distant, link to the drugs daunorubicin and cisplatin. Daunorubicin is a potent topoisomerase II poison, while cisplatin has been shown to be an effective catalytic inhibitor[25] of topoisomerase II (in addition to its role as a DNA cross-linker and guanine-N7 "alkylating" agent).

Topoisomerase II is an essential nuclear enzyme found in all living cells. Topoisomerase II participates in various DNA metabolic processes, such as transcription, DNA replication, chromosome condensation, and de-condensation, and is essential at the time of chromosome segregation after cell division.[26] This enzyme transiently creates a protein-concealed double-strand break in one DNA molecule through which a second double-stranded DNA molecule can be transported prior to religation of the DNA.[26] There are two classes of compounds that act against topoisomerase II—poisons and catalytic inhibitors. The former compounds stabilize the ternary drug-enzyme-DNA cleavage complex and favor an increase in the number of DNA double strand breaks; these are highly damaging to cancer cells and lead to apoptosis (programmed cell death).[27] The latter compounds (catalytic inhibitors) are either competitive inhibitors (block DNA binding), non-specific inhibitors (react with topoisomerase II sulfhydryl groups, e.g., cisplatin,[25] thereby altering the proper function of the enzyme), or inhibitors that block the ATPase domain of the enzyme (effectively curtailing the ATP-dependent DNA strand passage step in the cycle). Highly successful, though highly toxic, commercial anticancer compounds active against topoisomerase II include the drugs etoposide, teniposide, doxorubicin, daunorubicin, and idarubicin.[26] There are, however, difficulties associated with the use of these drugs in chemotherapy due to their high general toxicity. The cardiac toxicity of the compounds is generally high and catalytic inhibitors of topoisomerase II (such as dexrazoxane, ICRF-187) are administered along with a topoisomerase poison to temper the toxicity of the poison,[28] or to prevent tissue damage (necrosis) when extravasation of a topoisomerase poison occurs during chemotherapy.[29] There is also good evidence to suggest that topoisomerase poisons are themselves carcinogenic, such that the development of post-treatment (secondary) cancer occurs in some patients.[30]

Figure 14:
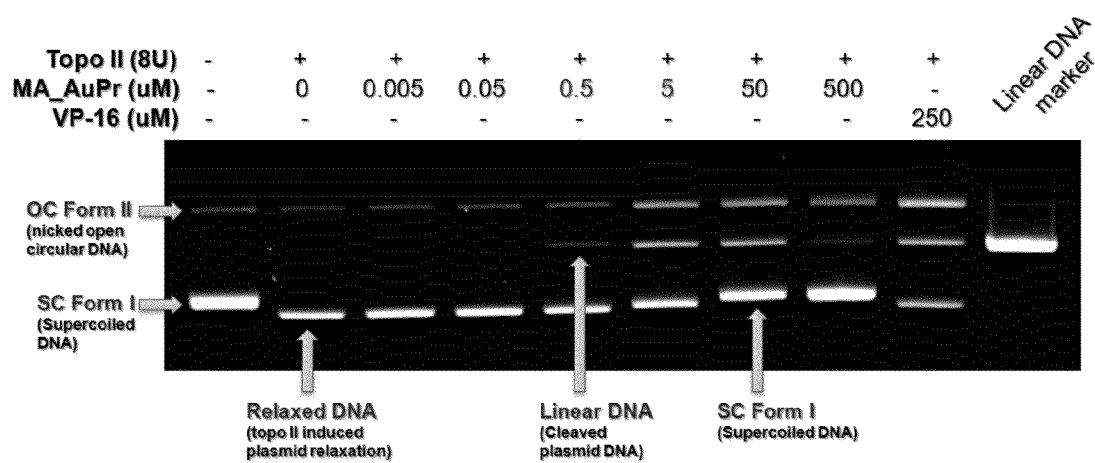
FIG. 14 is a photograph of an EB gel showing the poisoning at low concentrations (0.5 μM) and catalytic inhibition at higher concentrations (50 μM) of topoisomerase II activity on supercoiled plasmid DNA substrate by MA_AuPr.

The compound MA_AuPr clearly targets topoisomerase II if the statistical analysis of the NCI data for a range of drugs shown in FIG. 13 is correct. MA_AuPr was therefore assayed for its action against topoisomerase II in vitro using TopoGEN's standard protocol over a wide range of test agent concentrations (0.005 to 500 µM) in order to obtain direct experimental proof for the apparent cellular target of the compound to ensure that a fundamental understanding of the mechanism of action of this new class of Au(III) compounds exists. These experiments were performed by the company TopoGEN and at the University of Central Florida. The DNA cleavage experiments were performed in vitro using purified topoisomerase I and II enzymes and supercoiled plasmid DNA as the substrate. The controls that were used in the experiment were linear marker DNA as well as reactions without the gold(III) complex and high concentrations of VP16. The compound VP16 (etoposide) is a commercially available DNA intercalator chemotherapeutic agent, widely used in the treatment of lung and testicular cancers as well as lymphomas. The choice of VP16 as a control is based on the fact that it is a poor topoisomerase II inhibitor, but is a powerful topoisomerase II poison which arrests the enzyme's cycle at the ternary drug-enzyme-DNA cleavage complex stage, leading to observation of linear DNA fragments upon SDS denaturation of the enzyme (i.e., work-up). Comparison of the VP16 results with the results of MA_AuPr would therefore give a good indication of whether the gold(III) chelate is an inhibitor or a poison. The results of the ethidium bromide (EB) gel analysis are shown in FIG. 14.

Lane 1 of the gel (FIG. 14) is the control experiment with only supercoiled plasmid DNA present. The control contains no topoisomerase II and so the DNA supercoiled structure cannot be relaxed, as the topoisomerase II enzyme would usually do. The gel shows that the complex MA_AuPr begins to effectively poison topoisomerase II at a concentration of 0.5 µM (lane 5 of the gel), as evidenced by the formation, trapping, and detection of linear DNA cleavage products at this concentration of the test agent. At a higher concentration of the test agent (50 µM), both supercoiled plasmid DNA and linear cleavage products are observed. This shows that MA_AuPr exhibits dual action at this concentration in that it functions both as a topoisomerase II poison (forming linear DNA) and as a topoisomerase II catalytic inhibitor (preventing relaxation of the supercoiled plasmid DNA substrate). At very high concentrations (>500 µM), MA_AuPr behaves exclusively as a catalytic inhibitor of the enzyme.

The formation of a low concentration of linear DNA (lane 5 of the gel) demonstrates that the compound MA_AuPr has the ability to interrupt the second step of the cleavage/ligation cycle, in particular preventing religation of the double-stranded DNA. This conclusion is based on the fact that the cleavage/ligation cycle leads to formation of trapped intermediates, which resolve as linear DNA in the gels. In summation, the test compound MA_AuPr is therefore both a poison and a catalytic topoisomerase II inhibitor.

This result is particularly interesting since, in the treatment of brain cancers in mice, combinations of topoisomerase II inhibitors and poisons are often used because the efficacy of the combined treatment is greater than the sum of the parts and a catalytic inhibitor modulates the acute toxicity of the poison. Therefore, a drug that demonstrates both inhibition and poisoning of the enzyme is potentially a novel and useful chemotherapeutic agent.[25]

Figure 15:
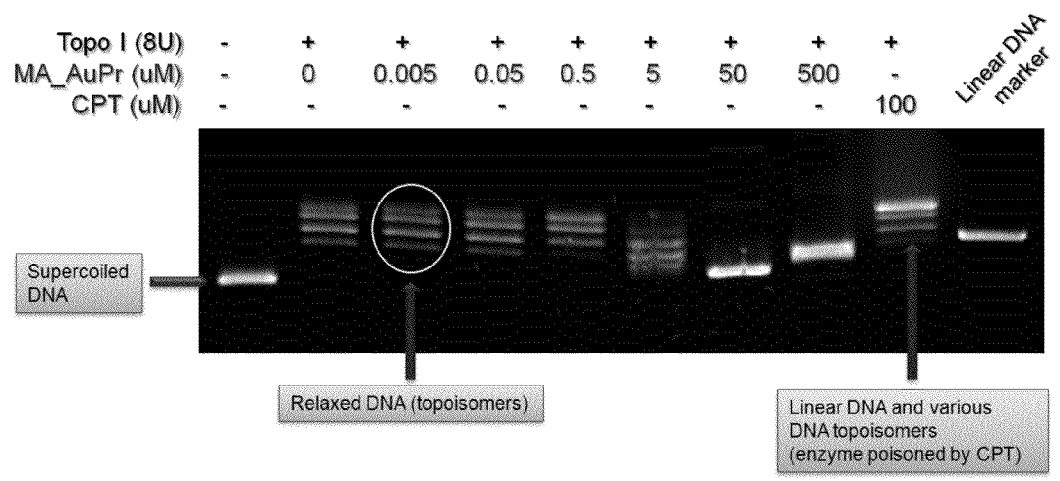
FIG. 15 is a photograph of an EB gel showing the inactivity of MA_AuPr against topoisomerase I compared to the chemotherapeutic agent CPT (camptothecin), which is specifically a topoisomerase I poison.

MA_AuPr was also tested to determine if the compound was a topoisomerase I poison or inhibitor since the compound appears to be a topoisomerase II-specific agent and not a DNA intercalator with multiple enzyme targets. The results are shown in the EB gel in FIG. 15. The gel electrophoresis experiment shows that the gold(III) chelate is not a topoisomerase I poison. This conclusion is based on comparison of the migration of the DNA with various concentrations of the gold(III) chelate with the lane containing CPT (camptothecin, a topoisomerase-I specific poison) and linear DNA as a reference or marker. This result shows that the gold(III) chelate specifically poisons topoisomerase II and not topoisomerase I.

Figure 16:
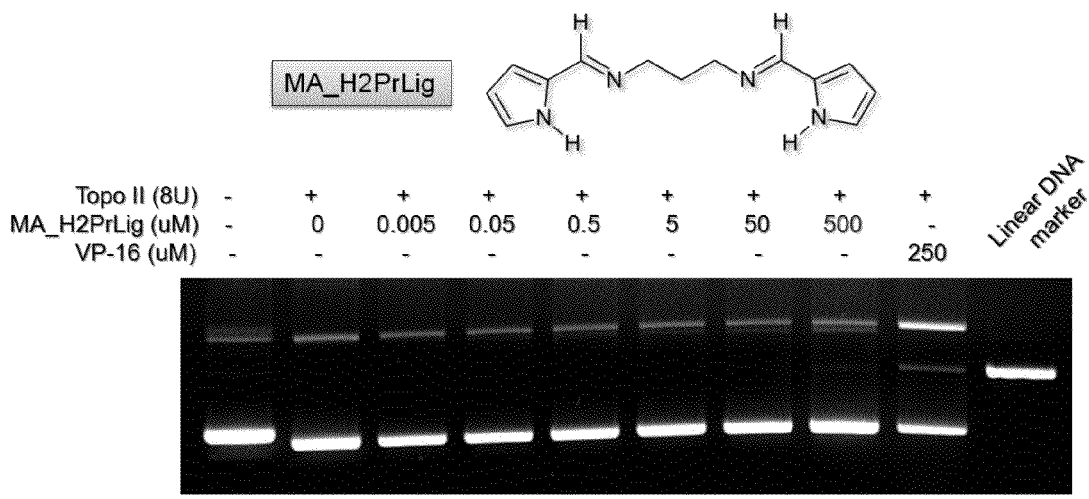
FIG. 16 is a photograph of an EB gel showing the inactivity of MA_H2PrLig (the metal-free ligand) against topoisomerase II compared to the chemotherapeutic agent VP-16 (etoposide), which is specifically a topoisomerase II poison. There is evidence of weak DNA-cleavage induction in the presence of topoisomerase II from the free ligand at 500 μM concentration.

The role of gold(III) in the efficacy of the compound was determined by modifying the structure of MA_AuPr by replacing the Au(II) cation with Pd(II) to afford MA_PdPr (the isoelectronic square planar coordination complex of known structure and geometry[31]) and carrying out the DNA relaxation assay with topoisomerase II as before. The metal-free ligand (MA_H2PrLig) was tested under identical conditions to confirm that the mechanism of action is related to the intact structure of the metal chelate. The results are shown in FIGS. 16 and 17.

The data confirm firstly that the free ligand is not a good topoisomerase II poison. Secondly, The efficacy of the Au(III) chelate is 100 times higher than that of the isoelectronic Pd(II) chelate. This result is expected and is consistent with the electrophilic character of the Au(III) ion, which is known to favor electrostatic interactions with aromatic groups or anions perpendicular to the square planar coordination group (i.e., the vacant axial interaction sites at the metal center). Compound 1a is also positively charged, whereas the Pd(II) chelate is neutral and thus likely to exhibit diminished electrostatic attraction for the phosphate backbone of double-stranded DNA.

The topo II inhibition assay for the Au(III) macrocycle KA_AumacroPr is shown above in FIG. 18. In contrast to MA_AuPr, this complex functions as a pure catalytic inhibitor of topo II since no trapped linear DNA cleavage products are evident that would signal behavior of the complex as a topo II poison. The enzyme inhibition is characterized by an $IC_{50}$ of 4.8 µM, which is in excellent agreement with the cell cytotoxicity $IC_{50}$ value measured for this compound against HeLa cells (FIG. 9).

As indicated by the DNA unwinding assay in FIG. 19, the test agent KA_AumacroPr interferes with the normal operation of human topoisomerase I. Specifically, abnormal relaxation products are generated from supercoiled plasmid DNA. This is consistent with strong intercalative binding of KA_AumacroPr to the plasmid DNA probably before and after the action of topoisomerase I, and consequently inhibition of its normal turnover cycle. Collectively the data in FIGS. 18 and 19 show that the macrocyclic Au(III) complex $1.1Y^1b$ functions as a catalytic inhibitor of human topoisomerase I. Similar data were obtained for complexes $1.1Y^1a$ and $1.5Y^1a$.

For a drug to act as a topoisomerase II poison, two molecular recognition events must occur. Firstly, the drug must bind to DNA via intercalation between base pairs and secondly, the drug must interact with topoisomerase II in such a way that religation of the DNA after formation the topoisomerase II-DNA covalent complex (the catalytic intermediate) is impossible. The enzyme is poisoned at this point and the cycle irreversibly disrupted by the drug. FIG. 20 shows titration data for the titration of complex 1.1a with calf-thymus DNA (ctDNA).

The hypochroism of the absorption band of the complex at 383 nm was monitored as a function of added ctDNA. The data were fitted to equation (1)$^{32}$ to determine the affinity constant by non-linear regression:

$$(\epsilon_a - \epsilon_f)/(\epsilon_b - \epsilon_f) = (b - (b^2 - 2K_a^2 Ct[DNA]/s)^{1/2})/2K_a Ct \quad (1a)$$

$$b = 1 + K_a Ct + K_a[DNA]/2s \quad (1b)$$

where [DNA] is the concentration of DNA base pairs, $\epsilon_a$ is the extinction coefficient ($A_{abs}/[M]$) observed for the 383-nm MLCT absorption band of MA_AuPr at a given DNA concentration, $\epsilon_f$ and $\epsilon_b$ are the extinction coefficient for the free Au(III) complex and the extinction coefficient for the Au(III) complex in the fully bound form, respectively. $K_a$ is the equilibrium binding constant in $M^{-1}$, Ct is the total Au(III) complex concentration, and s is the binding site size.

From FIG. 20, it is clear that compound 1.1a binds to ctDNA with a high affinity constant. Moreover, since the MLCT (metal-to-ligand-charge-transfer) band of the complex at 383 nm decreased upon DNA binding (hypochroism), the mode of interaction is likely to be intercalation, as occurs with Ru(II) complexes with known DNA-intercalating bidentate ligands.

Scheme 19
Summary of selected calf thymus DNA binding constants for open- and macrocyclic Au(III) chelates.

| Complex | $K_a$ (calf thymus DNA)/$M^{-1}$ | Cytotoxicity[#] |
|---|---|---|
| 1.1a (MA_AuPr) | $2.05(2) \times 10^5$ | active |
| 1.1b (MA_AuDM) | $1.63(3) \times 10^5$ | active |
| 1.1c (MA_AuOH) | $1.43(3) \times 10^5$ | in vitro only |
| 1.1d (MA_AuOEt) | $1.01(4) \times 10^6$ | active |
| 1.1e (MA_AuCl) | $3.91(7) \times 10^5$ | active |
| $1.1Y^1a$ (KA_AumacroPr) | $2.8(2) \times 10^6$ | active |
| $1.1Y^1b$ (KA_AumacroDM) | $1.49(8) \times 10^6$ | active |
| $1.5Y^1a$ (KA_AumacroBu) | $1.20(9) \times 10^6$ | active |

Conditions:

MA series of complexes in pH 7.0 phosphate buffer at 37° C.

KA series of complexes in pH 7.0 15% DMSO-TRIS buffer at 25° C.

[#]Active: mean $IC_{50}$ value in low µM range in the NCI-60 cytotoxicity screen or in an independent cytotoxicity screen.

In vitro: the compound is a proven too II poison in vitro (cell-free enzyme assay).

Scheme 19 summarizes the DNA affinity constants for the compounds. The affinity constants are high ($10^5$ to $10^6$ $M^{-1}$) and the data clearly show, in unison with FIG. 20, that both the non-macrocyclic and macrocyclic Au(III) complexes are DNA intercalators. Consequently, the compounds are capable of disrupting the topoisomerase I or II DNA religation step and/or its ability to bind DNA (competitive inhibition). In short, the compounds of this invention act as poisons and/or inhibitors of the human topoisomerase I and/or II enzyme in vitro.

Toxicology

Key to the design of compounds for cancer chemotherapy is an early assessment of their toxicology profiles. Compounds have to be well-tolerated in live subjects, easily metabolized or excreted, well-transported across cell membranes, and have favorable plasma stability to be worthy of detailed pre-clinical animal model studies.

Scheme 20
Summary of key in vitro ADME-Tox (absorption, distribution, metabolism, toxicology) data for MA_AuPr.

| Test | Key Indicator | Comment |
|---|---|---|
| Microsomal clearance | $t_{1/2}$ < 10 min | Highly metabolized; low liver toxicity expected |
| Plasma half-life | $t_{1/2}$ < 20 min | Highly metabolized |
| Plasma protein binding | No binding - drug undetected | Unstable in plasma; requires encapsulation for transport |
| Genotoxicity | Negative | Non-mutagenic |
| Cytotoxicity (Hep-G2) | Strong positive | Good cytotoxicity expected (consistent with NCI-60 screens of drug) |
| Caco-2 | Not an efflux transporter substrate | Favorable intestinal uptake expected |

The most promising non-macrocyclic Au(III) complex, MA_AuPr, was selected for in vitro ADME-Tox profiling to gauge the potential of the compound for pre-clinical animal toxicology testing and further development towards phase I human trials. The data are summarized in Scheme 20, which reveals a number of positive attributes for the compound. First, the compound is not genotoxic (i.e. mutagenic). This means the invented compounds have a clear advantage over topo II poisons such as daunorubicin and its derivatives which are known to be genotoxic but are in clinical use. Second, the compound is rapidly metabolized by liver cytochrome P450 enzymes and hepatotoxicity is not anticipated. Third, the Hep-G2 cytotoxicity assay confirmed the expected good cytotoxicity displayed in the NCI-60 screen of the compound. Fourth, the Caco-2 transport data clearly demonstrate that the test agent is not an efflux transporter substrate and has the ability to freely pass across a monolayer of Caco-2 cells (a model for the human small intestine wall or mucosa) without much preference for direction. The Caco-2 data are especially important as many drugs fail due to poor membrane transport/absorption. The transport rates for MA_AuPr are summarized in Scheme 21.

Scheme 21
Summary of Caco-2 transport for MA_AuPr, ranitidine (a substrate for efflux transporter proteins), and warfarin (a non-substrate for efflux transporters).

| Cpd. | Test Conc. (uM) | Assay Duration (h) | mean A→B $P_{app}$ ($10^{-6}$ cm s$^{-1}$) | mean B→A $P_{app}$ ($10^{-6}$ cm s$^{-1}$) | Efflux Ratio |
|---|---|---|---|---|---|
| Ranitidine | 10 | 2 | 0.7 | 2.3 | 3.3 |
| Warfarin | 10 | 2 | 37.0 | 8.0 | 0.2 |
| MA_AuPr | 10 | 2 | 4.0 | 9.0 | 1.2 |

The only possibly concerning ADME-Tox result shown in Scheme 20 is that the test compound did not bind to plasma protein and was, in fact, not identified in a structurally intact form by LC-MS in the protein-free fraction (i.e. the molecular ion peak for MA_AuPr was not detected in the mass spectrum). The $t_{1/2}$ of MA_AuPr in plasma was <20 min. This suggests fast conversion of the compound to another species in the presence of plasma constituents and could suggest covalent interaction with proteins or metal ion aquation/hydrolysis possibly by enzyme action. Experiments in our lab with compound 1.2a (MA_AuEt, in which W=W$^2$, R and R$^1$-R$^4$ are H, Y=2H, and Z and Z$^1$=C) have shown that water may displace a pyrrole ring from the Au(III) ion to form a Au(III)-OH species and protonated pyrrole ring. MA_AuPr did not show hydrolysis in phosphate buffered aqueous solutions presumably because the 6-membered chelate ring leads to a more stable chelate for Au(III). This is why binding to DNA of the intact chelate occurs (FIGS. 14 and 20). However, it is noteworthy that hydrolysis of a Au(III)-N$_{pyrrole}$ bond is a reaction that may be catalyzed by enzymes in plasma and could account for the plasma instability of MA_AuPr. By way of comparison, the plasma half-life of cisplatin measures 0.88 h or ca. 53 min, while that of its mono(aqua) complex is 0.26 h (16 min).[33] The plasma stability of MA_AuPr is thus very similar to that of the mono(aqua) cisplatin derivative (cisplatin is one of the most successful anticancer drugs in the history of cancer chemotherapy).

The Applicant is of the firm opinion that encapsulation of the non-macrocyclic Au(III) compounds belonging to Formula (I) in γ-cyclodextrin or other water-soluble encapsulating agents such as curcubit-[8]-uril will permit increased plasma half-lives for these compounds. Encapsulation for metallo-drug transport and stabilization is well-established in the literature,[34] and has been shown to enhance the redox and plasma stability of cisplatin analogues.[34] It should be noted that enhanced plasma stability for the macrocyclic Au(III) complexes belonging to Formula (I) is anticipated because hydrolysis of the Au—N$_{pyrrole}$ bonds in the macrocycle is quite unlikely. Experiments investigating this concept further are currently underway in our laboratory.

Scheme 22
Summary of cell health parameters for HepG2 human hepatocellular carcinoma cells exposed to serial dilutions of MA_AuPr and chlorpromazine (control).

| Cell Health Parameter | MA_AuPr MEC (μM) | MA_AuPr AC$_{50}$ (μM) | MA_AuPr MEC | MA_AuPr AC$_{50}$ | Chlorpromazine MEC (μM) | Chlorpromazine AC$_{50}$ (μM) | Chlorpromazine MEC | Chlorpromazine AC$_{50}$ |
|---|---|---|---|---|---|---|---|---|
| Cell Loss | <0.23 | 7.4 | | x | 100 | 7.8 | | |
| Nuclear Area | 6.2 | 17 | | | >11 | 100 | | |
| DNA structure | >19 | N/A | | | 11 | 196 | | |
| Membrane permeability | 2.1 | 16 | x | | 11 | 30 | | |
| Mitochondrial mass | 2.1 | 41 | x | | 3.7 | 5.4 | x | x |
| Mitochondrial membrane potential | 6.2 | >500 | x | | 3.7 | 50 | x | |
| Cytochrome C release | 19 | 33 | | | 11 | 16 | | |

MEC: Minimum effective concentration that significantly crosses vehicle control threshold.
N/D: Not determined due to lowest concentration tested is the returned MEC.
AC$_{50}$: The concentration at which 50% maximum effect is observed for each cell health parameter.
N/A: The response was not significantly above control to determine an AC$_{50}$ value.
First Signal (x): The cell health feature which responds at the lowest observed dose.

The data for MA_AuPr in Scheme 22 are consistent with a cytotoxic compound capable of inducing apoptosis (programmed cell death) and, indeed, a compound that performs better than the control drug. The lowest MEC response data indicate that the compound MA_AuPr has resulted in an increase in membrane permeability (indicating general cell death), an increase in mitochondrial mass (indicating an adaptive response to cellular energy demands), and an increase in mitochondrial potential (implying adaption to cellular energy requirements). Other cell health parameters which respond are a loss of total cells per well (indicating toxicity due to necrosis, apoptosis or a reduction in cellular proliferation), an increase in nuclear area (indicating necrosis or G2 cell cycle arrest), an increase in cytochrome c release (implying activation of a signalling cascade leading to apoptosis). The latter is particularly relevant as we may rule out cell death by necrosis in the case of MA_AuPr. The mechanism of action of the compound thus leads to cell cycle arrest in the G2 phase and the induction of apoptosis (highly desirable for an anticancer drug). The lowest $AC_{50}$ response indicates that the compound MA_AuPr has resulted in a loss of total cells per well (indicating toxicity due to necrosis, apoptosis or a reduction in cellular proliferation). Since the compound induces cytochrome c release, cytotoxicity involves apoptosis.

The plasma stability and cytotoxicity of a test drug may be examined more extensively in an animal model (in vivo).

FIG. 21 shows a graph of 3LL tumor growth (measured by caliper methods at the University of Strasbourg, France) in black mice over a 20-day period at the indicated doses. (The 3LL cell line is a solid Lewis lung carcinoma cell line of the mouse.) The compound MA_AuPr, despite its modest plasma stability in vitro (Scheme 20) and poor performance against human lung carcinoma cell lines in the NCI-60 screen (FIG. 5), clearly slows down the growth rate of 3LL tumors in black mice by about 33% relative to the control after 20 days. In comparison to cisplatin, which reduces the growth rate of 3LL tumors by 76% in 20 days and is a highly effective drug against lung carcinoma cell lines, MA_AuPr has about 43% of the in vivo performance of cisplatin for this particular cancer cell line. We note that the gold(III) chelates of this invention out-perform cisplatin for several colorectal carcinoma cell lines, renal carcinomas, and breast cancer cell lines (FIGS. 10 and 11), so that the data presented in FIG. 21 may be taken as a lower limit of the compound's in vivo cytotoxicity. The value of the experimental data shown in FIG. 21 clearly lies in the fact that it demonstrates that MA_AuPr has sufficient plasma stability in live animals to exert a positive cytotoxic effect leading to reduced tumor growth rates, even for a class of tumors for which the compound is expected to perform poorly.

The results are most encouraging and suggest that xenografts of human tumor cell lines susceptible to MA_AuPr (e.g. colon carcinoma cell lines) in mouse model subjects are likely to prove illuminating and worth the cost. Furthermore, the Applicant anticipates that the most cytotoxic macrocyclic Au(III) complexes, e.g., compound $1.5Y^1a$, may have good plasma half-lives due to their enhanced redox stability and resistance to hydrolysis such that better time-dependent tumor growth profiles are quite likely for the macrocyclic members of Formula (I) of the invention.

FIG. 22 shows a set of survival data for five groups of four mice receiving from 1 to 30 μmol/kg doses of MA_AuPr. A single dose of the compound was administered by injection over the first week followed by two injections per week per mouse for a total period of 50 days. All of the mice remained healthy and showed no abnormal weight changes over the timeframe of the experiment (mouse mass data not shown, but available as a time dependent plot). The results demonstrate that MA_AuPr has an acute toxicity >30 μmol/kg/week and a chronic toxicity >60 μmol/kg/week. This is fully consistent with the ADME-Tox data (Scheme 20) which showed that the compound is highly metabolized by liver microsomes.

In conclusion, the ADME-Tox and in vivo toxicology data for MA_AuPr are complementary and collectively indicate that:

MA_AuPr is a cytotoxic metal complex (a topoisomerase II poison and inhibitor) with a mean in vitro $IC_{50}$ value in the low μM range.

MA_AuPr is not genotoxic.

MA_AuPr induces apoptosis in cancer cells such as HepG2.

MA_AuPr is not a substrate for the efflux transporters in a Caco-2 cell monolayer and exhibits *facile* bidirectional transfer across this mucosal membrane mimic.

MA_AuPr is readily metabolized by liver microsomes.

MA_AuPr has a short plasma half life ($t_{1/2}$<20 min) which is similar to the mono(aqua) derivative of cisplatin, $[PtCl(NH_3)_2(OH_2)]^+$.

MA_AuPr is cytotoxic in a live animal setting (mice) and demonstrates the ability to reduce tumor growth rates for mouse lung carcinoma cells (despite having poor cytotoxicity in general for lung tumor cell lines).

MA_AuPr is non-toxic to healthy black mice exhibiting acute and chronic toxicity values >30 μmol/kg/week and >60 μmol/kg/week, respectively.

EXAMPLE 2

Synthesis of MA_AuPr and Other Open-Chelate Derivatives

Scheme 25

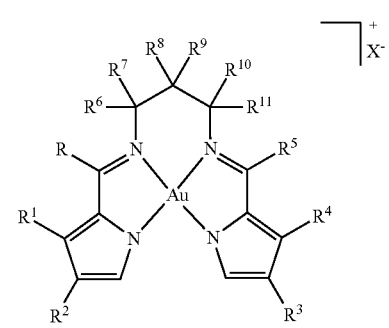

1.1

1.1a R = H, $R^n$ = H
1.1b R——$R^7$ = H, $R^8$ = $R^9$ = $CH_3$, $R^{10}$——$R^{11}$ = H
1.1c R——$R^8$ = H, $R^9$ = OH, $R^{10}$——$R^{11}$ = H
1.1d R——$R^8$ = H, $R^9$ = $OCH_2CH_3$, $R^{10}$——$R^{11}$ = H
1.1e R——$R^8$ = H, $R^9$ = Cl, $R^{10}$——$R^{11}$ = H

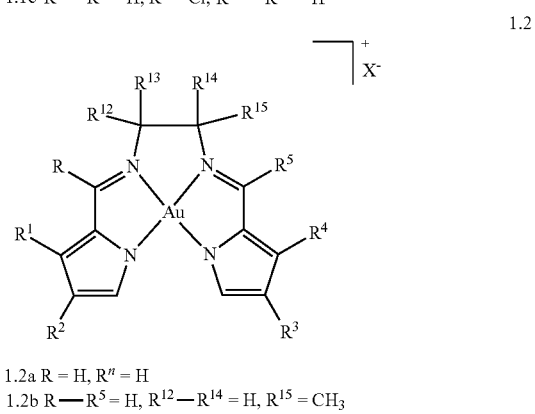

1.2

1.2a R = H, $R^n$ = H
1.2b R——$R^5$ = H, $R^{12}$——$R^{14}$ = H, $R^{15}$ = $CH_3$

-continued

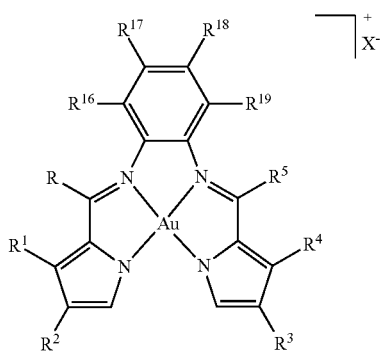

1.3a R = H, R″ = H
1.3b R—R⁵ = H, R¹⁶ = H, R¹⁷ = CH₃, R¹⁸–R¹⁹ = H

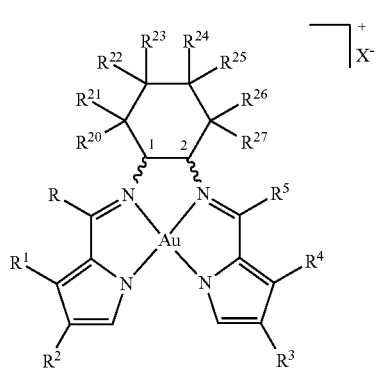

1.4a R = H, R″ = H, racemic
1.4b R = H, R″ = H, 1S, 2S enantiomer
1.4c R = H, R″ = H, 1R, 2R enantiomer Open chelate Au(III) compound library synthesized and fully characterized using the methodology outlined for MA_AuPr. The anion X⁻ is typically chloride or $PF_6^-$.

Generic Description of Materials for the Synthesis of Bis(Pyrrolide-Imine) and Bis(Imidazolato-Imine) Gold(III) Chelates The general synthetic procedure for the synthesis of all non-macrocyclic ligands in this invention involves the condensation of two equivalents of 1H-pyrrole-2-carbaldehyde or 5-methyl-1H-imidazole-4-carbaldehyde with an appropriate 1,2- or 1,3-diaminoalkane linker unit, which forms a diiminoalkane bridge in the Schiff base condensation product. The bis(imine) compounds produced from such condensation reactions are then purified and reacted with a gold(III) salt in a suitable solvent system to form a relatively planar chelate of gold(III).

The synthetic procedure for macrocyclic gold(III) chelates required, in most cases, the initial reaction of 2,3-bis(5'-formylpyrrol-2'-yl)quinoxaline with a gold(III) salt to form an intermediate metal chelate in which the formyl oxygen atoms and deprotonated pyrrole nitrogen atoms function in unison as a tetradentate chelating ligand and most likely form a gold(III) chelate with a $AuN_2O_2$ coordination group. This intermediate is not isolated but condensed in situ with a 1,3- or 1,4-diaminoalkane linker unit, which, through the formation of a pair Au-bound imine groups and concomitant loss of two molar equivalents of water, cyclizes the ligand to form the product Au(III) macrocycle as a monocationic complex.

Commercially available diaminoalkanes were purchased from Aldrich and used without further purification. Commercially unavailable 1,3-diamines such as 2-ethoxy-1,3-diaminopropane and 2-chloro-1,3-diaminopropane were synthesized by t-boc protection of the two amino groups of 1,3-diamino-2-hydroxypropane followed by reaction of the hydroxy group and subsequent deprotection of the amino groups. Thus, although the compounds 2-ethoxy-1,3-diaminopropane and 2-chloro-1,3-diaminopropane are themselves not novel, with several synthetic approaches available from the literature,[35,36] the method we have employed to make them (as dihydrochloride salts) from t-boc-protected 1,3-diamino-2-hydroxypropane and to use them in subsequent condensation reactions to form diimines is novel.

Synthetic details for making key synthons for subsequent preparation of the chelating ligands described herein are given below.

Synthesis of 2,2,12,12-t-methyl-3,11-dioxo-4,10-dioxa-5,9-diazatridecan-7-ol (N,N'-di-t-boc-2-hydroxy-1,3-diaminopropane)

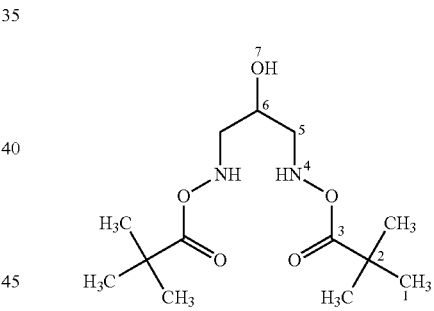

Sodium hydrogencarbonate (8.3 g, 99 mmol) was dissolved in 1:1 acetonitrile:water mixture (190 mL) and the solution cooled to 4° C. in an ice bath. 1,3-diamino-2-hydroxypropane (2.5 g, 27 mmol) and di-tert-butyldicarbonate (12.8 g, 59 mmol) were dissolved in the same solvent system (65 mL). This mixture was then added to the chilled sodium hydrogencarbonate solution and stirred on ice for two hours. The reaction was then heated to room temperature and stirred overnight. The acetonitrile was removed by rotary evaporation and the protected amine extracted into dichloromethane (3×75 mL portions). The organic portions were combined, dried over sodium carbonate, and evaporated to dryness by rotary evaporation.[37] The resulting oil was re-crystallised from diethylether/hexane,[38] giving colourless crystals (7.2 g, 91% yield). The compound was characterised by $^1H$ and $^{13}C$ NMR and FT-IR spectroscopy. IR (cm⁻¹): 3316 m br ν(OH and NH), 2971 m and 2930 m ν(CH₃ and CH), 1681 s ν(C=O). $^1H$ NMR (400 MHz, CDCl₃, 298 K) [δ, ppm]: 1.45 (s, 18H, H-1), 3.20 (m, 4H, H-5), 3.75 (m, 2H, H-6 and H-7), 5.20 (s br, 2H, H-4). $^{13}$C NMR (100 MHz, CDCl$_3$, 298K) [δ, ppm]: 28.55 (C-1), 43.72 (C-2), 71.07 (C-5), 79.87 (C-6), 157.24 (C-3).

Synthesis of 2-ethoxy-1,3-diaminopropane dihydrochloride

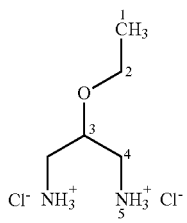

N,N'-di-t-boc-2-hydroxy-1,3-diaminopropane (2.0 g, 6.9 mmol) and [Bu$_4$N][HSO$_4$] (0.44 g, 1.3 mmol) were dissolved in toluene (7.5 mL). To this 50% aqueous NaOH (7.5 mL) and ethyl iodide (1.67 mL, 20.7 mmol) were added. The resulting biphasic solution was heated to 100° C. for 18 hours. The solution was diluted with water and the alkylated compound extracted into ethylacetate (75 mL); this solution was washed with brine and then water and dried over anhydrous Na$_2$CO$_3$. The solvent was then removed by rotary evaporation and the resulting oil purified by column chromatography on silica gel using 1:4 ethylacetate:hexane as the eluent.[39] The solvent in the column fractions containing the alkylated product was removed by rotary evaporation and the resulting oil was dissolved in methanolic HCl (1.25 M, 30 mL) and stirred overnight. 2-ethoxy-1,3-diaminopropane dihydrochloride precipitated as an oil from the methanol solution with the addition of diethylether. The oil was separated from the methanol by centrifugation and dried over P$_2$O$_5$ to give the hydrochloride salt as a white powder (0.70 g, 53% yield). The powder was characterised by $^1$H NMR. $^1$H NMR (400 MHz, D$_2$O, 298 K) [δ, ppm]: 1.24 (t, 3H, H-1), 3.14 (dd, 2H, $^3J_1$=7.13 Hz, $^3J_2$=14.2 Hz, H-4), 3.35 (dd, 2H, $^3J_1$=4.3 Hz, $^3J_2$=13.0 Hz, H-4), 3.69 (q, 2H, H-2), 4.03 (m, 1H, H-3).

Synthesis of 2-chloro-1,3-diaminopropane dihydrochloride

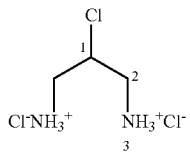

N,N'-di-t-boc-2-hydroxy-1,3-diaminopropane (1.0 g, 3.5 mmol) and triphenylphosphine (1.5 g, 5.72 mmol) were dissolved in chloroform (15 mL) and carbon tetrachloride (35 mL). This solution was refluxed for 5 hours, before the solvents were removed under reduced pressure by rotary evaporation. The resulting oil was dissolved in diethylether to precipitate the OPPh$_3$ and the resulting solution centrifuged to remove the insoluble OPPh$_3$. The diethyl ether was removed by rotary evaporation and the resulting oil dissolved in methanolic HCl (1.25 M, 30 mL) and stirred overnight. The 2-chloro-1,3-diaminopropane dihydrochloride was precipitated as a white powder by the addition of dichloromethane. The powder was stored over P$_2$O$_5$ (0.304 g, 49% yield). The complex was characterised by $^1$H and $^{13}$C NMR spectroscopy. $^1$H NMR (400 MHz, D$_2$O, 298 K) [δ, ppm]: 3.34 (dd, 2H, $^3J_1$=3.8 Hz, $^3J_2$=14.7 Hz, H-2), 3.57 (dd, 2H, $^3J_1$=3.3 Hz, $^3J_2$=13.9 Hz, H-2), 4.58 (m, 1H, H-1). $^{13}$C NMR (100 MHz, D$_2$O, 298K) [δ, ppm]: 42.95 (C-2), 54.94 (C-1).

General Synthesis of Simple Bis(Pyrrole-Imine) and Bis(Imidazole-Imine) Ligands

1H-Pyrrole-2-carbaldehyde (30 mmol) or 5-methyl-1H-imidazole-4-carbaldehyde (30 mmol) and a 1,2- or 1,3-diaminoalkane derivative (15 mmol) were refluxed in ethanol (30 mL) for two hours. During refluxing the reaction mixture changed from colourless to a clear, bright orange. Solvent was then removed by rotary evaporation, leaving a viscous orange-coloured oil. The oil was then dissolved in dichloromethane prior to adding hexane to the solution, which was left to re-crystallise overnight. This typically yields the crystalline bis(Schiff base) product in around 70-90% yield. The crystalline product can be shown to be clean by thin layer chromatography or $^1$H NMR spectroscopy. Single crystals suitable for X-ray crystallography may also be obtained from the re-crystallisation process. The procedure and full characterization for N,N'-bis[(1E)-1H-pyrrol-2-ylmethylene]propane-1,3-diamine have, for example, been reported elsewhere.[14]

General Synthesis of New Bis(Pyrrole-Imine) Ligands from 1,3-Diaminopropane Dihydrochloride Salts The general strategy when condensing dihydrochloride salts of the diamine linker group with two molar equivalents of 1H-pyrrole-2-carbaldehyde was to carry out the reaction under solvent-free conditions to avoid incompatible solubility of the two reagents and to obviate the use of organic bases for deprotonation of the diamine reagent's ammonium groups. A typical solid-state reaction is described below.

Excess sodium carbonate (ca. 4 mmol) and a relevant 2-substituted 1,3-diaminopropane dihydrochloride derivative (ca. 2 mmol) were ground in an agate pestle and mortar for 1 minute. To the resulting white paste, 1H-pyrrole-2-carbaldehyde (ca. 4 mmol) was added and the mixture ground together for a further 10 min. Water was then added to the paste, followed by acetone, to dissolve the ligand. The solvent solution was collected and the acetone allowed to evaporate, yielding the ligand as a pale yellow powder. The powder was purified by re-crystallisation from 1:30:50 ethanol:THF:hexane. Typical isolated yields were of the order of 60-70%. The product ligands were analysed by $^1$H NMR, $^{13}$C NMR, UV/visible and IR spectroscopy. In some cases, crystals suitable for a structure determination by X-ray diffraction were obtained during the re-crystallisation step. Synthetic methods and characterization data for several novel ligands prepared in this way are described below.

Synthesis of 2-chloro-N-[(1E)-1H-pyrrol-2-ylmethylene]N'-[(1Z)-1H-pyrrol-2-ylmethylene]-propane-1,3-diamine

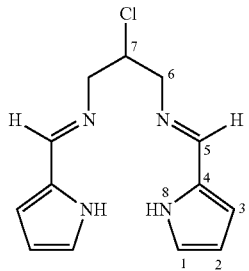

Sodium carbonate (0.448 g, 4.24 mmol) and 2-chloro-1,3-diaminopropane dihydrochloride (0.350 g, 1.93 mmol) were ground in an agate pestle and mortar for 1 minute. To the resulting white paste, 1H-pyrrole-2-carbaldehyde (0.365 g, 3.93 mmol) was added and the mixture ground together for a further 10 min. Water was then added to the paste, followed by acetone, to dissolve the ligand. The solvent solution was collected and the acetone allowed to evaporate, yielding the ligand as a pale yellow powder. The powder was re-crystallised from 1:30:50 ethanol:THF:hexane (0.290 g, 62% yield). The novel ligand was further characterized by $^1$H NMR, $^{13}$C NMR, UV/visible and IR spectroscopy. UV/vis (ethanol) [$\lambda_{max}$, nm; $\epsilon_1$ mol$^{-1}$ dm$^3$ cm$^{-1}$]: 292; 3.81×10$^4$. IR (cm$^{-1}$): 3183 w δ(NH, pyrrole), 2942 m br ν(CH, imine), 2838 m ν(CH, H—CCl), 1643 s br ν(C=N), 743 (C—Cl stretch). $^1$H NMR (400 MHz, DMSO-d$_6$, 298 K) [δ, ppm]: 3.74 (dd, $^3J_1$, =7.2 Hz, $^3J_2$=5.3 Hz, 2H, H-6), 4.01 (dd, $^3J_1$=7.88 Hz, $^3J_2$=5.3 Hz, 2H, H-6), 4.45 (m, 1H, H-7) 6.13 (t, 2H, H-2), 6.50 (dd, $^3J_1$, =3.7 Hz, $^3J_2$=1.3 Hz, 2H, H-3), 6.90 (s br, 2H, H-1), 8.11 (s, 2H, H-5), 11.37 (s br, 2H, CD$_3$OD exchangeable, H-8). $^{13}$C NMR (100 MHz, DMSO-d$_6$, 298 K) [δ, ppm]: 63.57 (C-6), 64.88 (C-7), 109.47 (C-2), 114.53 (C-3), 122.96 (C-1), 129.98 (C-4), 154.43 (C-5).

Synthesis of 2-ethoxy-N,N-bis[(1E)-1H-pyrrol-2-ylmethylene]propane-1,3-diamine

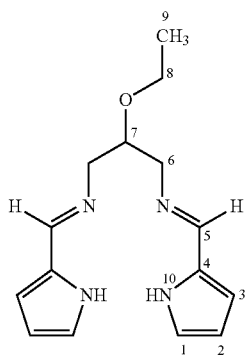 [SMILES: CCOC(C/N=C/c1ccc[nH]1)C/N=C/c1ccc[nH]1]

Sodium carbonate (0.366 g, 3.45 mmol) and 2-ethoxy-1,3-diaminopropane dihydrochloride (0.300 g, 1.57 mmol) were ground together in an agate pestle and mortar for 5 min. To the resulting white paste, 1H-pyrrole-2-carbaldehyde (0.299 g, 3.14 mmol) was added and the mixture ground for a further 10 min. The crude ligand was dissolved in dichloromethane (40 mL) and washed with water (3×25 mL) portions. The organic layer was dried over anhydrous sodium carbonate. To the dichloromethane solution, aliquots of ethanol (1 mL) and hexane (50 mL) were added to re-crystallise the ligand. Crystals suitable for singe crystal X-ray diffraction were obtained from the re-crystallisation (0.280 g, 65% yield). The novel ligand was further characterized by $^1$H NMR, $^{13}$C NMR, UV/visible and IR spectroscopy and X-ray diffraction. UV/vis (ethanol) [$\lambda_{max}$, nm; $\epsilon$, mol$^{-1}$ dm$^3$ cm$^{-1}$]: 290; 3.48×10$^4$. IR (cm$^{-1}$): 3158 w δ(NH, pyrrole), 2975 m br ν(CH, imine), 2901 m ν(CH, H—COCH$_2$), 2838 m ν(CH, CH$_3$) 1631 s br ν(C=N), 734 (C—O stretch). $^1$H NMR (400 MHz, CDCl$_3$, 298 K) [δ, ppm]: 1.08 (t, 3H, H-9), 3.49-3.65 (m, 4H, H-6), 3.65-3.80 (m, 3H, H-8), 6.21 (t, 2H, H-2), 6.46 (dd, $^3J_1$=3.7 Hz, $^3J_2$=1.3 Hz, 2H, pyrrole H-3), 6.86 (s br, 2H, H-1), 8.03 (s, 2H, H-5), 9.53 (s, 2H, CD$_3$OD exchangeable, H-10). $^{13}$C NMR (100 MHz, CDCl$_3$, 298 K) [δ, ppm]: 15.62 (C-9), 62.64 (C-6), 65.82 (C-8), 79.31 (C-7), 109.66 (C-2), 114.34 (C-3), 122.02 (C-1), 130.26 (C-4), 153.68 (C5).

Synthesis of tert-butylammonium tetrachloroaurate(III)

There are several methods in the literature for making [Bu$_4$N][AuCl$_4$]. We have developed a modified version of a typical method which involves precipitation of [Bu$_4$N][AuCl$_4$] after the addition of [Bu$_4$N]Cl to a solution of H[AuCl$_4$].[40] More specifically, we found it necessary to add a solvent-extraction step to the preparative method to obtain an acid-free product suitable for subsequent metallation reactions of the potentially hydrolysable Schiff base ligands described in this invention.

Hydrogen tetrachloroaurate(III) (0.406 g, 0.98 mmol) was dissolved in deionised water (15 mL). To this solution tert-butylammonium hydrogen sulphate (340 mg, 1.01 mmol) was added, forming a lipophillic gold(III) salt, which immediately precipitated from the aqueous solution as a bright yellow powder:

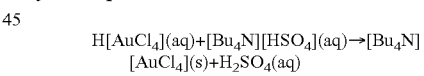

The [Bu$_4$N][AuCl$_4$] was then extracted from the sulphuric acid into chloroform. The organic solution was dried over magnesium sulphate before the chloroform was removed by rotary evaporation, leaving a bright yellow, crystalline solid (0.570 g, 97.2% yield). The crystalline solid was dried under vacuum and stored under nitrogen.

General Metallation of Simple Bis(Pyrrole-Imine) and Bis (Imidazole-Imine) Ligands In a typical reaction carried out under an inert atmosphere, [Bu$_4$N][AuCl$_4$] (100 mg, 0.172 mmol) was added to a dry 100 mL round-bottom flask and dissolved in 20 mL of dry dichloromethane. Five molar equivalents of free base ligand (0.860 mmol) were dissolved in 15 mL of dry ethanol. The ethanolic solution was then heated and the gold(III) solution was added via cannula transfer to the hot ethanol solution and the mixture stirred under nitrogen. The solution rapidly turned a deep red colour and the product precipitated from the solution as a pale yellow powder after approximately 45 minutes. The precipitate was collected by centrifugation. This crude material was re-crystallized by slow liquid diffusion of a methanol solution of the complex into diethylether. The re-crystallized product may be isolated in 60-70% yield and analysed by X-ray crystallography as well as LCMS, NMR, IR and UV/visible spectroscopy.

Specific Synthetic Procedure for Compound 1.1a

The synthetic scheme (Scheme 26 below) and structures of the reagents and products are shown below for MA_AuPr. The method is general for all of the non-macrocyclic bis (pyrrolide-imine) structures listed in Formula (I).

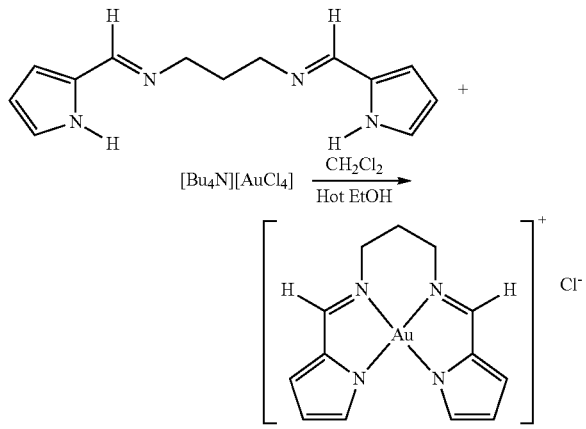

Scheme 26

The following reaction was carried out under inert atmosphere conditions. To a dry 100 mL round-bottomed flask, [Bu$_4$N][AuCl$_4$] (100 mg, 0.172 mmol) was added and dissolved in 20 mL dry dichloromethane. Five molar equivalents of free base ligand (196 mg, 0.860 mmol) was dissolved in 15 mL of dry ethanol (the ligand was synthesized as previously described[14]). The ethanolic solution was then heated and the gold(III) solution was added via cannula transfer to the hot ethanol solution and the mixture stirred under nitrogen. The solution rapidly turned a deep red color and the product precipitated from the solution as a pale yellow powder after approximately 45 minutes. The precipitate was now air stable and was collected by centrifugation. This crude material was re-crystallized by slow liquid diffusion of a methanol solution into diethylether. The re-crystallized product (52.8 mg, 0.148 mmol, 67% yield) was shown to be MA_AuPr by X-ray crystallography as well as NMR, IR and UV/visible spectroscopy.

It was found that use of a smaller excess of ligand resulted in the desired chelate. The counterion of this chelate was not, however, the desired chloride ion but rather a linear gold(I) chloride, [AuCl$_2$]$^-$. The presence of this undesirable anion was confirmed by X-ray crystallography. The developed method with the addition of the gold(III) solution to the excess ligand, dissolved in hot ethanol consistently produced the desired chelate, with the desired anion.

The salt [Bu$_4$N][AuCl$_4$] was found to be more satisfactory than the more conventional [Na][AuCl$_4$] as the source of gold(III) ions for two reasons. First, the use of [Na][AuCl$_4$] resulted in the formation of [AuCl$_2$]$^-$ anions, regardless of the concentration of the ligand solution. Second, the salt [Bu$_4$N][AuCl$_4$] is soluble in non-polar solvents, unlike [Na][AuCl$_4$] which is only soluble in polar solvents. This therefore means that the chelation reaction can be carried out in non-polar solvents. This is ideal since the starting materials are soluble in non-polar solvents, while the gold(III) chelate is not. The gold(III) chelate therefore precipitates out of solution relatively pure. This synthetic method was therefore found to require no additional purification steps, the final crystallization was sufficient to generate a high purity material.

Characterization Data for Compound 1.1a 2,2'-{propane-1,3-diylbis[nitrilo(E)methylylidene]}bis(pyrrol-1-ido)gold(III) chloride M/Z$^+$=423.0885 M$^+$ (calc.=423.0884). UV/vis (methanol) [λmax, nm; ϵ, mol$^{-1}$ dm$^3$ cm$^{-1}$]: 288; 1.47×10$^4$, 382; 1.05×10$^4$. IR (KBr pellet, cm$^{-1}$): 3090 m br v(CH, imine), 3010 m v(CH, CH$_2$CH$_2$CH$_2$), 2930 m v(CH, CH$_2$—N=CH), 1590 s br v(C=N). $^1$H NMR (400 MHz, CD$_3$OD, 298 K) [δ, ppm]: 2.28 (q, 2H, CH$_2$CH$_2$CH$_2$), 3.78 (t, 4H, CH$_2$—N=CH), 6.49 (dd, $^3$J$_1$=2.5 Hz, $^3$J$_2$=2.5 Hz, 2H, pyrrole β-H), 7.05 (d, 2H, pyrrole γ-H), 7.58 (d br, 2H, pyrrole α-H), 8.22 (s, 2H, imine). $^{13}$C NMR (100 MHz, CD$_3$OD, 298 K) [δ, ppm]: 32.53 (CH$_2$CH$_2$CH$_2$), 52.95 (CH=NCH$_2$), 113.96 (pyrrole β-C), 124.39 (pyrrole γ-C), 138.32 (pyrrole C NH—C—C=N), 139.25 (pyrrole α-C), 164.55 (imine C).

Characterization Data for Compound 1.1b 2,2'{(2,2-dimethylpropane-1,3-diyl)bis[nitrilo(E)methyl-ylidene]}bis(pyrrol-1-ido)gold(III) chloride M/Z$^+$=451.1196 M$^+$ (calc.=451.1197). UV/vis (ethanol) [λ$_{max}$, nm; ϵ, mol$^{-1}$ dm$^3$ cm$^{-1}$]: 290; 1.48×10$^4$, 381; 1.11×10$^4$. IR (KBr pellet, cm$^{-1}$): 3176 w δ(NH, pyrrole), 3125 m br v(CH, imine), 2970 m v(CH, terminal CH$_3$), 2854 m v(CH$_2$, alkyl), 1631 s br v(C=N). $^1$H NMR (400 MHz, CD$_3$OD, 298 K) [δ, ppm]: 0.98 (s, 6H, terminal CH$_3$), 3.43 (s, 4H, alkyl CH$_2$), 6.26 (dd, $^3$J$_1$=3.7 Hz, $^3$J$_2$=1.3 Hz, 2H, pyrrole β-H), 6.45 (t, 2H, pyrrole γ-H), 6.91 (s br, 2H, pyrrole α-H), 8.02 (s, 2H, imine). $^{13}$C NMR (100 MHz, CD$_3$OD, 298 K) [δ, ppm]: 22.18 (CH$_3$), 39.03 (C(CH$_3$)$_2$), 61.70 (CH=NCH$_2$), 112.84.69 (pyrrole β-C), 123.33 (pyrrole γ-C), 137.57 (Pyrrole C NH—C—C=N), 137.95 (pyrrole α-C) 163.98 (imine C).

Characterization Data for Compound 1.1c 2,2{(2-hydroxypropane-1,3-diyl)bis[nitrilo(E)methyl-ylidene]}bis(pyrrol-1-ido)gold(III) hexafluorophosphate(V)

M/Z$^+$=439.0834 M$^+$ (calc.=439.0833). UV/vis (methanol) [λ$_{max}$, nm; ϵ, mol$^{-1}$ dM$^3$ cm$^{-1}$]: 282; 1.57×10$^4$, 379; 1.15×10$^4$. IR (KBr pellet, cm$^{-1}$): 3431 m br δ(OH), 3110 m br v(CH, imine), 2985 m v(CH, H—COH), 2946 m v(CH, CH$_2$—N=CH), 1592 s br v(C=N), 1104 w (C—O stretch). $^1$H NMR (400 MHz, D$_2$O, 298 K) [δ, ppm]: 3.35 (s, 1H, HOCH), 3.77 (s, 2H, CH$_2$—N=CH, 6.36 (dd, $^3$J$_1$=2.1 Hz, $^3$J$_2$=1.8 Hz pyrrole β-H), 6.89 (s br, 2H, pyrrole γ-H) 7.24 (s, 2H, pyrrole α-H), 8.02 (s, 2H, imine). $^{13}$C NMR (100 MHz, D$_2$O, 298 K) [δ, ppm]: 54.95 (CH$_2$CHOHCH$_2$), 69.02 (CH$_2$CHOHCH$_2$), 100.03 (pyrrole β-C), 113.07 (pyrrole γ-C), 124.00 (pyrrole C NH—C—C=N), 137.08 (pyrrole α-C), 164.62 (imine C).

Characterization Data for Compound 1.1d 2,2{(2-ethoxypropane-1,3-diyl)bis[nitrilo(E)methy-lylidene]}bis(pyrrol-1-ido)gold(III) hexafluorophosphate(V)

M/Z$^+$=467.1148 M$^+$ (calc.=467.1146). UV/vis (acetonitrile) [λ$_{max}$, nm; ϵ, mol$^{-1}$ dm$^3$ cm$^{-1}$]: 288; 1.43×10$^4$, 379.5; 1.10×10$^4$. IR (cm$^{-1}$): 2909 m br v(CH, imine), 2880 m v(CH, H—COC), 1581 s br v(C=N), 1045 s v(C—O) 834 w v(PF$_6$).

¹H NMR (400 MHz, CD₃CN, 298 K) [δ, ppm]: 1.16 (t, 3H, CH₃), 3.61 (q, 2H, OCH₂CH₃), 3.80 (d, 2H, CH₂—N═CH), 3.95 (dd, ³J₁,=9.6 Hz, ³J₂=5.8 Hz, 2H, CH₂—N═CH), 4.31 (t, 1H, OCH), 6.53 (dd, ³J₁,=2.1 Hz, ³J₂=1.8 Hz pyrrole β-H), 7.10 (s br, 2H, pyrrole γ-H) 7.54 (s, 2H, pyrrole α-H), 8.12 (s, 2H, imine). ¹³C NMR (100 MHz, CD₃CN, 298 K) [δ, ppm]: 14.50 (CH₃), 29.99 (OCH₂CH₃) 53.28 and 64.20 (CH₂CHClCH₂), 75.49 (CH), 112.85 (pyrrole γ-C), 123.59 (pyrrole C NH—C—C═N), 137.65 (pyrrole α-C), 164.36 (imine C).

Characterization Data for Compound 1.1e 2,2'-{(2-chloropropane-1,3-diyl)bis[nitrilo(E)methylylidene]}bis(pyrrol-1-ido)gold(III) hexafluorophosphate(V)

M/Z⁺=457.0497 M⁺ (calc.=457.0494). UV/vis (acetonitrile) [λ$_{max}$, nm; ε, mol⁻¹ dm³ cm⁻¹]: 289; 1.54×10⁴, 381.5; 1.22×10⁴. IR (cm⁻¹): 3141 m br ν(CH, imine), 3046 m ν(CH, H—CCl), 1581 s br ν(C═N), 822 w ν(PF₆), 741 s ν(C—Cl). ¹H NMR (400 MHz, CD₃CN, 298 K) [δ, ppm]: 3.96 (dd, ³J₁=10.00 Hz, ³J₂=4.85 Hz, 2H, CH₂—N═CH), 4.15 (d, 2H, CH₂—N═CH), 5.00 (t, 1H, ClCH), 6.56 (dd, ³J₁=2.1 Hz, ³J₂=1.8 Hz pyrrole β-H), 7.16 (s br, 2H, pyrrole γ-H) 7.57 (s, 2H, pyrrole α-H), 8.11 (s, 2H, imine). ¹³C NMR (100 MHz, CD₃CN, 298 K) [δ, ppm]: 55.86 (CH₂CHClCH₂), 58.00 (CH₂CHClCH₂), 100.03 (pyrrole β-C), 113.28 (pyrrole γ-C), 124.52 (pyrrole C NH—C—C═N), 137.59 (pyrrole α-C), 164.65 (imine C).

Characterization Data for Compound 1.2a 2,2'-{ethane-1,2-diylbis[nitrilo(E)methylylidene]}bis(pyrrol-1-ido)gold(III) hexafluorophosphate(V)

M/Z⁺=409.0728 M⁺ (calc.=409.0729). UV/vis (acetonitrile) [λ$_{max}$, nm; ε, mol⁻¹ dm³ cm⁻¹]: 292; 1.45×10⁴, 385; 1.07×10⁴. IR (KBr pellet, cm⁻¹): 3127 m br ν(CH, imine), 3053 m ν(CH, CH₂CH₂), 2866 m ν(CH, CH₂—N═CH), 1575 s br ν(C═N). ¹H NMR (400 MHz, CD₃OD, 298 K) [δ, ppm]: 4.40 (s, 4H, CH₂—N═CH), 6.50 (dd, ³J₁=2.14 Hz, ³J₂=1.3 Hz, 2H, pyrrole β-H), 7.08 (s, 2H, pyrrole α-H), 7.47 (t, 2H, pyrrole γ-H), 7.86 (s, 2H, imine). ¹³C NMR (100 MHz, CD₃CN, 298 K) [δ, ppm]: 62.49 (CH₂CH₂), 112.89 (pyrrole β-C), 125.67 (pyrrole γ-C), 137.99 (pyrrole α-C), 138.84 (Pyrrole C NH—C—C═N), 161.44 (imine C). ³¹P NMR (162 MHz, CD₃CN, 298 K) [δ, ppm]: −144.62 (PF₆). ¹⁹F NMR (376 MHz, CD₃CN, 298 K) [δ, ppm]: −73.82, —71.95 (PF₆).

Characterization Data for Compound 1.2b 2,2'-{(2S)-propane-1,2-diylbis[nitrilo(E)methylylidene]}bis(pyrrol-1-ido)gold(III) hexafluorophosphate(V)

M/Z⁺=423.0883 M⁺ (calc.=423.0884). UV/vis (acetonitrile) [λ$_{max}$, nm; ε, mol⁻¹ dm³ cm⁻¹]: 293.5; 1.42×10⁴, 385; 1.08×10⁴. IR (KBr pellet, cm⁻¹): 3125 w br ν(CH, imine), 1552 s br ν(C═N), 830 s (PF₆). ¹H NMR (400 MHz, CD₃OD, 298 K) [δ, ppm]: 1.62 (d, 3H, CH₃) 4.21 (dd, ³J₁=7.88 Hz, ³J₂=6.5 Hz, 1H, CH₂), 4.48 (dd, ³J₁=8.58 Hz, ³J₂=5.81 Hz, 1H, CH₂) 4.85 (m, 1H, CHCH₃), 6.50 (dd, ³J₁=2.14 Hz, ³J₂=1.3 Hz, 2H, pyrrole β-H), 7.08 (s, 2H, pyrrole α-H), 7.47 (t, 2H, pyrrole γ-H), 7.84 (s, 1H, imine), 7.88 (s, 1H, imine). ¹³C NMR (100 MHz, CD₃CN, 298 K) [δ, ppm]: 16.18 (CH₃), 68.07 (CH₂), 113.03 (pyrrole β-C), 125.58 (pyrrole γ-C), 140.00 (pyrrole α-C), 143.11 (Pyrrole C NH—C—C═N), 159.68 (imine C), 161.36 (imine C). ³¹P NMR (162 MHz, CD₃CN, 298 K) [δ, ppm]: −144.27 (PF₆). ¹⁹F NMR (376 MHz, CD₃CN, 298 K) [δ, ppm]: −73.87, −71.99 (PF₆).

Characterization Data for Compound 1.3b 2,2'-{(4-methyl-1,2-phenylene)bis[nitrilo(E)methylylidene]}bis(pyrrol-1-ido)gold(III) nitrate(V)

M/Z⁺=471.0887 M⁺ (calc.=471.0889). UV/vis (ethanol) [λ$_{max}$, nm; ε, mol⁻¹ dm³ cm⁻¹]: 296; 2.00×10⁴, 323; 4.03× 10⁴, 374.5; 1.58×10⁴, 457; 1.43×10⁴. IR (cm⁻¹): 3097 m br ν(CH, imine), 2983 m ν(aromatic C—H), 1553 s br ν(C═N). ¹H NMR (400 MHz, CDCl₃, 298 K) [δ, ppm]: 2.40 (s, 3H, CH₃) 6.62-8.0 (m, 9H, aromatic C—H), 8.84 (s, 2H, imine). ¹³C NMR (100 MHz, CDCl₃, 298 K) [δ, ppm]: 21.78 (CH3), 115.26 (pyrrole α-C), 118.04 (pyrrole β-C), 120.35 (CH₃CCHCN), 120.98 (CHCHCN) 124.68 (pyrrole γ-C), 127.25 (CHCHCN) 131.23 (pyrrole C NH—C—C═N), 143.76 (CH₃C), 145.4 (Ph C), 153.33 (imine C).

Characterization Data for Compound 1.4c 2,2'-{(1R,2R)-cyclohexane-1,2-diylbis[nitrilo(E)methylyliden]}bis(pyrrol-1-ido)gold(III)hexafluorophosphate(V)

M/Z⁺=463.1195 M⁺ (calc.=463.1197). UV/vis (acetonitrile) [λ$_{max}$, nm; ε, mol⁻¹ dm³ cm⁻¹]: 294; 1.54×10⁴, 380.5; 1.22×10⁴. IR (cm⁻¹): 2955 m br ν(CH, imine), 2867 m ν(CH, CH₂CH₂), 1564 s br ν(C═N), 821 s ν(PF₆). ¹H NMR (400 MHz, DMSO, 298 K) [δ, ppm]: 1.31 and 1.65 (t, 2H, CH₂CH), 1.78 and 2.61 (d, 2H, CH₂CH₂CH), 4.32 (d, 2H, CH) 6.47 (dd, ³J₁=2.14 Hz, ³J₂=1.3 Hz, 2H, pyrrole β-H), 7.07 (t, 2H, pyrrole α-H), 7.78 (s br, 2H, pyrrole γ-H), 8.37 (s, 2H, imine). ¹³C NMR (100 MHz, DMSO, 298 K) [δ, ppm]: 24.40 (CHCH₂CH₂CH₂), 29.08 (CHCH₂CH₂CH₂), 76.86 (CHCH₂CH₂CH₂), 113.02 (pyrrole α-C), 125.20 (pyrrole β-C), 140.00 (pyrrole γ-C), 143.38 (Pyrrole C NH—C—C═N), 158.92 (imine C).

Synthesis of bis(imidazolato-imine) chelates

Procedure for Compound 1.1f

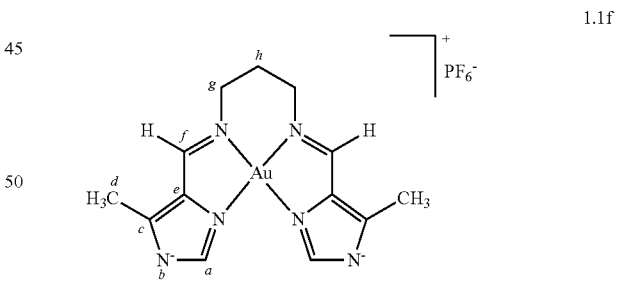

1.1f

A solution of tert-butylammonium tetrachloroaurate (100 mg, 0.172 mmol) and tert-butylammonium hexafluorophosphate(V) (400 mg, 0.103 mmol) in dichloromethane (20 ml) was added to N,N'-bis[(1E)-(5-methyl-1H-imidazol-4-yl) methylene]propane-1,3-diamine (246 mg. 0.860 mmol) in ethanol (10 mL). A yellow precipitate immediately formed. The solution was stirred at room temperature for 1 hour. The yellow precipitate of 4,4'-{propane-1,3-diylbis[nitrilo(E)methylylide]}bis(5-methylimidazol-1-ide)gold(III) hexafluorophosphate(V) (complex 1.1f) was filtered and dried (81 mg, 79%). ¹H NMR: (500 MHz, DMSO-d₆) δ 2.22 (br, 2H, h), 2.52 (s, 6H, d), 3.74 (br, 4H, g), 8.41 (s, 2H, a), 8.83 (s, 2H, t).

$^{13}$C NMR: (125 MHz, DMSO-d$_6$) δ 14.5 (d), 30.5 (h), 51.9 (g), 134.5 (c), 147.6 (a), 152.7 (e), 162.0 (f). IR (cm$^{-1}$): 1595(s), 1359(m), 1298(m), 1256(m), 1201(m), 1157(m), 971(w), 820(vs), 641 (m), 555(s), 482(m), 431 (m); MS: m/z 453.1099 (M+Na)$^+$.

Procedure for Compound 1.1q

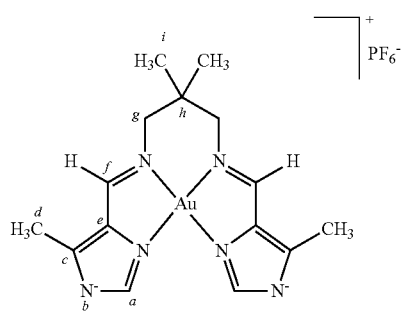
1.1g

A solution of tert-butylammonium tetrachloroaurate (100 mg, 0.172 mmol) and tert-butylhexafluorophosphate(V) (400 mg, 0.103 mmol) in dichloromethane (20 mL) was added to a 2,2-dimethyl-N,N'-bis[(1E)-(5-methyl-1H-imidazol-4-yl)methylene]propane-1,3-diamine (178 mg, 0.688 mmol) in ethanol (5 mL). This resulted in the immediate formation of a yellow precipitate. The reaction mixture was stirred for one hour at room temperature. The yellow precipitate of 4,4'-{(2,2-dimethylpropane-1,3-diyl)bis[nitrilo(E)methylylidene]}bis(5-methylimidazol-1-ide)gold(III) hexaflurophosphate (V) (complex 1.1g) was filtered and dried (89 mg, 83%). $^1$H NMR: (500 MHz, DMSO-d$_6$) δ 1.08 (s, 6H, i), 2.53 (s, 6H, d), 3.47 (s, 4H, g), 8.45 (s, 2H, a), 8.80 (s, 2H, f). $^{13}$C NMR: (125 MHz, DMSO-d$_6$) δ 14.5 (d), 30.5 (h), 51.9 (g), 134.5 (c), 147.6 (a), 152.7 (e), 162.0 (f). IR (cm$^{-1}$): 1593(s), 1381(m), 1359(m), 1277(m), 1206(m), 922(vs), 642(w), 557(vs), 438 (s). MS: m/z 481.1420 (M$^+$).

Synthesis of KA_AumacroPr and Related Au(III) Macrocycles

Scheme 26

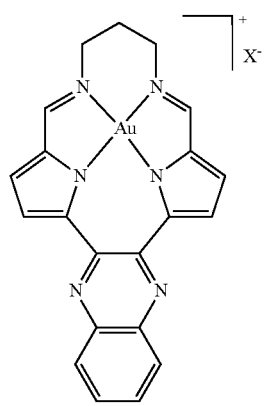
1.1Y$^1$a

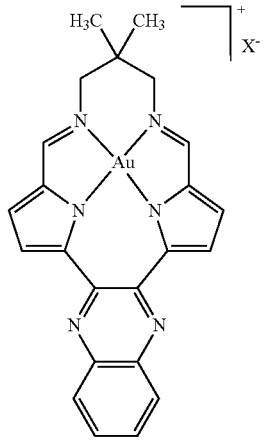
1.1Y$^1$b

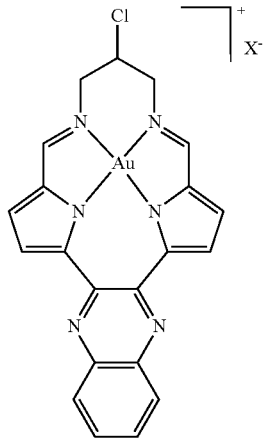
1.1Y$^1$e

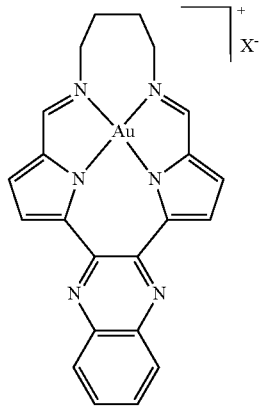
1.5Y$^1$a

Macrocyclic Au(III) compound library synthesized and characterized using the methodology outlined for KA_AumacroPr and KA_AumacroDM. The anion X$^-$ is typically PF$_6^-$, but may also be an anion such as triflate.

Only the macrocyclic ligand for 1.1Y$^1$a (i.e. that with a propyl bridge linking the two imine units) could be metallated by straightforward reaction of the macrocycle with a Au(III) salt using the method described for compound 1.1a. Complexes 1.1Y$^1$b and 1.5Y$^1$a had to be synthesized by a novel metal-templated reaction in which closure of the macrocycle through the formation of the bis(imine) links with the relevant diamine nucleophile occurs about the Au(III)-bound 2,3-bis(5'-formylpyrrol-2'-yl)quinoxaline moiety (i.e. metal-templated cyclization).

Procedure for Compound 1.1Y¹a

The free ligand was synthesized following the literature method.[41] A solution of tert-butylammonium tetrachloroaurate(III) (80 mg, 0.138 mmols) and tert-butylammonium hexafluorophosphate(V) (160 mg, 0.414 mmols) in dichloromethane (15 mL) was added dropwise to the free ligand, 12,13-dihydro-14H-6,9:17,20-diepimino[1,6]diazacyclo-heptadecino [12,13-b]quinoxaline (99 mg, 0.275 mmols) in dichloromethane (20 mL). The solution was refluxed for 16 hours. Over this time a precipitate formed which was filtered, washed with dichloromethane and dried to afford a brick red powder of {12,13-dihydro-14H-6,9:17,20-diepimino[1,6]diazacyclo-heptadecino[12,13-β]quinoxalinato}gold(III) hexafluorophosphate(V) (44 mg, 37%). Crystals suitable for single crystal X-ray diffraction were grown by vapor diffusion of diethylether into a benzonitrile solution of the product. $^1$H NMR (400 MHz, DMSO-$d_6$): δ 2.42 (br, 2H, =N—CH$_2$—CH$_2$), 3.94 (br, 4H, =N—CH$_2$—CH$_2$), 7.25 (d, $^3J_{HH}$=4.4 Hz, 2H, 3-pyrrole), 7.81 (d, $^3J_{HH}$=4.4 Hz, 2H, 4-pyrrole), 7.94-7.96 (dd, $^4J_{HH}$=3.3 Hz, $^3J_{HH}$=3.1 Hz, 2H, 6,7-quinoxaline), 8.05-8.07 (dd, $^4J_{HH}$=3.3 Hz, $^3J_{HH}$=3.1 Hz, 2H, 8,5-quinoxaline), 8.73 (s, 2H, —CH=N); $^{13}$C (100 MHz, DMSO-$d_6$): δ 33.81, 51.27, 118.76, 122.46, 128.48, 131.69, 135.53, 138.99, 139.35, 147.54, 163.05; IR (cm$^{-1}$): 2955 (br), 1649 (m), 1572 (w), 1472 (w), 1400 (m), 1294 (m), 1115 (m), 1068 (w), 832 (s), 760 (s), 664 (w), 497 (s), 424 (m); UV-vis (CH$_3$CN) $\lambda_{max}$ [nm] (ε/M$^{-1}$ cm$^{-1}$): 246 (23 346), 309 (30 077), 346 (18 001), 373 (15 237), 455 (12 041);); MS: m/z 549.1104 (M$^+$).

Procedure for Compound 1.1Y¹b

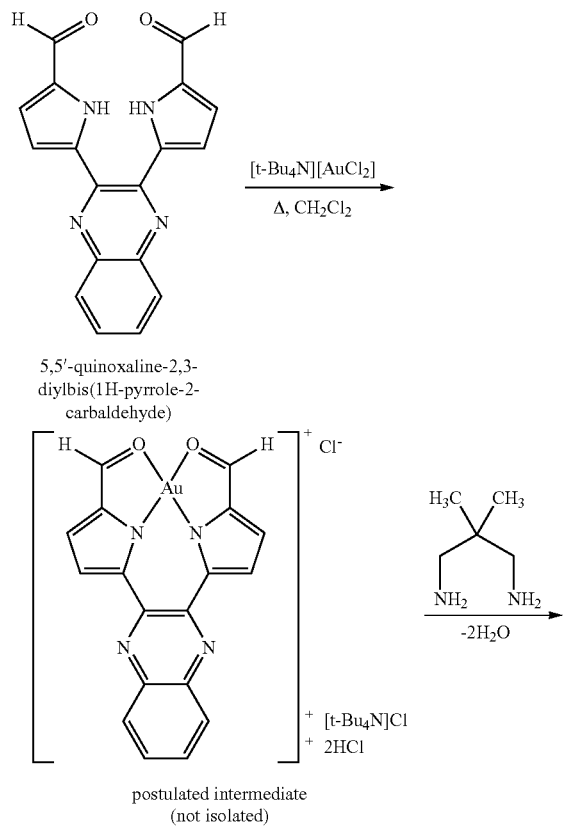

Scheme 27

5,5'-quinoxaline-2,3-diylbis(1H-pyrrole-2-carbaldehyde)

postulated intermediate (not isolated)

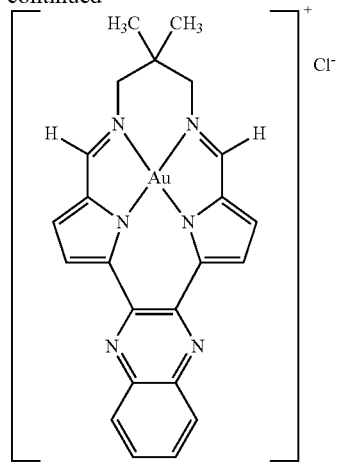

Initial macrocyclic reaction product prior to conversion to PF$_6^-$ salt

Metal-templated synthesis of the chloride salts of macrocyclic Au(III) compounds such as KA_AumacroDM and KA_AumacroBu. The chloride ion is then exchanged with PF$_6^-$ for crystallization.

2,3-Bis(5'-formylpyrrol-2'-yl)quinoxaline, alternatively named 5,5'-quinoxaline-2,3-diylbis(1H-pyrrole-2-carbaldehyde), was synthesized by the literature method.[41] A solution of 2,3-bis(5'-formylpyrrol-2'-yl)quinoxaline (54 mg, 0.172 mmols) in dichloromethane (10 mL) was added dropwise to tert-butylammonium tetrachloroaurate(III) (100 mg, 0.172 mmols) in dichloromethane (20 mL). The solution was allowed to reflux for 90 min before the addition 1,3-diamino-2,2-dimethylpropane (18 mg, 0.172 mmols) whereupon a yellow solid immediately precipitates out of solution. The reaction mixture was refluxed for a further 30 min and after this time triethylamine (35 mg, 0.344 mmols) was added after which the precipitate turned orange. The reaction mixture was refluxed for 1 hour before the orange precipitate was isolated and dried. This precipitate was dissolved in methanol and a saturated solution of ammonium hexafluorophosphate (V) was added to precipitate out the hexafluorophosphate salt of the gold complex. The precipitate was filtered and dried to afford an orange powder of {12,14-dihydro-13,13-dimethyl-6,9:17,20-diepimino[1,6]diazacyclo-heptadecino[12,13-β] quinoxalinato}gold(III) hexafluorophosphate(V) (45 mg, 36%). $^1$H NMR (500 MHz, DMSO-$d_6$): δ 1.19 (s, 6H, CH$_3$), 3.72 (s, 4H, =N—CH$_2$—C(CH$_3$)$_2$), 7.44 (d, $^3J_{HH}$=4.4 Hz, 2H, 3-pyrrole), 7.97-7.99 (dd, $^4J_{HH}$=3.3 Hz, $^3J_{HH}$=3.1 Hz, 2H, 6,7-quinoxaline), 7.99 (d, $^3J_{HH}$=4.4 Hz, 2H, 4-pyrrole), 8.17-8.19 (dd, $^4J_{HH}$=3.3 Hz, $^3J_{HH}$=3.1 Hz, 2H, 8,5-quinoxaline), 8.83 (s, 2H, —CH=N); $^{13}$C (125 MHz, DMSO-$d_6$): δ 23.09, 43.05, 61.57, 119.35, 123.39, 129.08, 132.31, 136.73, 139.67, 140.03, 148.43, 164.56; IR (cm$^{-1}$): 1569 (m), 1471 (w), 1405 (m), 1339 (w), 1238 (w), 1107 (m), 835 (s), 557 (m), 433 (m); UV-vis (CH$_3$CN) $\lambda_{max}$ [nm] (ε/M$^{-1}$ cm$^{-1}$): 230 (17 642), 249 (14 463), 309 (16 131), 348 (8 795), 375 (8 680), 458 (6 640), 481 (6 360); MS: m/z 577.1416 (M$^+$).

Procedure for Compound 1.5Y¹a

This complex was prepared by the same method used for the synthesis of 1.1Y¹b but with 1,4-diaminobutane (15.2 mg, 0.172 mmols) as the macrocycle-closing diamine to give a brown powder of compound 1.5Y¹a, {12,13,14,15-tetrahydro-6,9:18,21-diepimino[1,6]diazacyclooctadecino[12,13-b] quinoxalinato}gold(III) hexafluorophosphate(V) (20 mg, 16%). $^1$H NMR (500 MHz, DMSO-$d_6$): δ 2.04 (br, 4H, =N—CH$_2$—CH$_2$), 4.31 (br, 4H, =N—CH$_2$—CH$_2$), 7.45 (d, $^3J_{HH}$=4.4 Hz, 2H, 3-pyrrole), 7.95-7.97 (dd, $^4J_{HH}$=3.3 Hz, $^3J_{HH}$=3.1 Hz, 2H, 6,7-quinoxaoline), 8.06 (d, $^3J_{HH}$=4.4 Hz, 2H, 4-pyrrole), 8.17-8.18 (dd, $^4J_{HH}$=3.3 Hz, $^3J_{HH}$=3.1 Hz, 2H, 8,5-quinoxaline), 8.74 (s, 2H, —CH=N); $^{13}$C (125 MHz, DMSO-d$_6$): δ 23.68, 55.41, 118.92, 122.26, 128.52, 131.69, 135.69, 139.64, 139.72, 147.92, 164.83; IR (cm$^{-1}$): 2964 (w), 1590 (m), 1400 (m), 1354 (m), 1100 (m), 1059 (m), 829 (s), 555 (s), 446 (w); UV-vis (CH$_3$CN) λ$_{max}$ [nm] (ϵ/M$^{-1}$ cm$^{-1}$): 244 (16 439), 306 (19 364), 347 (13 712), 370 (13 425), 449 (9 825); MS: m/z 563.1265 (M$^+$).

Compound 1.1Y$^1$e, {13-chloro-12,14-dihydro-6,9:17,20-diepimino[1,6]diazacyclo-heptadecino[12,13-β]quinoxalinato}gold(III) hexafluorophosphate(V), was similarly synthesized.

Table 2 shows a summary of X-Ray data of some of the gold(III) chelates of the invention.

TABLE 2

Summary of X-Ray data of some of the gold(III) chelates of the invention

| Crystal Data For Structure | A | B | C |
|---|---|---|---|
| Formula | C$_{13}$H$_{14}$AuF$_6$N$_4$OP | C$_{15}$H$_{19}$AuClN$_4$O$_{0.5}$ | C$_{12}$H$_{12}$AuF$_6$N$_4$P |
| Compound number | MA_AuOH (1.1c) | MA_AuDM (1.1b) | MA_AuEn (1.2a) |
| Cell Setting | Monoclinic | Monoclinic | Orthorhombic |
| Space Group | P2$_1$/n | P2$_1$/c | Pbcn |
| Formula Weight | 584.22 | 495.76 | 554.2 |
| a/Å | 7.6496(2) | 13.5985(3) | 10.0520(5) |
| b/Å | 11.8256(4) | 11.9234(3) | 20.1960(5) |
| c/Å | 18.8218(6) | 19.7476(5) | 8.2450(5) |
| α/°; β/°; γ/° | 90; 101.181(3); 90 | 90; 97.299(2); 90 | 90; 90; 90 |
| T/K | 131(2) | 140(2) | 298(2) |
| Z | 4 | 4 | 4 |
| V/Å$^3$ | 1670.32(9) | 3175.94(13) | 1673.82(14) |
| Density (g cm$^{-3}$) | 2.323 | 2.074 | 2.20 |
| F(000) | 1104 | 1896 | 1039.7 |
| μ (mm$^{-1}$) | 8.977 | 9.435 | 8.948 |
| Crystal Dim. (mm$^3$) | 0.05 × 0.10 × 0.40 | 0.45 × 0.45 × 0.45 | 0.07 × 0.1 × 0.40 |
| Radiation M$_o$ K$_α$ (Å) | | 0.71073 | |
| Total data collected | 17500 | 31771 | 16589 |
| Unique Data | 3297 | 6250 | 1665 |
| R$_{int}$ | 0.0302 | 0.0741 | 0.068 |
| Refinement Method | | Full-matrix least-squares on F$^2$ | |
| Final R indices [I>2sigma(I)] | R$_1$ = 0.0206 wR$_2$ = 0.0399 | R$_1$ = 0.0424 wR$_2$ = 0.121 | R$_1$ = 0.050 wR$_2$ = 0.140 |
| Final R indices [all data] | R$_1$ = 0.0286 wR$_2$ = 0.0413 | R$_1$ = 0.0479 wR$_2$ = 0.1238 | R$_1$ = 0.072 wR$_2$ = 0.154 |
| Crystal Data for Structure | D | E | F |
| Formula | C$_{15}$H$_{17}$AuF$_6$N$_4$OP | C$_{15}$H$_{16}$AuClF$_6$N$_5$P | C$_{17}$H$_{14}$AuF$_6$N$_5$O |
| Compound number | MA_AuOEt (1.1d) | MA_AuCl (1.1e) | MA_AuTol (1.3b) |
| Cell Setting | Monoclinic | Monoclinic | Monoclinic |
| Space Group | P2$_1$/n | P2$_1$/n | P2$_1$/n |
| Formula Weight | 611.3 | 643.7 | 533.3 |
| a/Å | 8.2220(5) | 11.3580(3) | 17.7717(12) |
| b/Å | 10.5390(5) | 12.5390(5) | 8.9015(7) |
| c/Å | 21.1170(5) | 13.9730(4) | 22.696(16) |
| α/°; β/°; γ/° | 90; 95.430(5); 90 | 90; 106.490(5); 90 | 90; 102.530(7); 90 |
| T/K | 100(2) | 100(2) | 298(2) |
| Z | 4 | 4 | 8 |
| V/Å$^3$ | 1821.61(17) | 1908.16(32) | 3504.89(56) |
| Density (g cm$^{-3}$) | 2.229 | 2.24 | 2.02 |
| F(000) | 1164 | 1223.7 | 2031.3 |
| μ (mm$^{-1}$) | 8.237 | 8.003 | 8.422 |
| Crystal Dim. (mm$^3$) | 0.10 × 0.10 × 0.60 | 0.07 × 0.10 × 0.60 | 0.02 × 0.15 × 0.50 |
| Radiation M$_o$ K$_α$ (Å) | | 0.71073 | |
| Total data collected | 12681 | 18903 | 10005 |
| Unique Data | 3607 | 6137 | 5945 |
| R$_{int}$ | 0.0542 | 0.041 | 0.061 |
| Refinement Method | | Full-matrix least-squares on F$^2$ | |
| Final R indices [I>2sigma(I)] | R$_1$ = 0.0536 wR$_2$ = 0.1516 | R$_1$ = 0.040 wR$_2$ = 0.101 | R$_1$ = 0.079 wR$_2$ = 0.179 |
| Final R indices [all data] | R$_1$ = 0.0598 wR$_2$ = 0.1546 | R$_1$ = 0.051 wR$_2$ = 0.105 | R$_1$ = 0.133 wR$_2$ = 0.194 |

REFERENCES

[1] P. Zatta, *Coordination Chemistry Reviews*, 2009, (253), 1597-1598.

[2] I. Kostova, *Anti Cancer Agents in Medicinal Chemistry*, 2006, (6), 19-32.

[3] M. Rigobello, G. Scutari, R. Boscolo and A. Bindoli, *British Journal of Pharmacology*, 2002, (136), 1162-1168.

[4] S. Gunatilleke and A. Barrios, *Journal of Medicinal Chemistry*, 2006, (49), 3933-3937.

[5] V. Milacic and P. Dou, *Coordination Chemistry Reviews*, 2009, (253), 1649-1660.

[6] L. Ronconi, L. Giovagnini, C. Marzano, F. Bettiò, R. Graziani, G. Pilloni, and D. Fregona, *Inorganic Chemistry*, 2005, (44), 1867-1881.

[7] L. Ronconi, C. Marzano, P. Zanello, M. Corsini, G. Miolo, C. Macca, A. Trevisan, and D. Fregona, *Journal of Medicinal Chemistry*, 2006, (49), 1648-1657.

[8] L. Messori, F. Abbate, G. Marcon, P. Orioli, M. Fontani, E. Mini, T. Mazzei, S. Carotti, T. O'Connell, and P. Zanello, *Journal of Medicinal Chemistry*, 2000, (43), 3541-3548.

[9] G. Marcon, S. Carotti, M. Coronnello, L. Messori, E. Mini, P. Orioli, T. Mazzei, M. A. Cinellu, and G. Minghetti, *Journal of Medicinal Chemistry*, 2002, (45), 1672-1677.

[10] I. Ott, *Coordination Chemistry Reviews*, 2009, (253), 1970-1981.

[11] P. Calamai, S. Carotti, A. Guerri, L. Messori, E. Mini, P. Orioli and G. P. Speroni, *Journal of Inorganic Biochemistry*, 1997, (66), 103-109.

[12] A. Garza-Ortiz, H. den Dulk, J. Brouwer, H. Kooijman, A. L. Spek, J. Reedijk, *Journal of Inorganic Biochemistry*, 2007, (101), 1922-1930.
[13] R. W.-Y. Sun, C.-M. Che, *Coordination Chemistry Reviews*, 2009, (253), 1682-1691.
[14] O. Munro and G. Camp, *Acta Crystallographica Section C*, 2003, (C59), o672-o675.
[15] C. Stern, F. Franceschi, E. Solari, C. Floriani and R. Scopelliti, *Journal of Organometallic Chemistry*, 2000, (593), 86-95.
[16] A. Bacchi, M. Carcelli, L. Gabba, S. Ianelli, P. Pelagatti, G. Pelizzi, D. Rogolino, *Inorganica Chimica Acta*, 2003, (342), 229-235.
[17] N. Bailey, S. Hull, *Crystal Structure Communications*, 1976, (5) 447-451.
[18] U. Mueller-Westerhoff, A. Rheingold and M. Allen, 1996, Private communication to the Cambridge Structural Database. Reference No. 219663. Cambridge Crystallographic Data Centre, 12 Union Road, Cambridge England.
[19] F. Franceschi, G. Guillemot, E. Solari, C. Floriani, H. Birkedal and P. Patterson, *Chemistry: A European Journal*, 2001, (7), 1468-1478.
[20] H. Yokoi and W. Addison, *Inorganic Chemistry*, 1977, (16), 1341-1349.
[21] C. Berube, S. Gambarotta, G. Yap and P. Cozzi, *Organometallics*, 2003, (22), 434-439.
[22] Hai-Feng Xiang, Siu-Chung Chan, Kitty Kit-Ying Wu, Chi-Ming Che and P. T. Lai, *Chemical Communications*, 2005, 1408-1410.
[23] Jing-Wen Ran, Dao-Jun Onga, and Ya-Hong Li, *Acta Crystallographica Section E*, 2006, (E62), m2668-m2669.
[24] Y. Wang, H. Fu, A. Peng, Y. Zhao, J. Ma, Y. Maa and J. Yao, *Chemical Communications*, 2007, 1623-1625.
[25] B. B. Hasinoff, X. Wu, O. V. Krokhin, W. Ens, K. G. Standing, J. L. Nitiss, T. Sivaram, A. Giorgianni, S. Yang, Y. Jiang, and J. C. Yalowich, *Molecular Pharmacology*, 2005, (67), 937-947.
[26] L. H. Jensen, H. Liang, R. Shoemaker, M. Grauslund, M. Sehested and B. B. Hasinoff, *Molecular Pharmacology*, 2006, (70), 1503-1513.
[27] J. M. Fortune and N. Osheroff, *Prog. Nucleic Acid Res. Mol. Biol.*, 2000, (64), 221-253.
[28] B. B. Hasinoff, *Cardiovasc. Toxicol.*, 2002, (2), 111-118.
[29] L. H. Jensen, M. Sehested, US Patent: US20090209535A1.
[30] J. G. Hengstler, C. K. Heimerdinger, I. B. Schiffer, S. Gebhard, J. Sagemüller, B. Tanner, H. M. Bolt, F. Oesch, *EXCLI Journal*, 2002, (1), 8-14.
[31] A. Bacchi, M. Carcelli, L. Gabba, S. Ianelli, P. Pelagatti, G. Pelizzi, D. Rogolino, *Inorg. Chim. Acta*, 2003, (342), 229.
[32] L.-M. Chen, J. Liu, J.-C. Chen, C. P. Tan, S. Shi, K.-C. Zheng, L.-N. Ji, *J. Inorg. Biochem.*, 2008, (102), 330-341.
[33] A. Andersson, H. Ehrsson, *J. Pharm. Biomed. Anal.*, 1995, (13), 639-644.
[34] J. Lagona, P. Mukhopadhyay, S. Chakrabarti, L. Isaacs, *Angew. Chem. Int. Ed.* 2005, (44), 4844-4870.
[35] T. G. Appleton and J. R. Hall, *Inorganic Chemistry*, 1972, (11), 112-117.
[36] P. Nanjappan, N. Raju, K. Ramalingam, D. P. Nowotnik, *Tetrahedron*, 1994, (50), 8617-8632.
[37] P. Di Bernardo, P. L. Zanonato, S. Tamburini and P. A. Vigato, *Inorganica Chimica Acta*, 2007, (360), 1083-1094.
[38] K. Ramalingam, N. Raju, P. Nanjappan, N. Palaniappa and P. David, *Tetrahedron*, 1995, (51), 2875-2894.
[39] F. Taehee Kang, E. Yoon, E. Choi, S. Kim, J. Lee, *European Journal of Medicinal Chemistry*, 2009, (44), 239-250.
[40] S. L. Barnholtz, J. D. Lydon, G. Huang, M. Venkatesh, C. L. Barnes, A. R. Ketring, and S. S. Jurisson, *Inorganic Chemistry*, 2001, (40), 972-976.
[41] L. Wang, X.-J. Zhu, W.-Y. Wong, J.-P. Guo, W.-K. Wong, Z.-Y. Li, *Dalton. Trans.*, 2005, 3235-3240.

The invention claimed is:

1. A compound selected from compounds of the Formula (I),

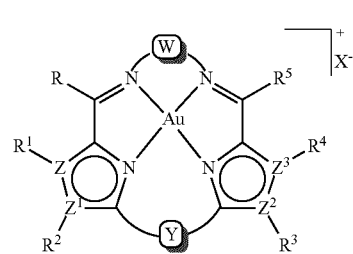

in which

W is independently selected from $W^1$, $W^2$, $W^3$, $W^4$, $W^5$,

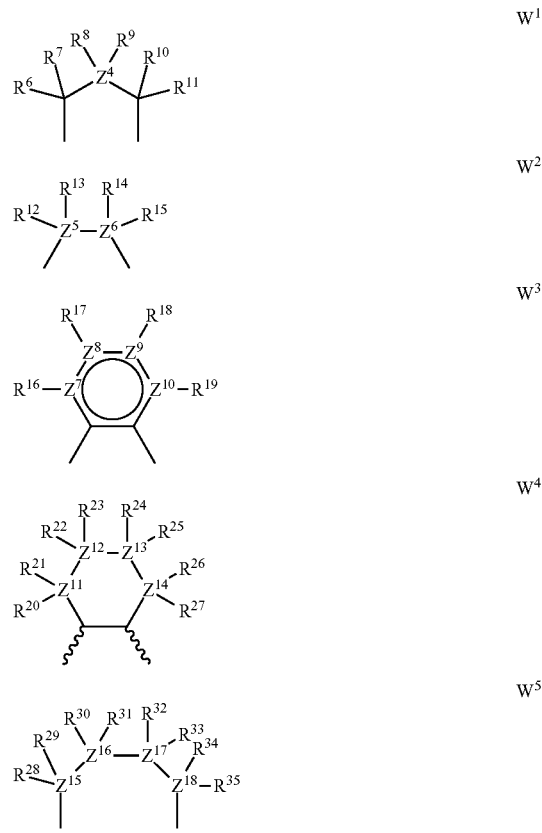

or W represents a pair of substituents independently selected from H, $C_1$-$C_6$ alkyl, $Z^5$ or $Z^6$ aryl or $C_1$-$C_6$ amide in which the amide is optionally part of a linking chain, and the $Z^n$—$Z^{n'}$ bonds (n=4-17; n'=n+1) are optionally of any whole or partial bond order, Y is $Y^1$

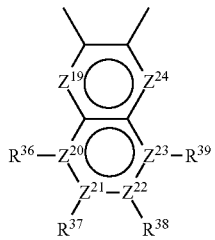

or Y represents a pair of substituents independently selected from H, $C_1$-$C_6$ alkyl, $Z^5$ or $Z^6$ aryl, or Y is optionally a bridging structure that may comprise one or more $C_1$-$C_6$ amide, $C_1$-$C_6$ ether, or $C_1$-$C_6$ ester groups, R—$R^{39}$ are independently selected from no substituent, a lone pair of electrons, H, halogen, $C_5$-$C_6$ aryl, $C_1$-$C_{12}$ alkyl, amine, $C_1$-$C_6$ alkylamine, $C_1$-$C_6$ amide, nitro, cyano, carboxyl, $C_1$-$C_6$ ester, phosphane, thiol, $C_1$-$C_6$ thioether, $OR^{40}$, and suitable pairs of adjacent R groups (R—$R^{39}$) may optionally together form part of a $C_5$ or $C_6$ aryl ring, a $Z^5$ or $Z^6$ ring, $R^{40}$ is independently selected from H, $C_1$-$C_6$ alkyl, $Z^5$ or $Z^6$ aryl, $C_1$-$C_6$ ester, poly(—$C_2O$—), amine, and $C_1$-$C_6$ alkylamine, Z—$Z^{24}$ are independently selected from C, N, P, O, and S, and $X^-$ is a pharmaceutically acceptable anion.

2. The compound of claim 1, in which the anion is selected from halide, hexafluorophosphate, nitrate, and triflate.

3. The compound of claim 1, in which Y represents two hydrogen atoms or $Y^1$.

4. The compound of claim 3, in which Y is $Y^1$ and $Z^{19}$ and $Z^{24}$ are N.

5. The compound of claim 4, in which $Z^{20}$-$Z^{23}$ are C.

6. The compound of claim 1, in which R—$R^5$ are selected from H, $C_1$-$C_3$ alkyl, O—$C_1$-$C_3$ alkyl, hydroxyl and halogen.

7. The compound of claim 6, in which $C_1$-$C_3$ alkyl is methyl, O—$C_1$-$C_3$ alkyl is O-ethyl, and halogen is chlorine.

8. The compound of claim 1, in which W is selected from $W^1$, $W^2$, $W^3$, $W^4$ or $W^5$.

9. The compound of claim 8, in which $R^6$-$R^{35}$ are selected from H, $C_1$-$C_3$ alkyl, O—$C_1$-$C_3$ alkyl and halogen.

10. The compound of claim 9, in which $C_1$-$C_3$ alkyl is methyl, O—$C_1$-$C_3$ alkyl is O-ethyl and halogen is chlorine.

11. A gold(III) compound selected from:
2,2'-{propane-1,3-diylbis[nitrilo(E)methylylidene]}bis(pyrrol-1-ido)gold(III) chloride,
2,2'-{(2,2-dimethylpropane-1,3-diyl)bis[nitrilo(E)methylylidene]}bis(pyrrol-1-ido)gold(III) chloride,
2,2'-{(2-hydroxypropane-1,3-diyl)bis[nitrilo(E)methylylidene]}bis(pyrrol-1-ido)gold(III) hexafluorophosphate(V),
2,2'-{(2-ethoxypropane-1,3-diyl)bis[nitrilo(E)methylylidene]}bis(pyrrol-1-ido)gold(III) hexafluorophosphate(V),
2,2'-{(2-chloropropane-1,3-diyl)bis[nitrilo(E)methylylidene]}bis(pyrrol-1-ido)gold(III) hexafluorophosphate(V),
2,2'-{ethane-1,2-diylbis[nitrilo(E)methylylidene]}bis(pyrrol-1-ido)gold(III) hexafluorophosphate(V),
2,2'-{(2S)-propane-1,2-diylbis[nitrilo(E)methylylidene]}bis(pyrrol-1-ido)gold(III) hexafluorophosphate(V),
2,2'-{(1R,2R)-cyclohexane-1,2-diylbis[nitrilo(E)methylylidene]}bis(pyrrol-1-ido)gold(III) hexafluorophosphate(V),
2,2'-{(1S,2S)-cyclohexane-1,2-diylbis[nitrilo(E)methylylidene]}bis(pyrrol-1-ido)gold(III) hexafluorophosphate(V),
2,2'-{cyclohexane-1,2-diylbis[nitrilo(E)methylylidene]}bis(pyrrol-1-ido)gold(III) hexafluorophosphate(V)
2,2'-{(4-methylbenzene-1,2-diyl)bis[nitrilo(E)methylylidene]}bis(pyrrol-1-ido)gold(III) nitrate(V),
4,4'-{propane-1,3-diyl)bis[nitrilo(E)methylylidene]}bis(5-methylimidazol-1-ide)gold(III) hexafluorophosphate(V),
4,4'-{(2,2-dimethylpropane-1,3-diyl)bis[nitrilo(E)methylylidene]}bis(5-methylimidazol-1-ide)gold(III) hexaflurophosphate(V),
{12,13-dihydro-14H-6,9:17,20-diepimino[1,6]diazacyclo-heptadecino[12,13-β]quinoxalinato}gold(III) hexafluorophosphate(V),
{12,14-dihydro-13,13-dimethyl-6,9:17,20-diepimino[1,6]diazacyclo-heptadecino[12,13-β]quinoxalinato}gold(III) hexafluorophosphate(V),
{12,13,14,15-tetrahydro-6,9:18,21-diepimino[1,6]diazacyclooctadecino[12,13-b]quinoxalinato}gold(III) hexafluorophosphate(V), and
{13-chloro-12,14-dihydro-6,9:17,20-diepimino[1,6]diazacyclo-heptadecino[12,13-β]quinoxalinato}gold(III) hexafluorophosphate(V).

12. The compound of claim 1 for the treatment of cancer.

13. A pharmaceutical composition comprising at least one compound of claim 1.

14. A method of preparing a compound of Formula (I) as claimed in claim 1, which includes the steps of condensing a diamine of the general formula A

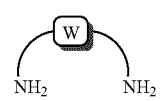

simultaneously or consecutively with a carbonyl compound selected from compounds of the general formula B, C and D

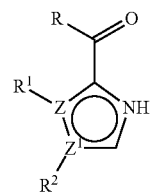

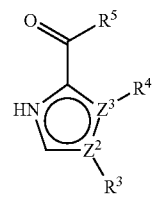

-continued

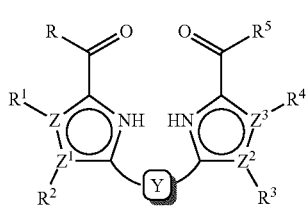

D to produce a diimine Schiff base of the general formula E or F

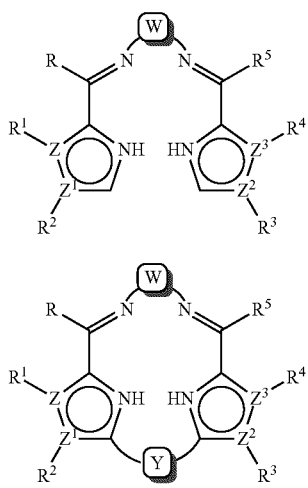

and reacting the diimine of general formula E or F with a tetraalkylammonium tetrahaloaurate(III) to produce the gold(III) compound of the general Formula (I) in which W, Y, R, Z and X are as described in claim 1.

15. A method of preparing a compound of general Formula (I) as claimed in claim 1, which includes the step of reacting a carbonyl compound of the general formula D

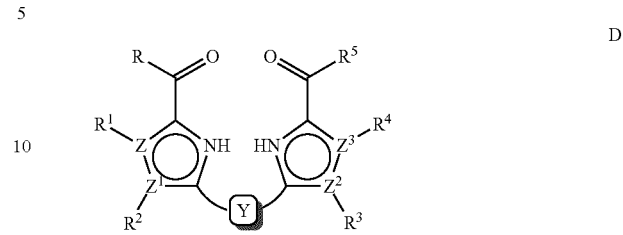

with a tetraalkylammonium tetrahaloaurate(III) and, consecutively or simultaneously, a diamine to produce the compound of general Formula (I) in which W, Y, R, Z and X are as described in claim 1.

16. The method of claim 14, in which the tetraalkylammonium tetrahaloaurate(III) is tetrabutylammonium tetrachloroaurate(III).

17. The method of claim 16, in which the tetraalkylammonium tetrahaloaurate(III) is tetra-t-butylammonium tetrachloroaurate(III).

18. The method of claim 15, in which reacting with the tetraalkylammonium tetrahaloaurate(III) is carried out in the presence of a salt selected from halides, hexafluorophosphates, nitrates, and triflates.

19. The method of claim 18, in which the salt is a tetraalkylammonium hexafluorophosphate.

20. The method of claim 19, in which the salt is tetra-t-butylammonium hexafluorophosphate.

21. The method of claim 15, in which the compound of Formula (I) is a chloride and the method includes the further step of reacting the compound of Formula (I) in which $X^-$ is chloride with a salt selected from halides other than chloride, hexafluorophosphates, nitrates, and triflates to produce a compound of Formula (I) in which $X^-$ is the anion of the said salt.

* * * * *